(12) United States Patent
Alargova et al.

(10) Patent No.: US 8,217,172 B2
(45) Date of Patent: Jul. 10, 2012

(54) SOLID FORMS OF 1-ETHYL-3-(5-(5-FLUOROPYRIDIN-3-YL)-7-(PYRIMIDIN-2-YL)-1H-BENZO[D]IMIDAZOL-2-YL)UREA

(75) Inventors: Rossitza Alargova, Brighton, MA (US); Irina Kadiyala, Newton, MA (US); Arnaud Le Tiran, Lexington, MA (US); Dainius Macikenas, Watertown, MA (US); Yeugang Zhang, Wayland, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 806 days.

(21) Appl. No.: 12/329,179

(22) Filed: Dec. 5, 2008

(65) Prior Publication Data

US 2010/0063284 A1     Mar. 11, 2010

Related U.S. Application Data

(60) Provisional application No. 61/012,355, filed on Dec. 7, 2007.

(51) Int. Cl.
   *C07D 401/08*     (2006.01)
(52) U.S. Cl. ....................................... 544/333
(58) Field of Classification Search .............. 544/333
   See application file for complete search history.

(56) References Cited

U.S. PATENT DOCUMENTS

| | | | |
|---|---|---|---|
| 6,632,809 B2 | 10/2003 | Grillot et al. | |
| RE40,245 E | 4/2008 | Grillot et al. | |
| 7,414,046 B2 | 8/2008 | Grillot et al. | |
| 7,495,014 B2 | 2/2009 | Charifson et al. | |
| 7,569,591 B2 | 8/2009 | Charifson et al. | |
| 7,582,641 B2 | 9/2009 | Charifson et al. | |
| 7,618,974 B2 | 11/2009 | Charifson et al. | |
| 7,727,992 B2 | 6/2010 | Charifson et al. | |
| 8,034,832 B2 | 10/2011 | Charifson et al. | |
| 8,067,606 B2 | 11/2011 | Charifson et al. | |
| 2005/0038247 A1* | 2/2005 | Charifson et al. | ............ 544/295 |
| 2009/0176771 A1 | 7/2009 | Charifson et al. | |
| 2010/0063069 A1 | 3/2010 | Charifson et al. | |
| 2011/0104207 A1 | 5/2011 | Charifson et al. | |

FOREIGN PATENT DOCUMENTS

| | | |
|---|---|---|
| WO | 2006/022773 | 3/2006 |
| WO | 2007/056330 | 5/2007 |

OTHER PUBLICATIONS

Brittain, Polymorphism in Pharmaceutical Solids, vol. 95; Drugs and Pharmaceutical Sciences.*
Search Report WO 2009/076200 A3, (2009).
Threlfall et al: "Analysis of Organic Polymorphs" Analyst, London, GB,, vol. 12, (Oct. 1, 1995), pp. 2435-2460.
Leusen F J J: "Ab initio prediction of polymorphs" Journal of Crystal Growth, Elsevier, Amsterdam, NL, vol. 166, No. 1, (Sep. 1, 1996) pp. 900-903.

\* cited by examiner

*Primary Examiner* — James O. Wilson
*Assistant Examiner* — Ebenezer O Sackey
(74) *Attorney, Agent, or Firm* — Michael C. Badia

(57) ABSTRACT

Solid forms of crystalline1-ethyl-3-(5-(5-fluoropyridin-3-yl)-7-(pyrimidin-2-yl)-1H-benzo[d]imidazol-2-yl)urea, compositions containing solid forms of crystalline1-ethyl-3-(5-(5-fluoropyridin-3-yl)-7-(pyrimidin-2-yl)-1H-benzo[d]imidazol-2-yl)urea and methods of using the same are described.

12 Claims, 30 Drawing Sheets

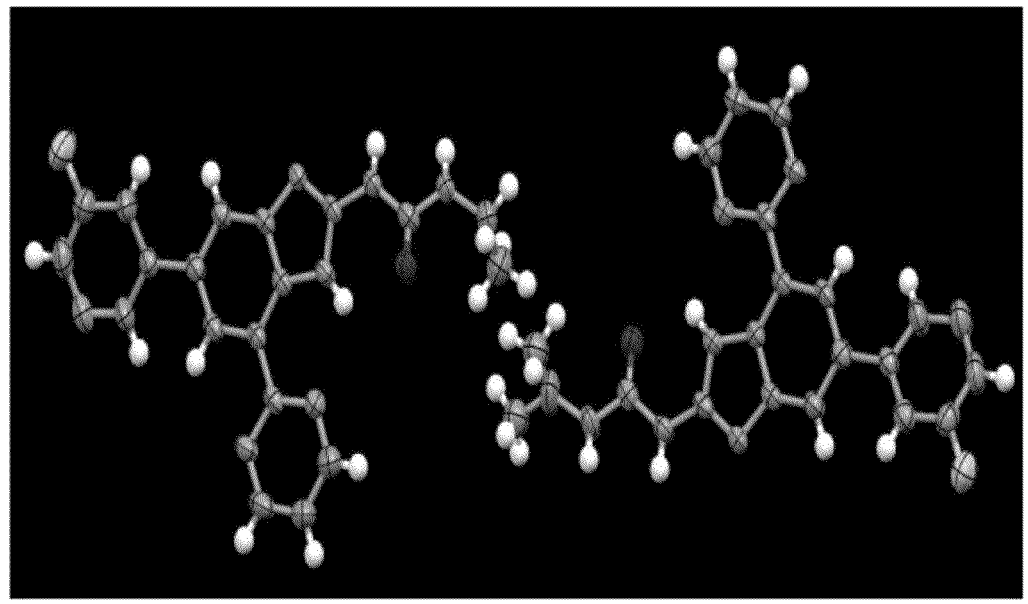
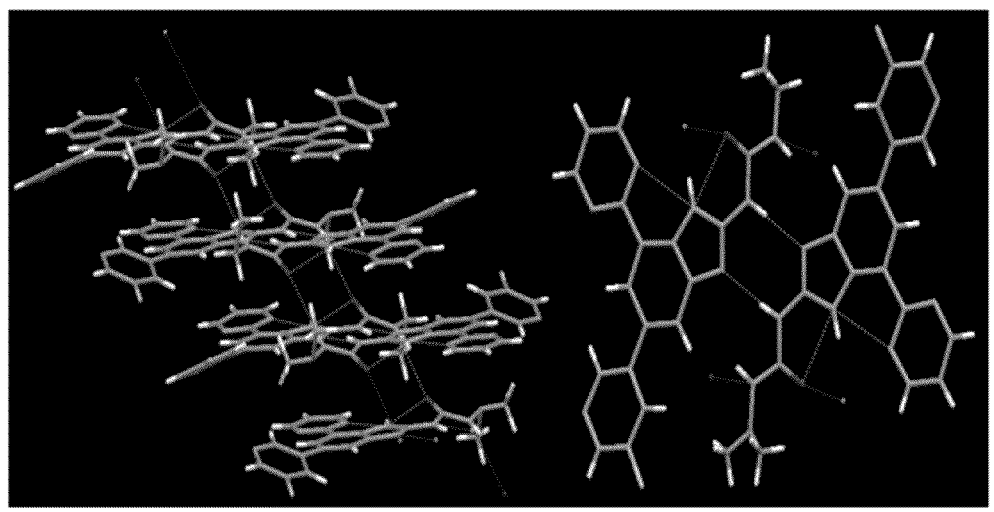
Figures 1a and 1b Observed crystal structure of form IA

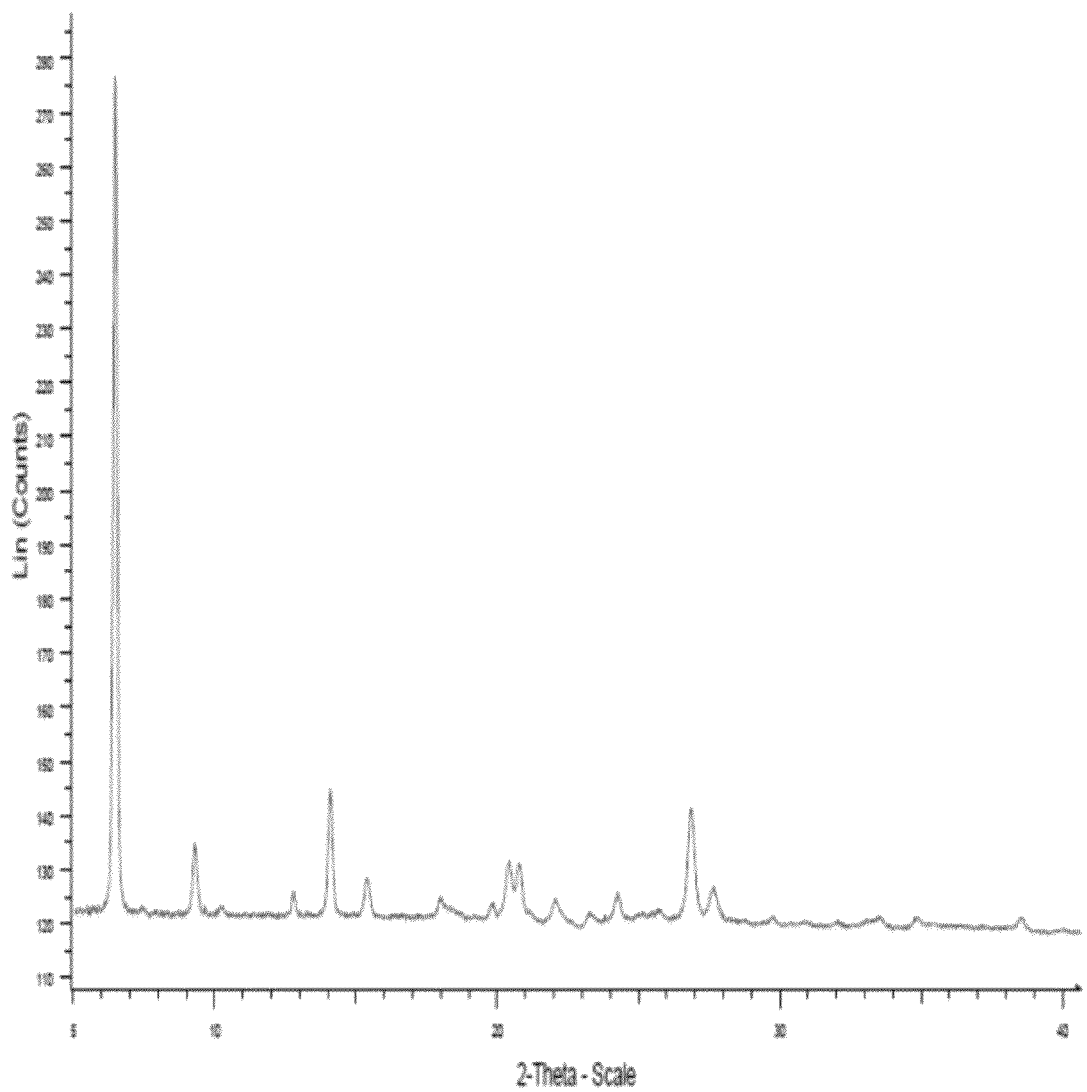
Figure 2   Representative XRPD of Form IA

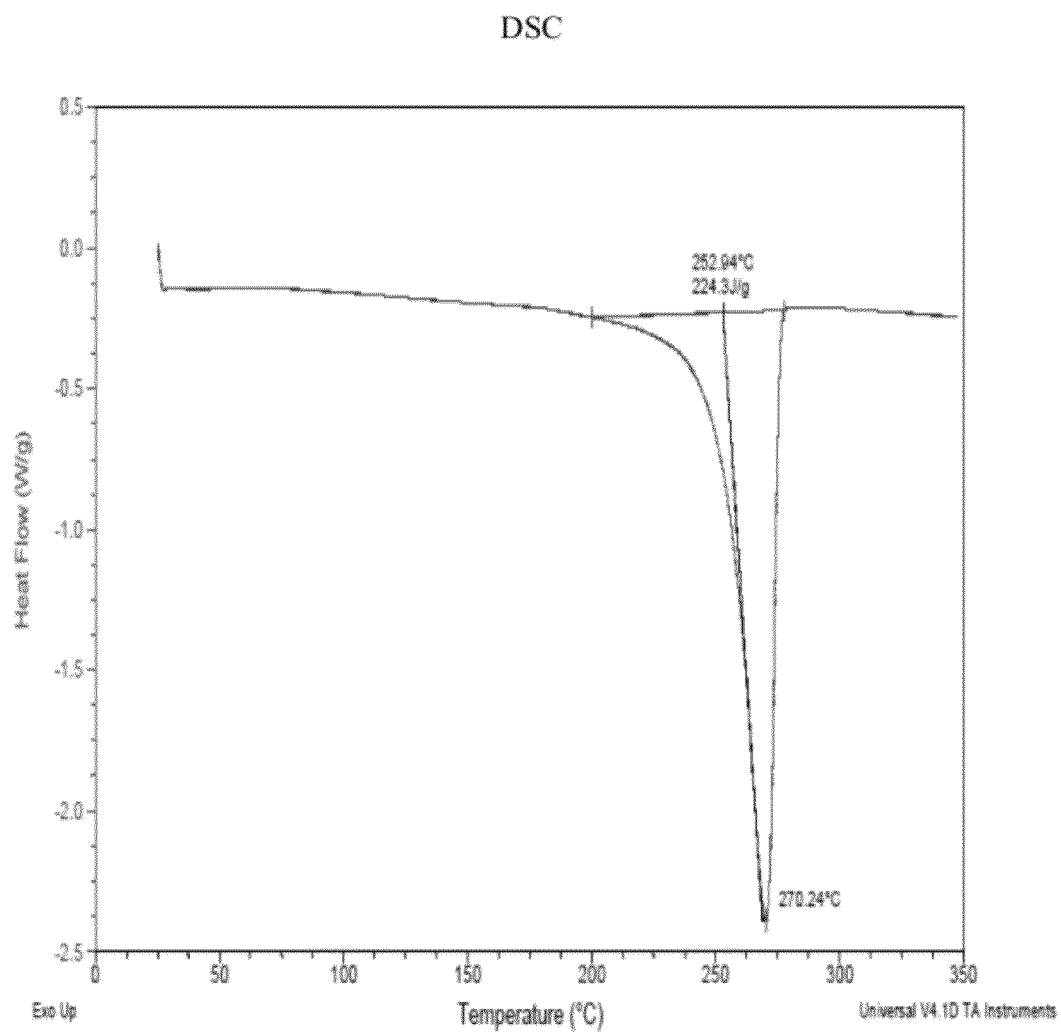
Figure 3  Representative DSC data collected for Form IA

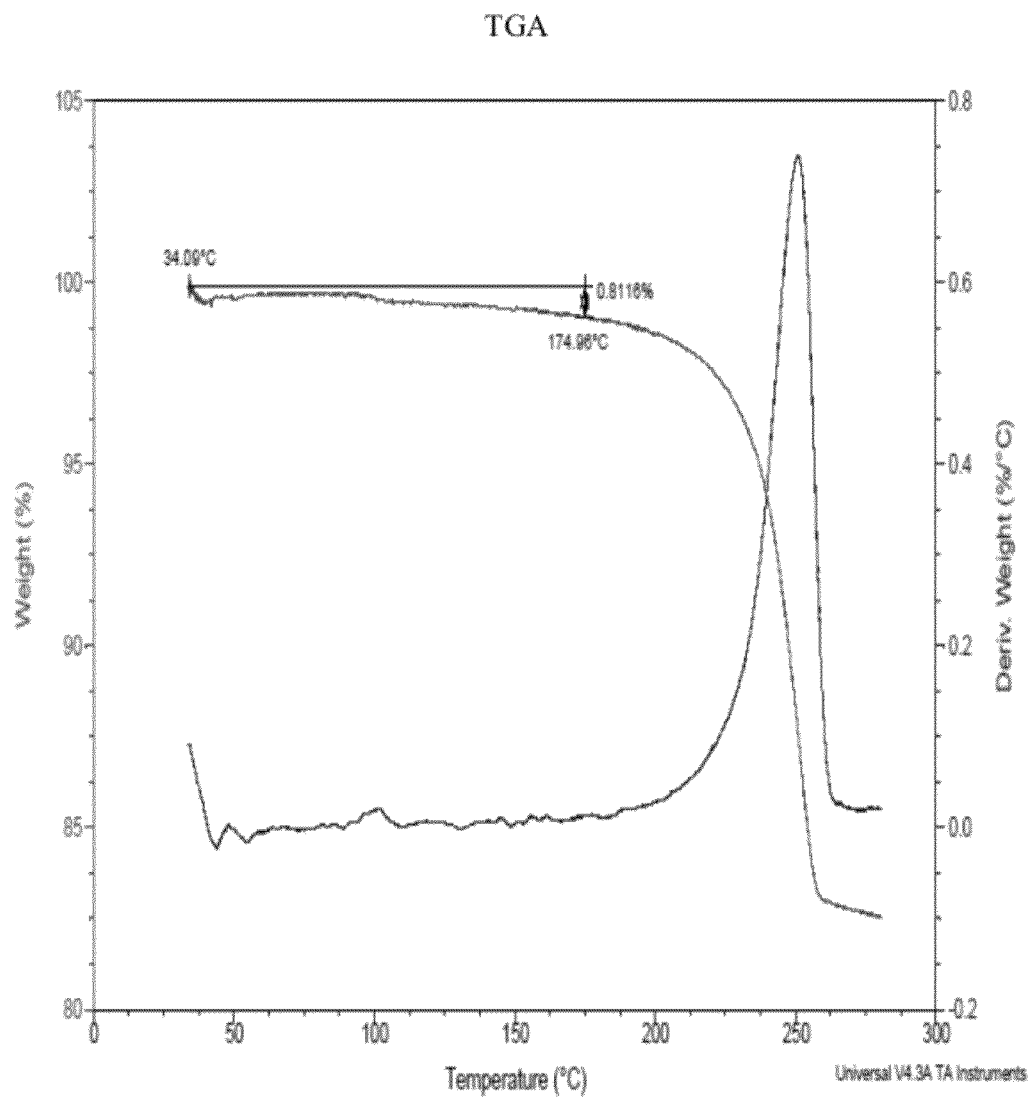
Figure 4 Representative TGA data collected for Form IA

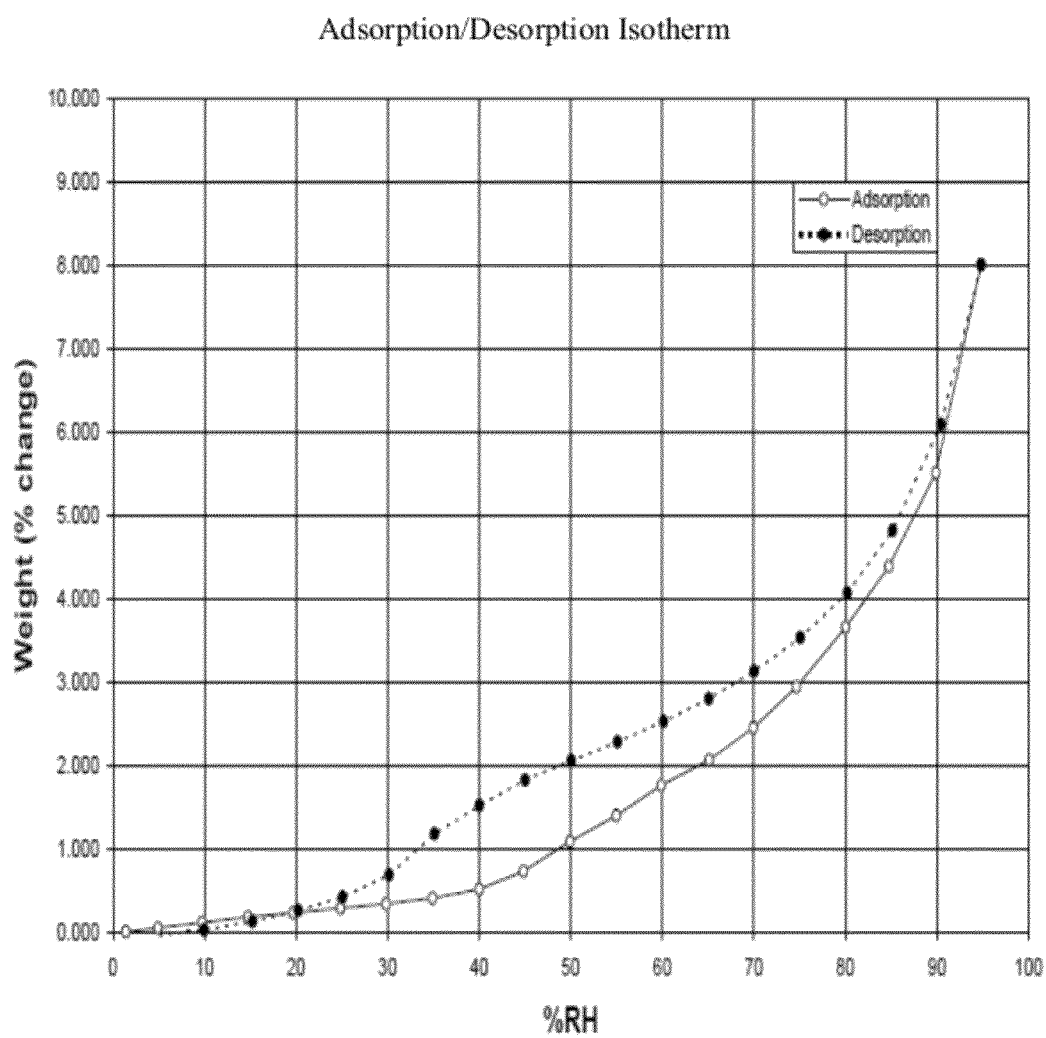
Figure 5  Representative Moisture Sorption Isotherm of Form IA

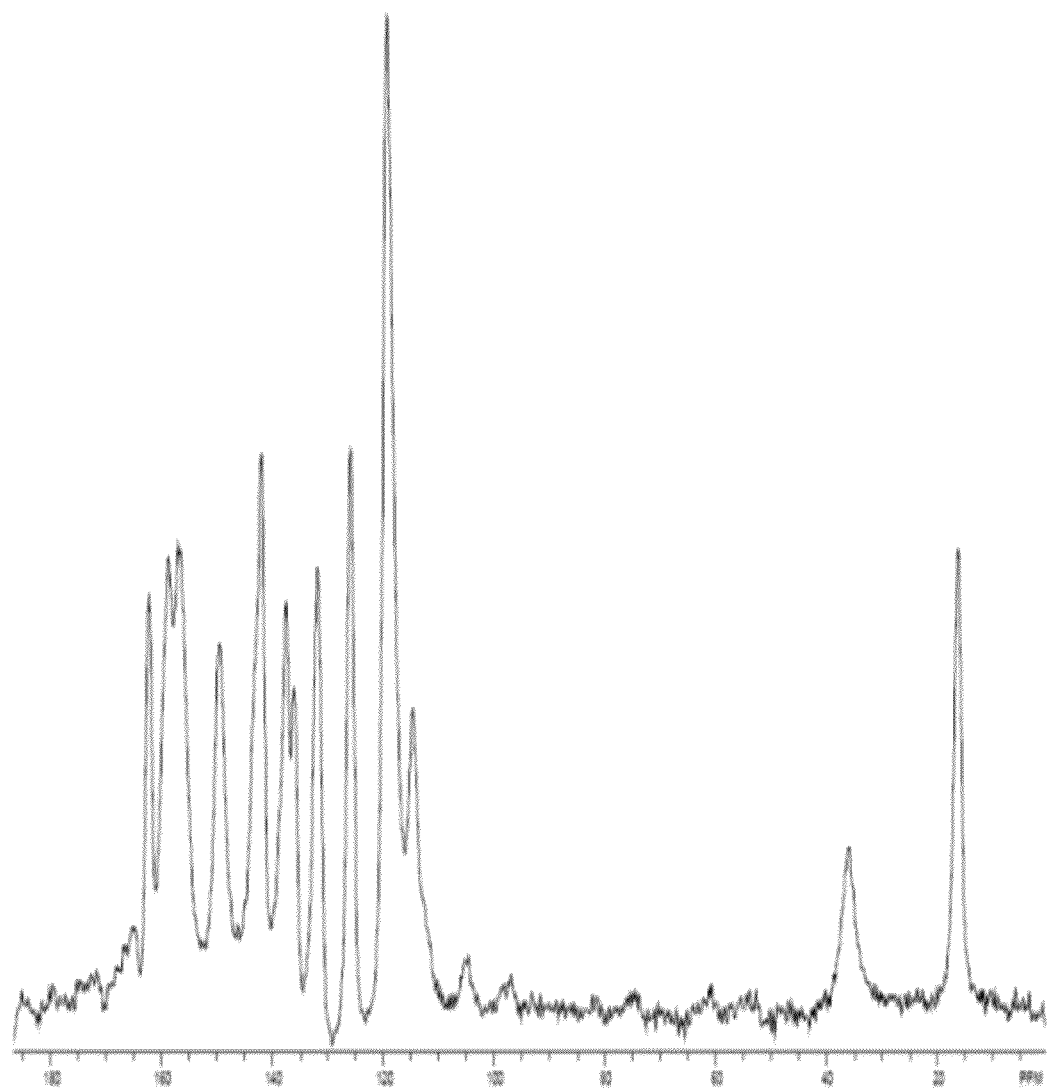
Figure 6 13C ssNMR pattern of Form IA

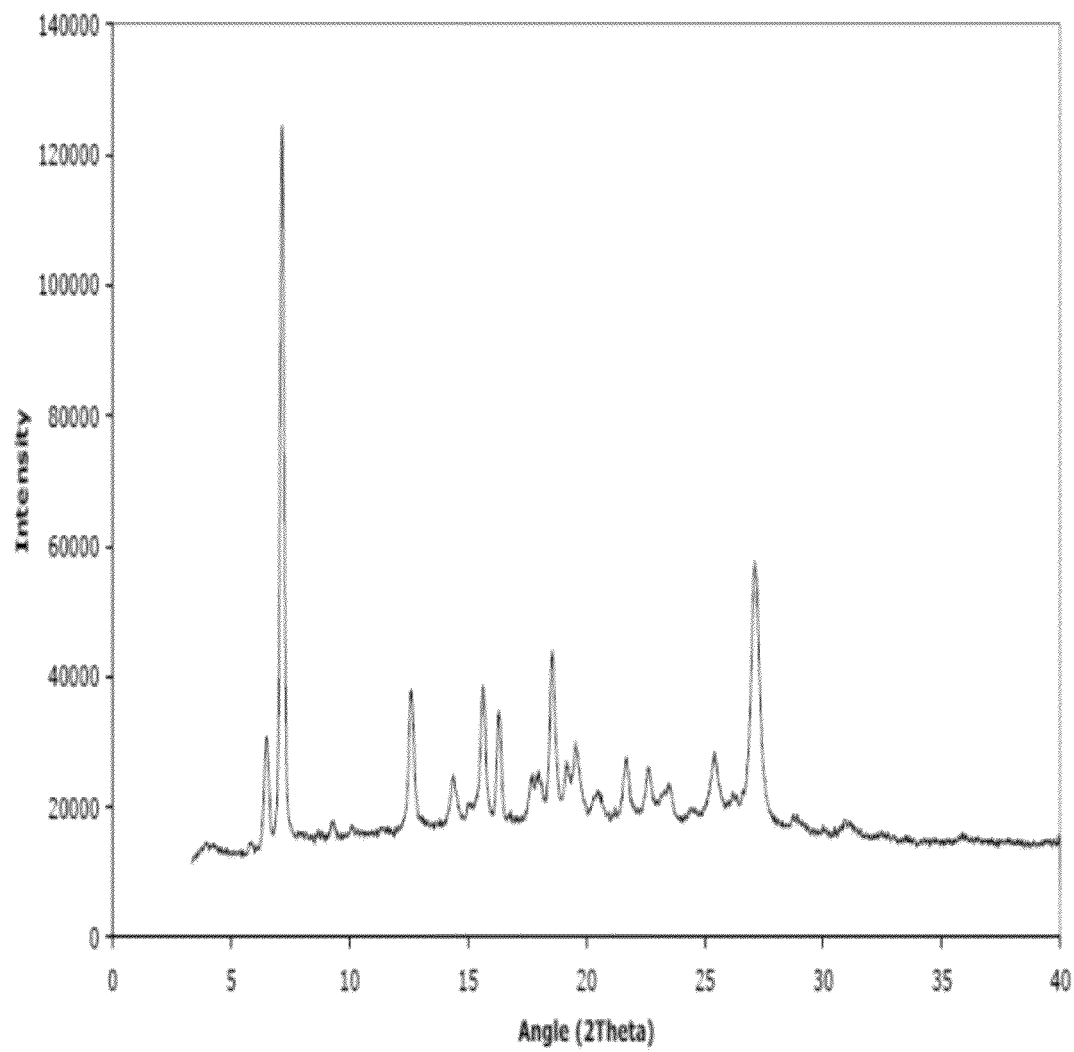
Figure 7  Representative XRPD of Form IIA

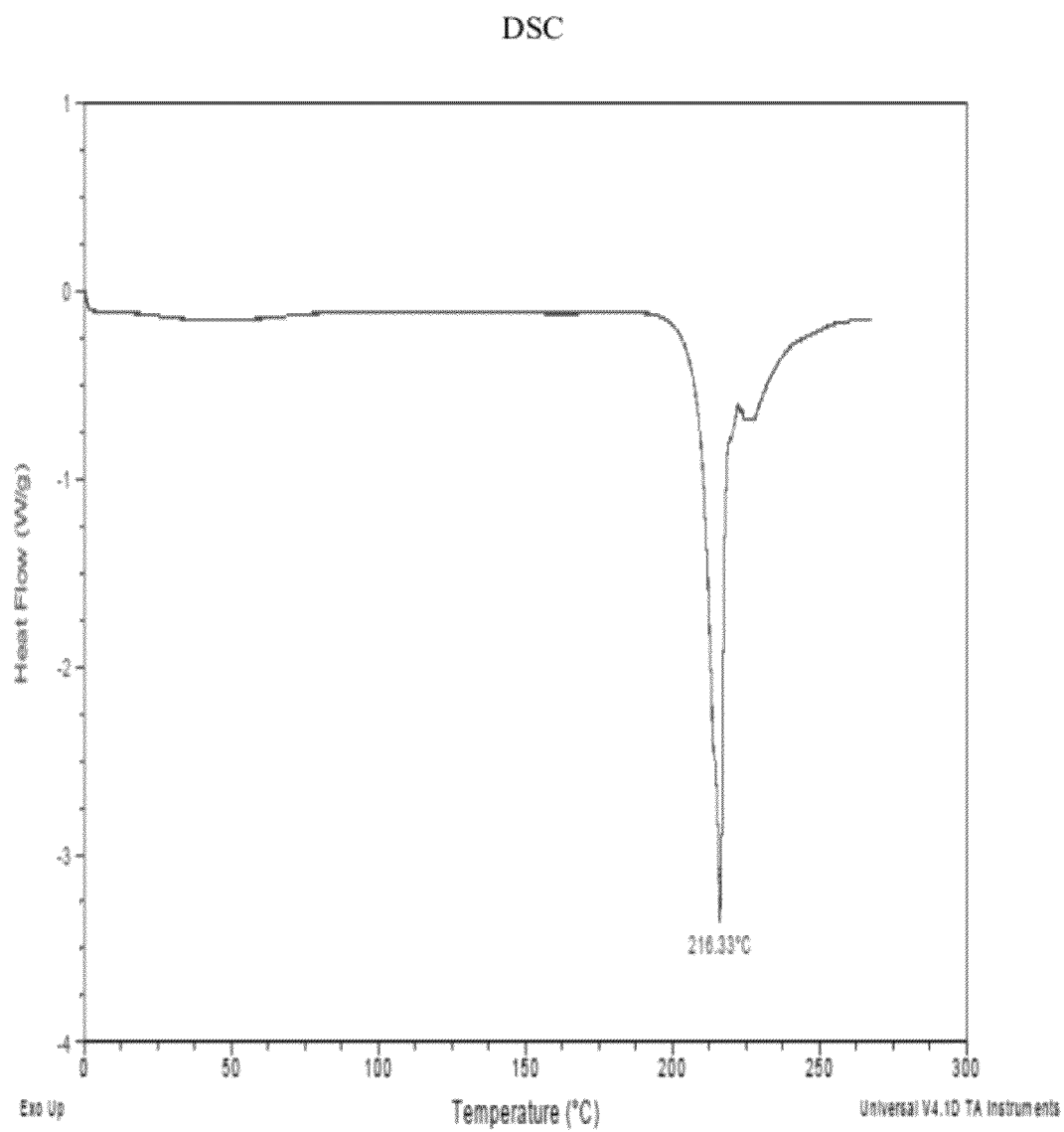
Figure 8    Representative DSC data collected for Form IIA

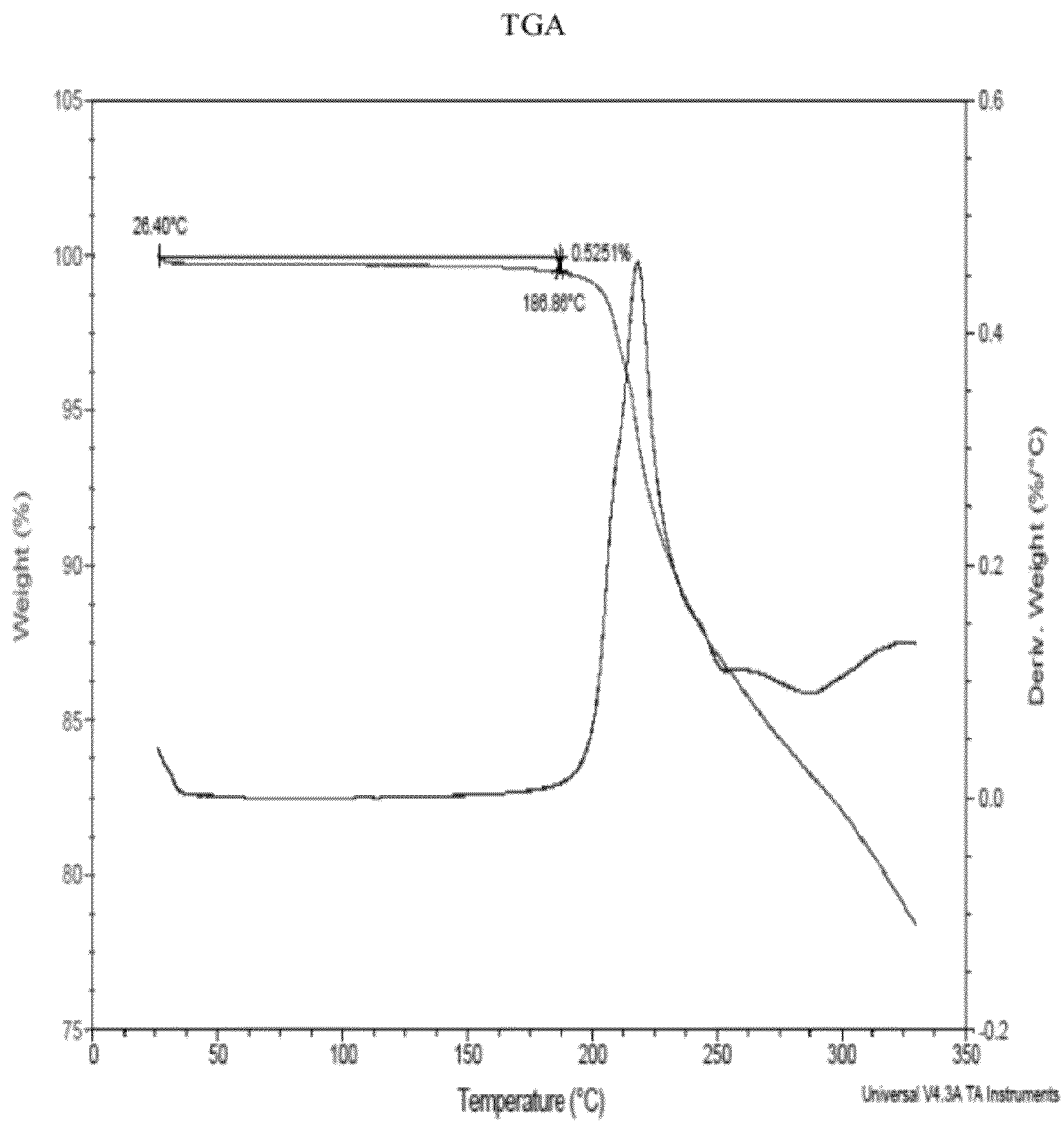
Figure 9  Representative TGA data collected Form IIA

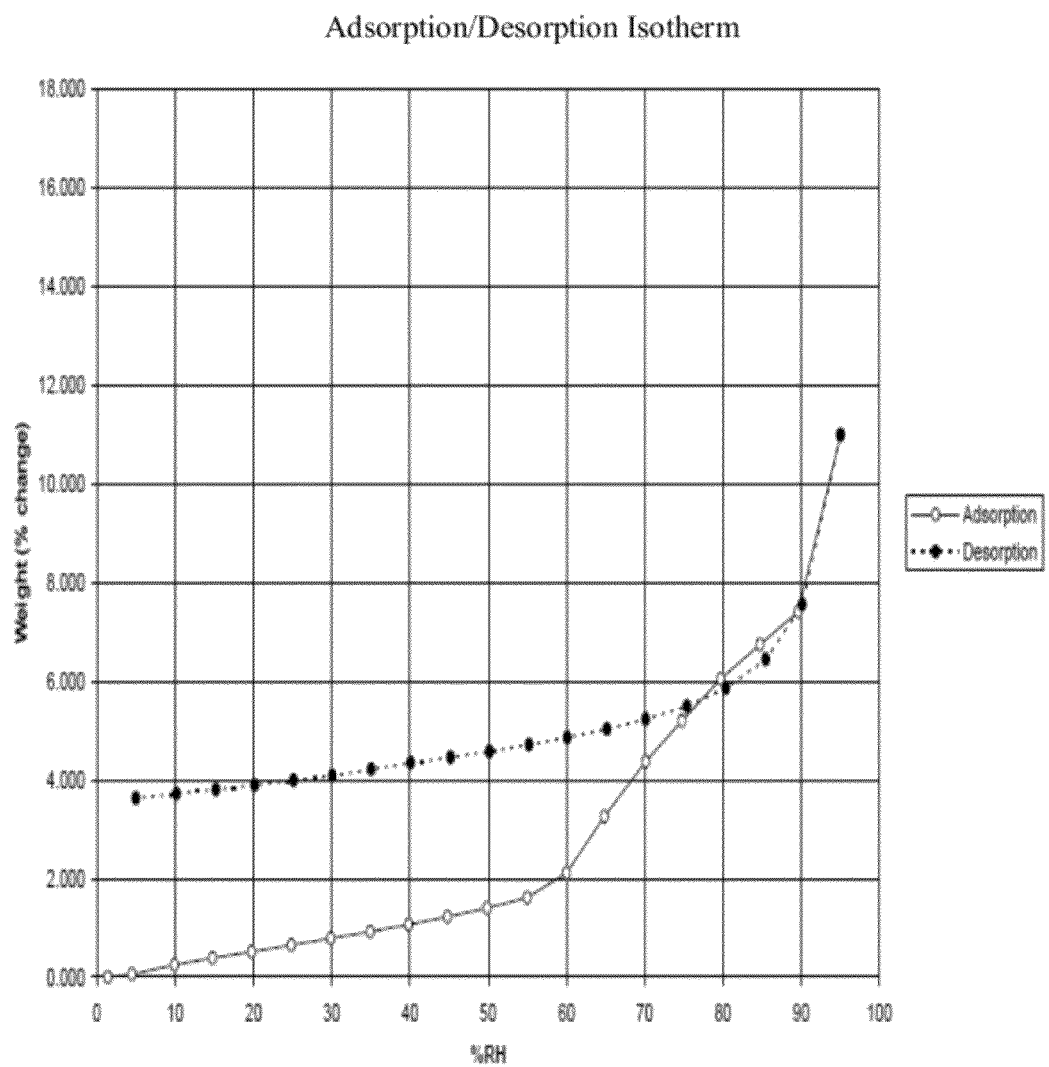
Figure 10  Representative Moisture Sorption Isotherm of Form IIA

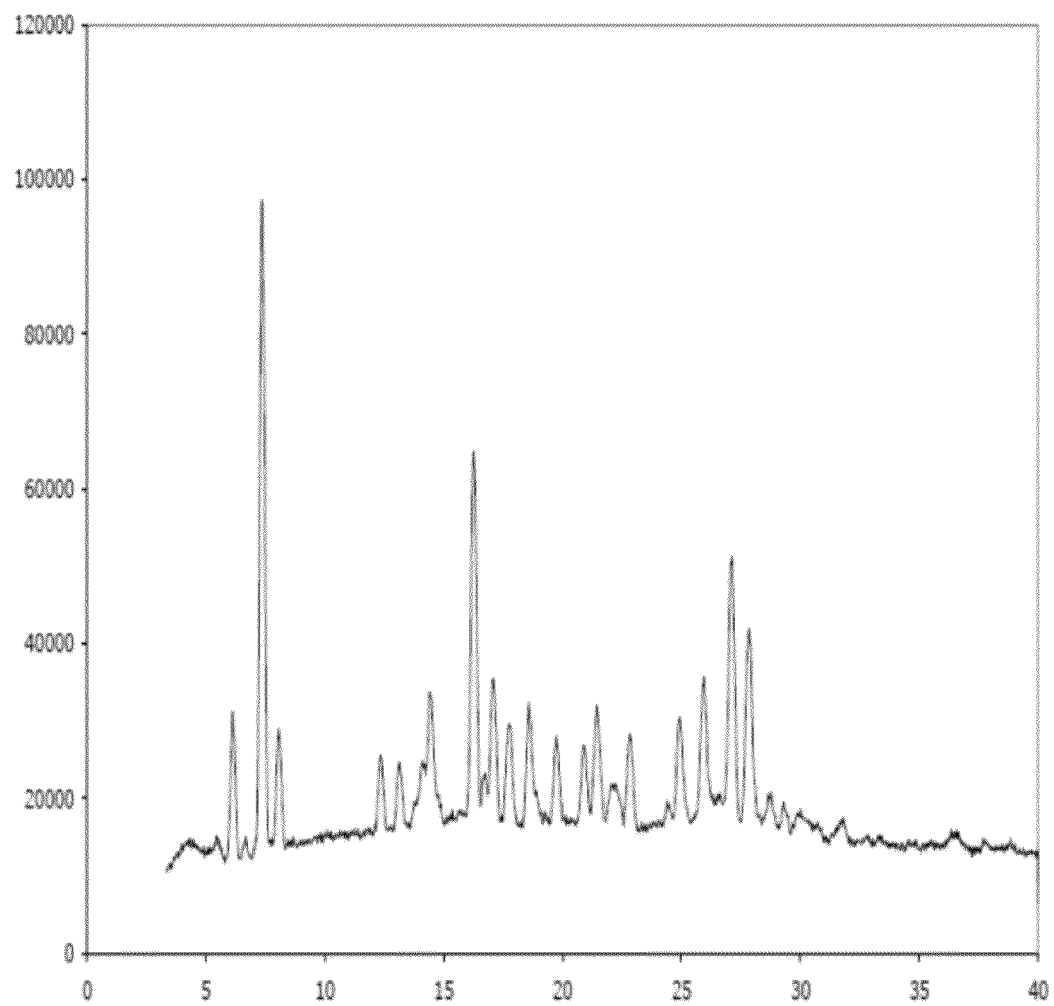
Figure 11  Representative XRPD of Form IIB

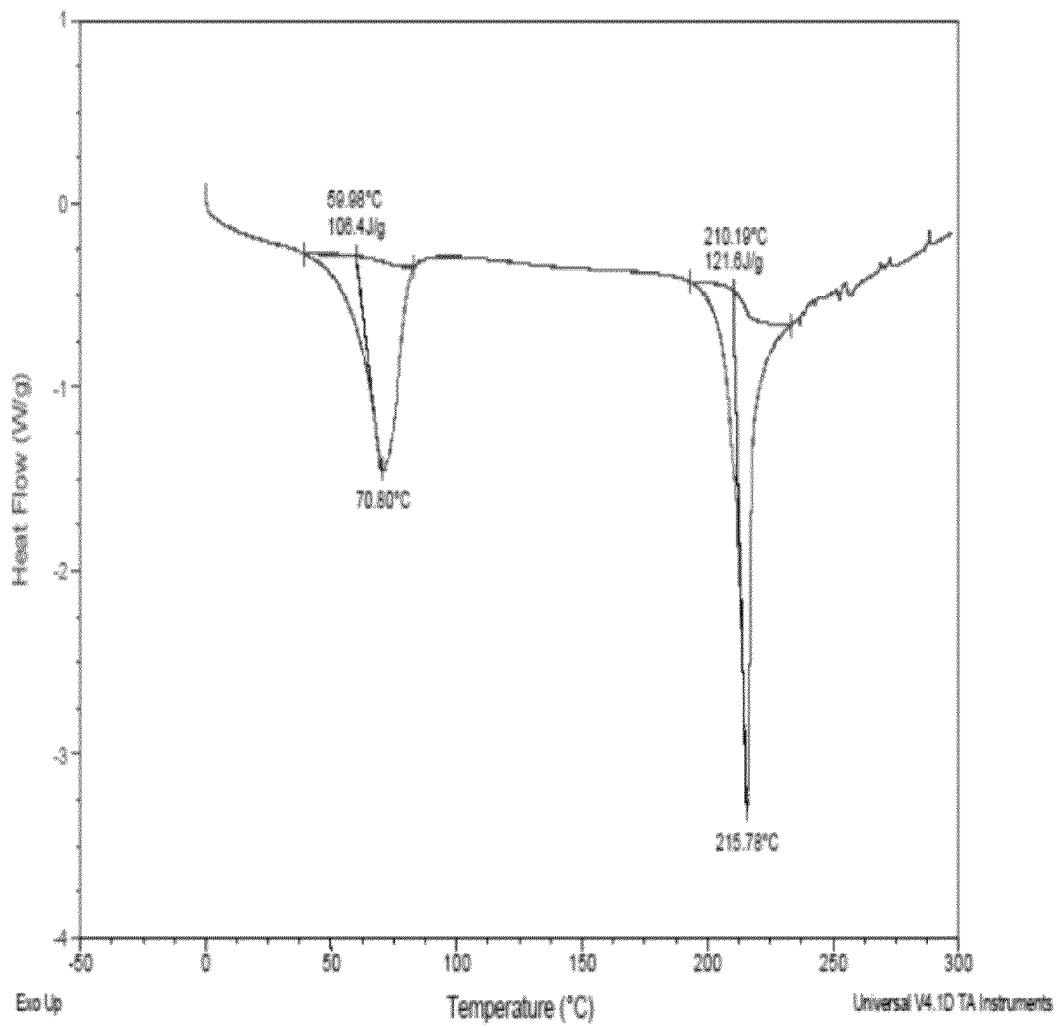
Figure 12 Representative DSC data collected for Form IIB

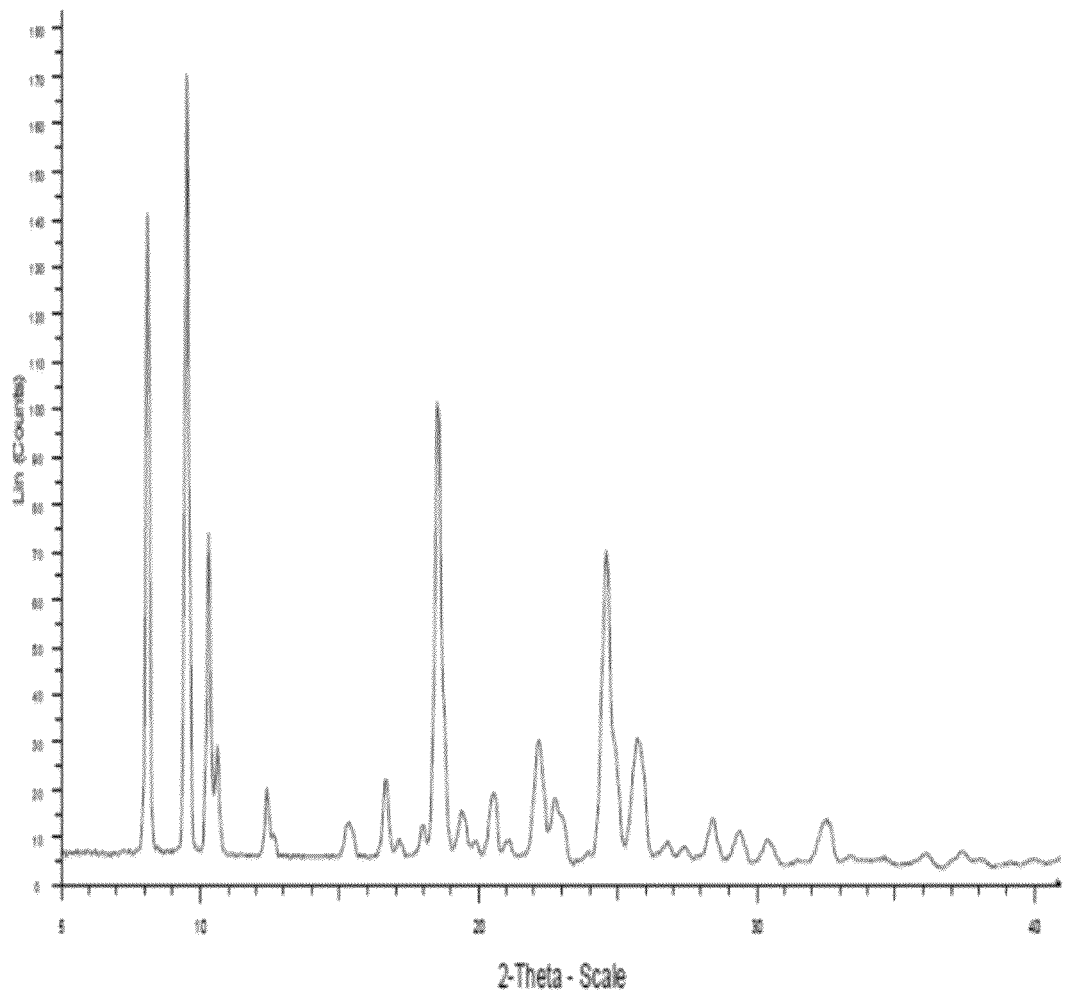
Figure 13  Representative XRPD of Form IIC

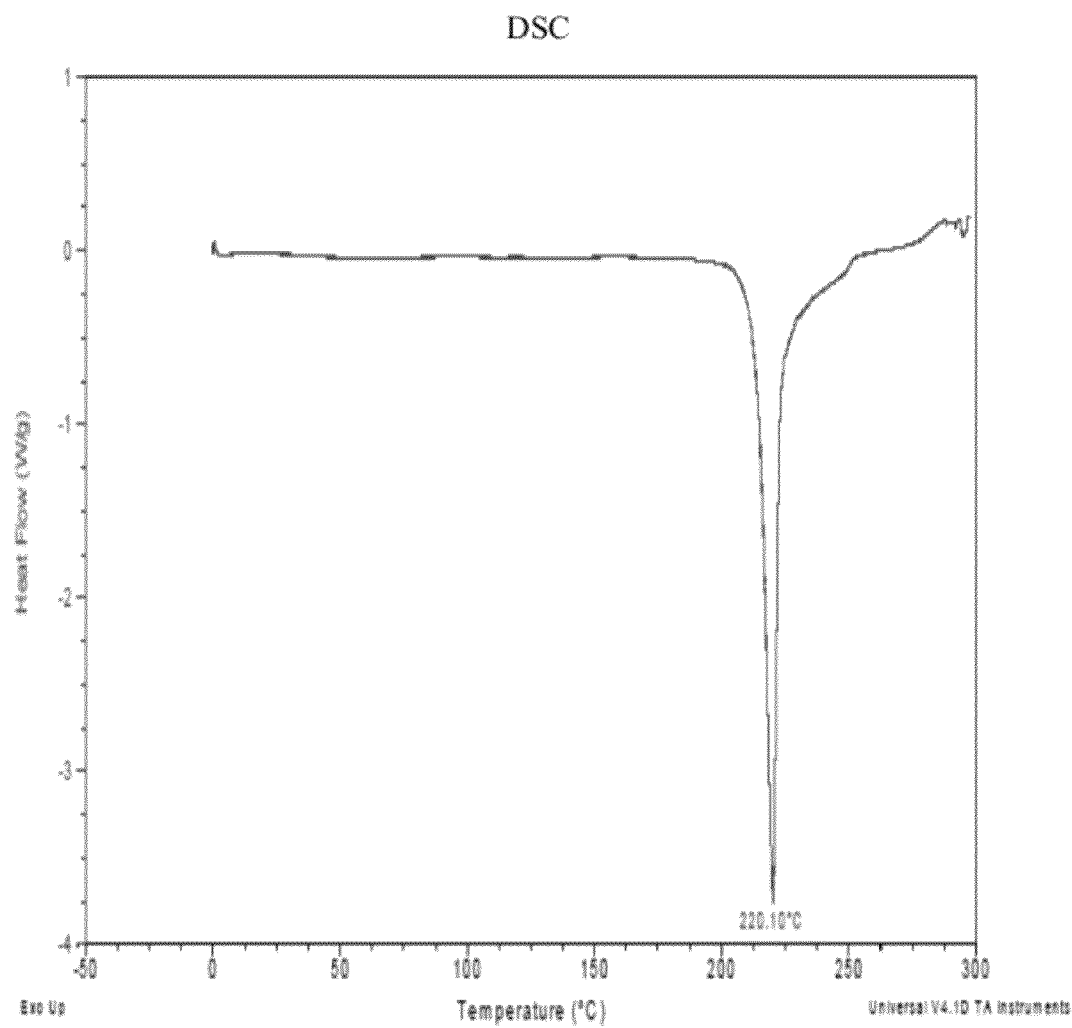
Figure 14 Representative DSC data collected for Form IIC

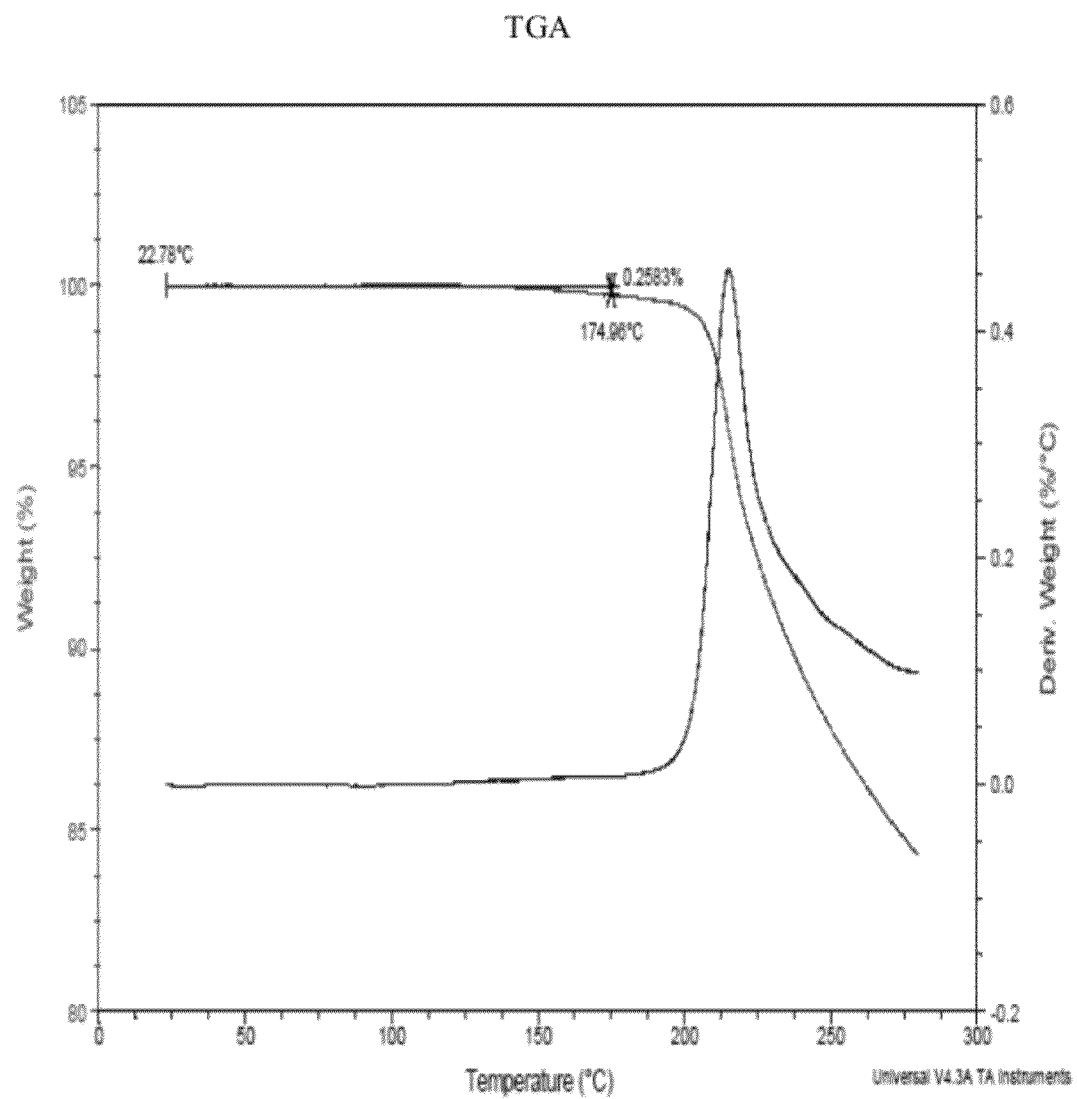
Figure 15 Representative TGA data collected for Form IIC

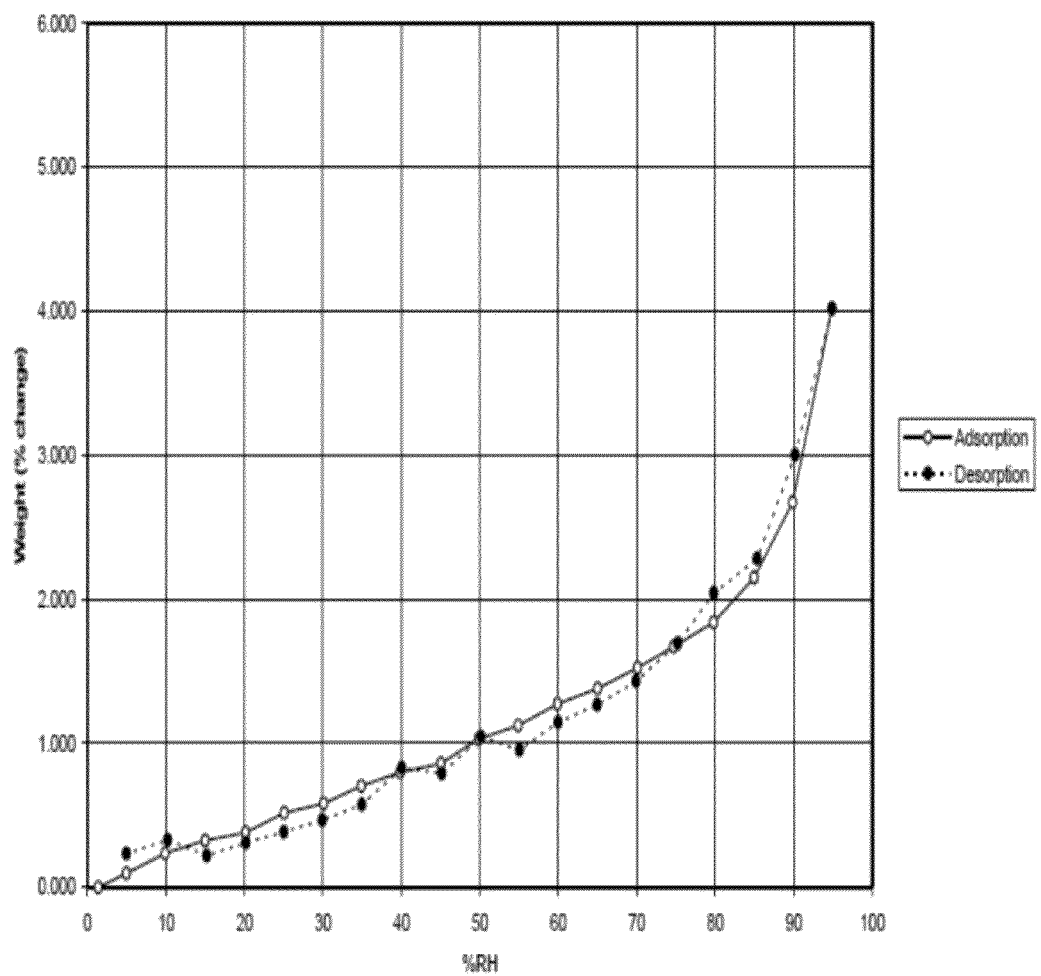
Figure 16   Representative Moisture Sorption Isotherm of Form IIC

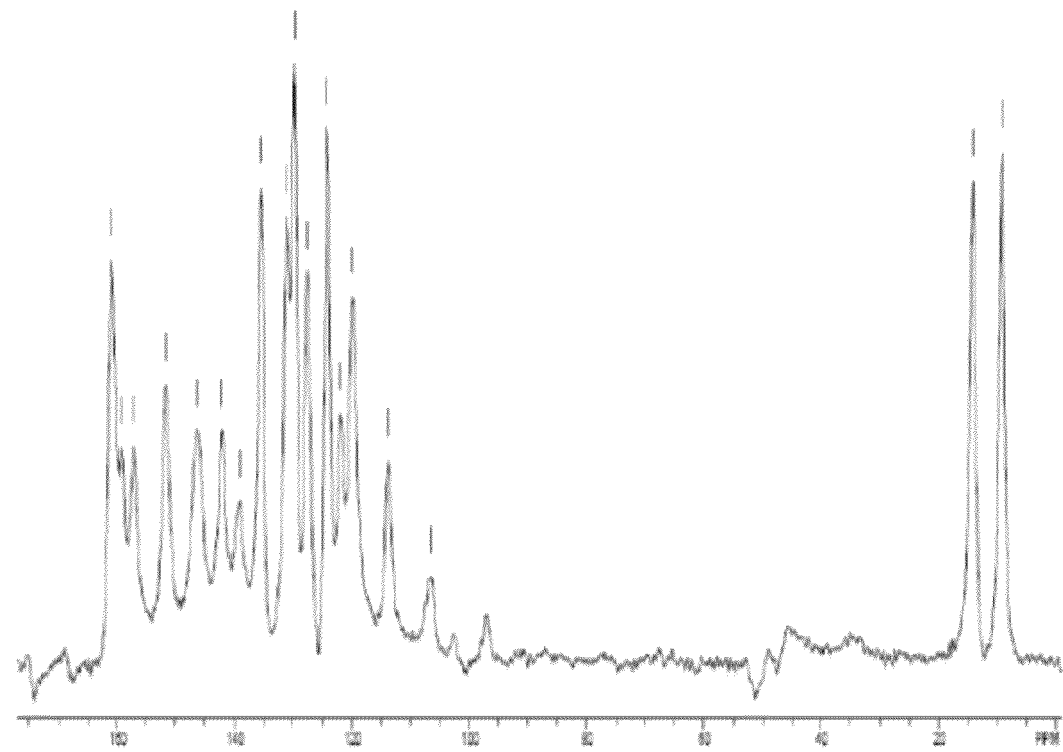
Figure 17  Representative SSNMR of Form IIC

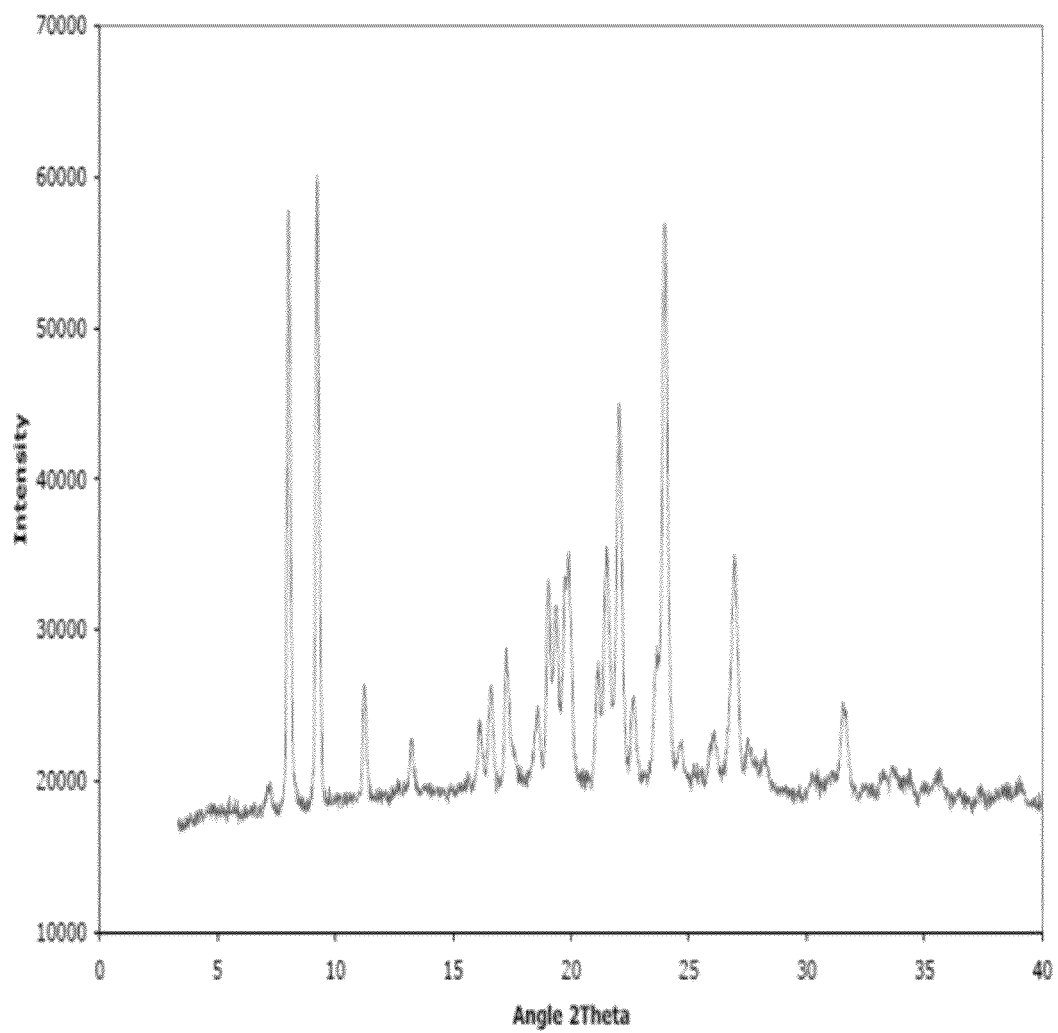
Figure 18 Representative XRPD of Form IID

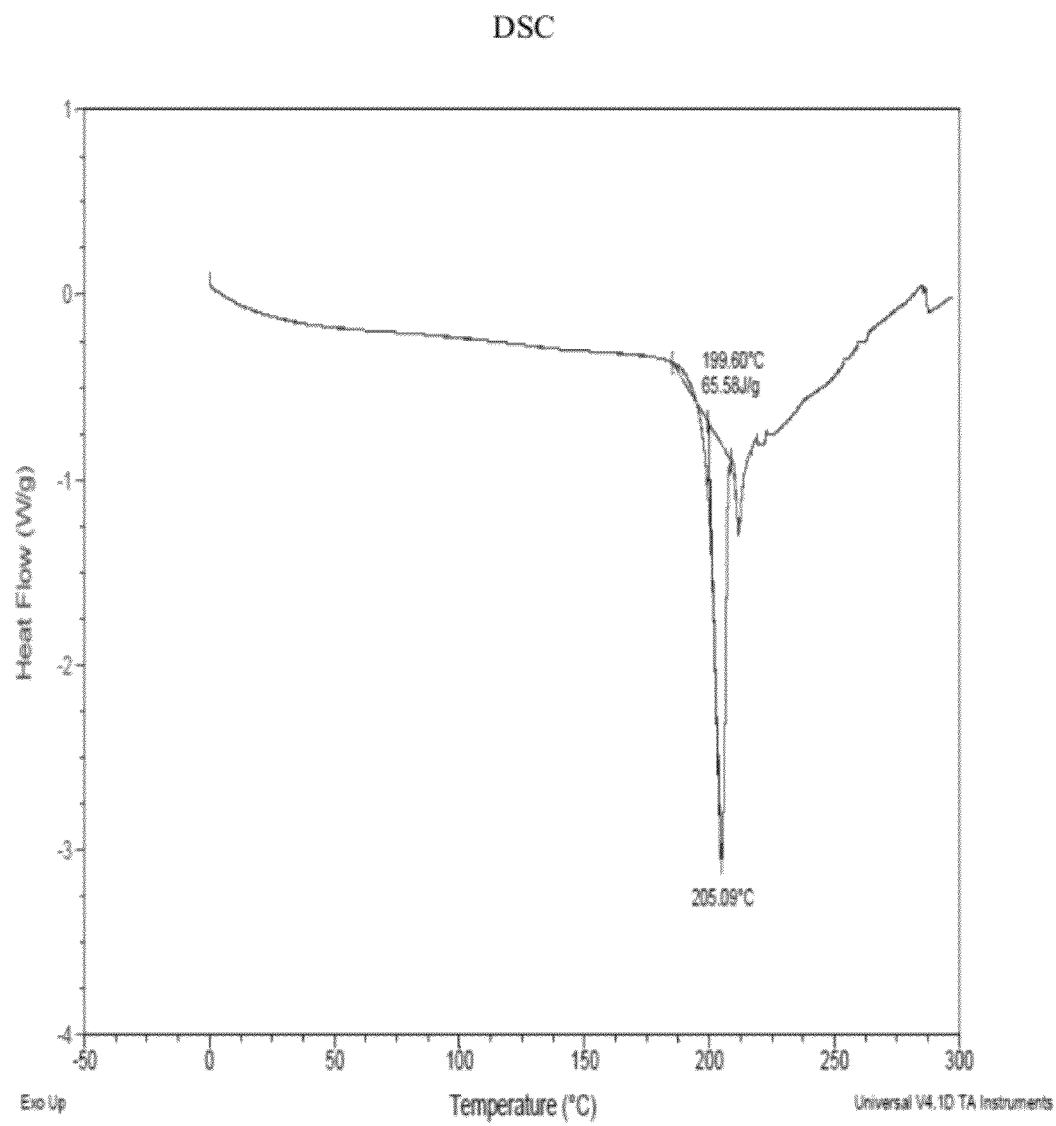
Figure 19  Representative DSC data collected for Form IID

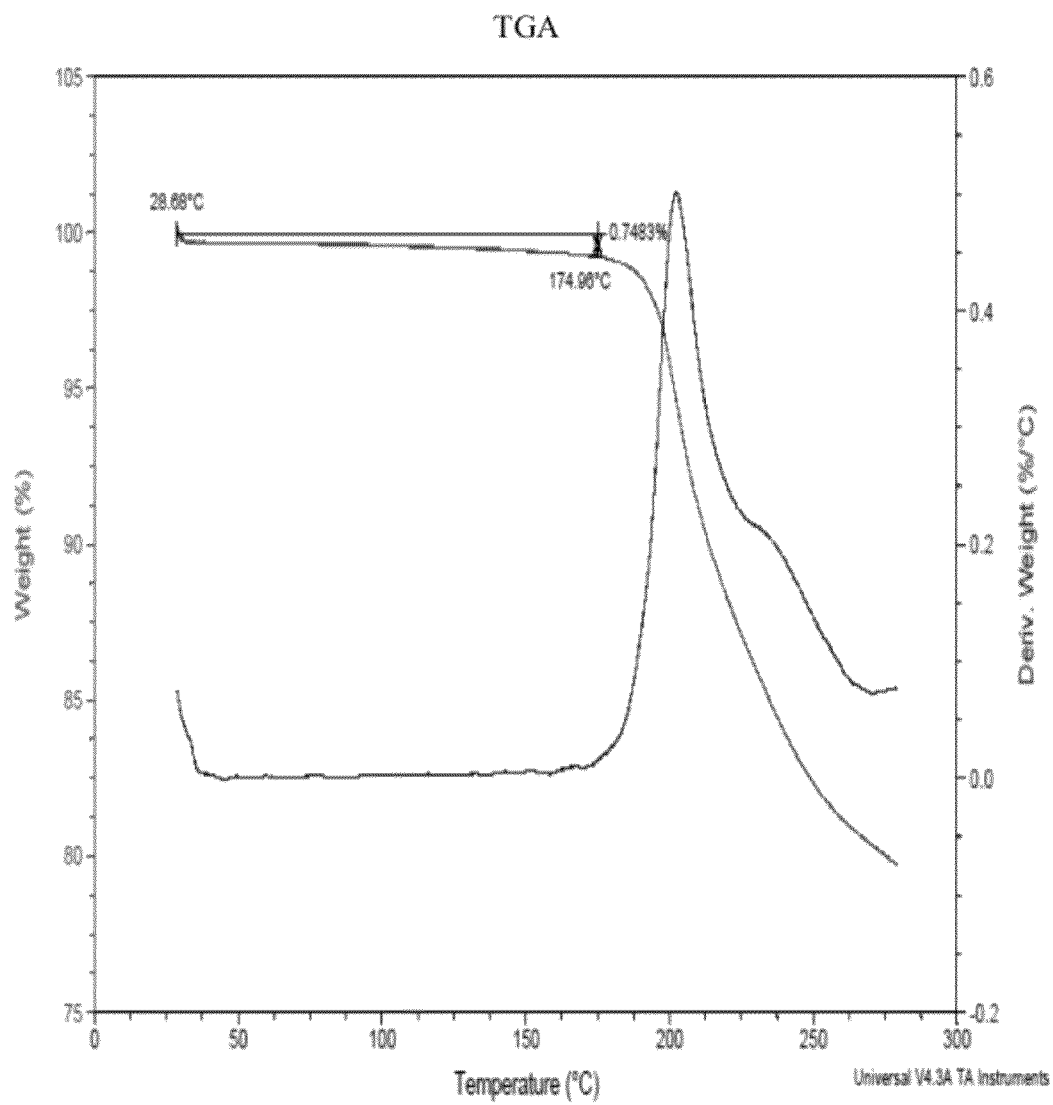
Figure 20  Representative TGA data collected for Form IID

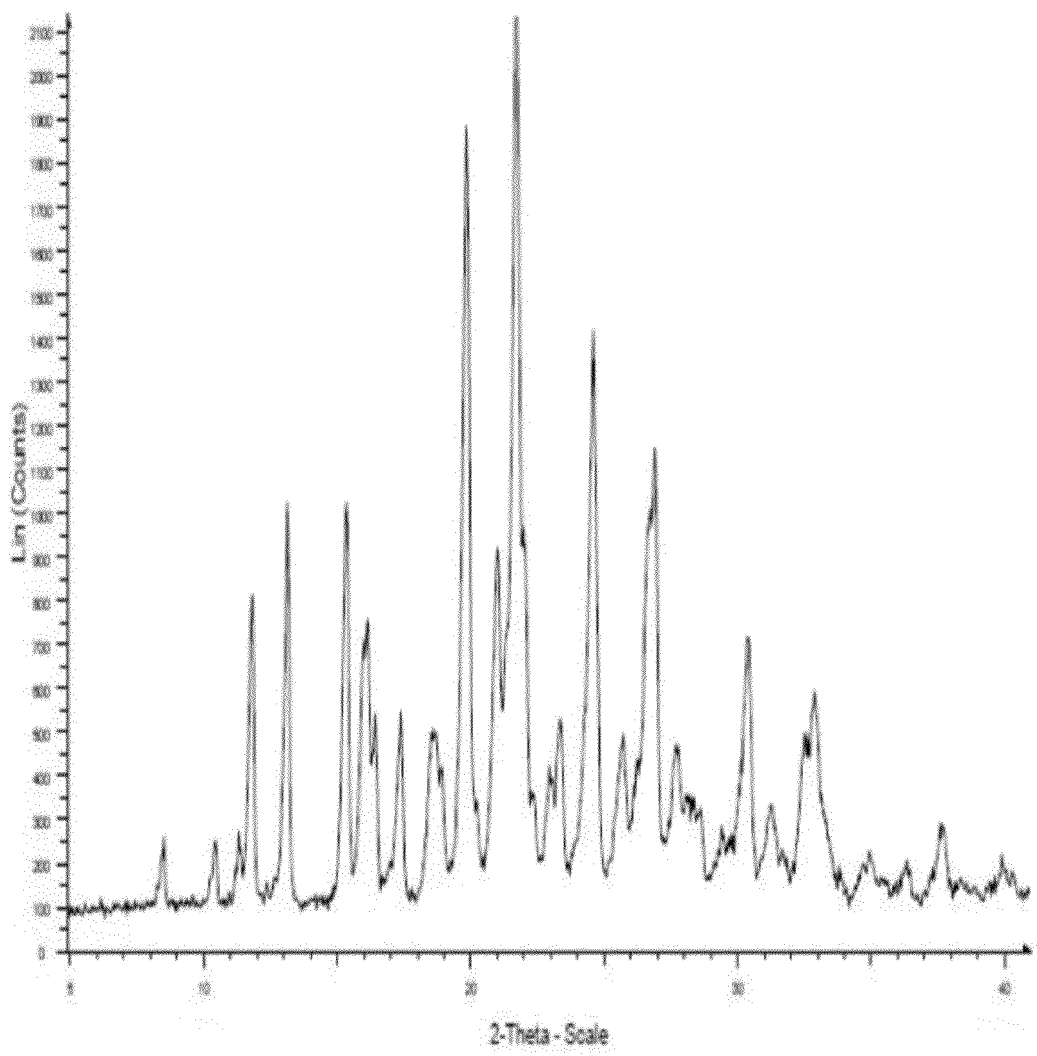
Figure 21  Representative XRPD data collected for Form IIIB

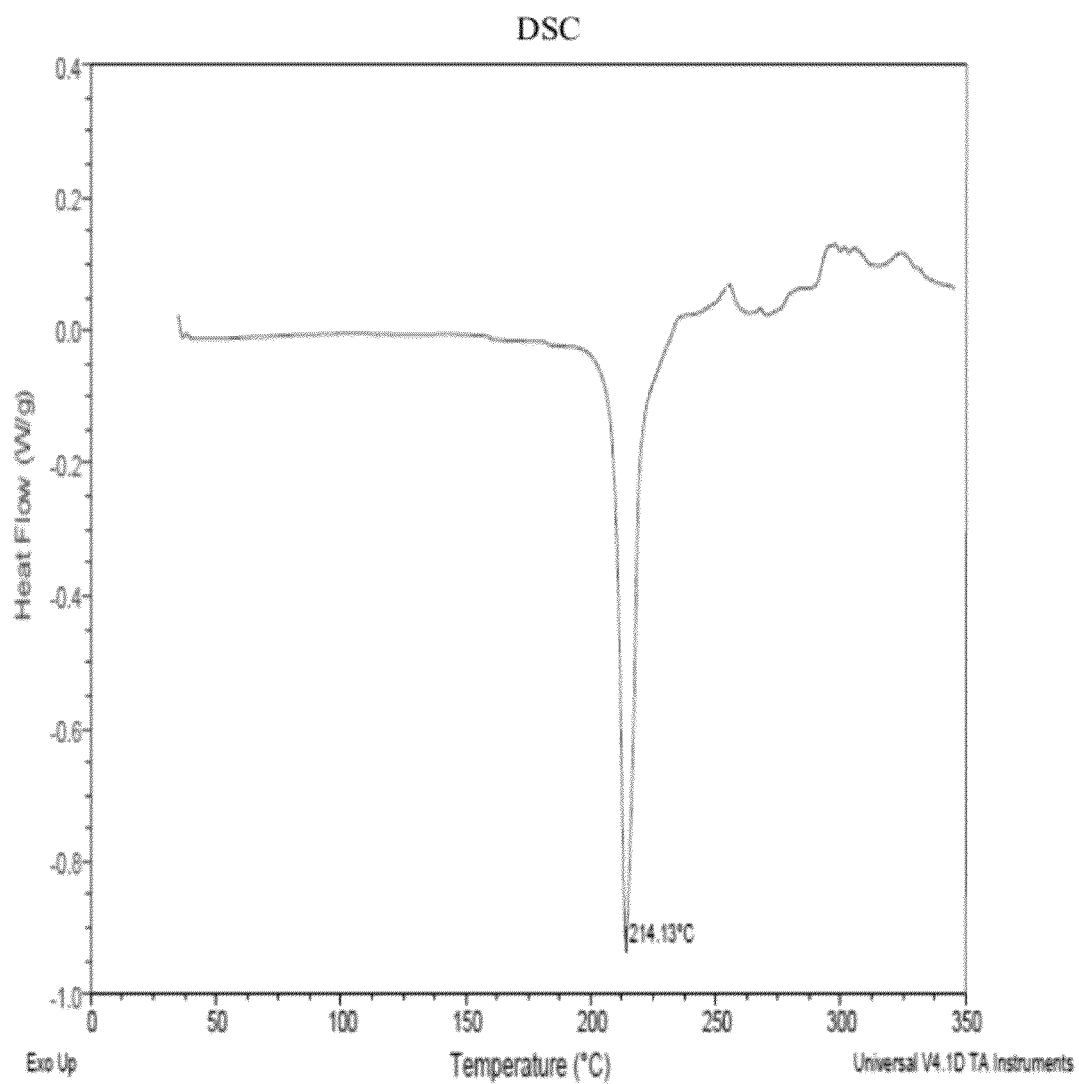
Figure 22  Representative DSC data collected for Form IIIB

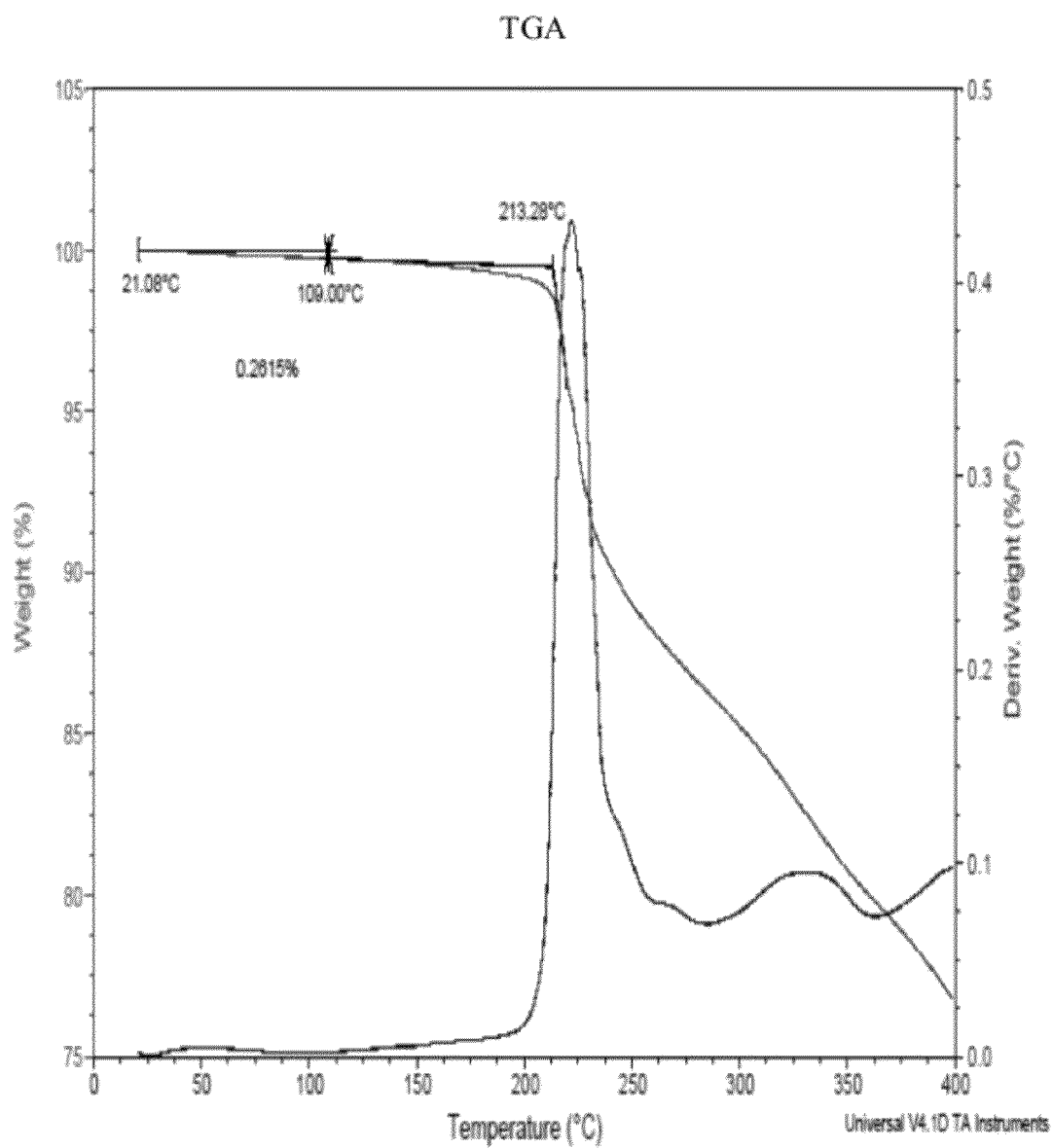
Figure 23  Representative TGA data collected for Form IIIB

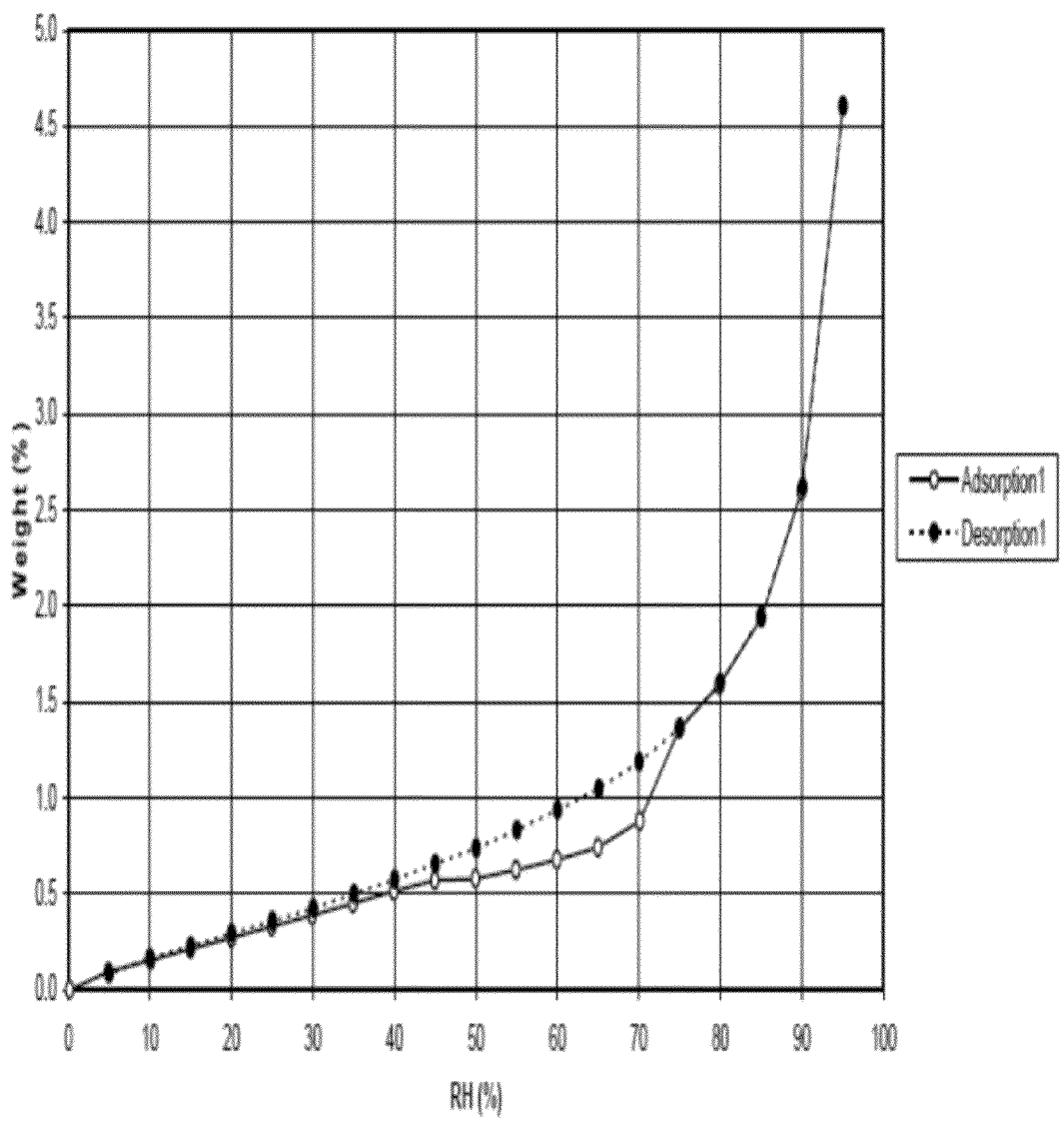
Figure 24   Representative Moisture Sorption Isotherm of Form IIIB

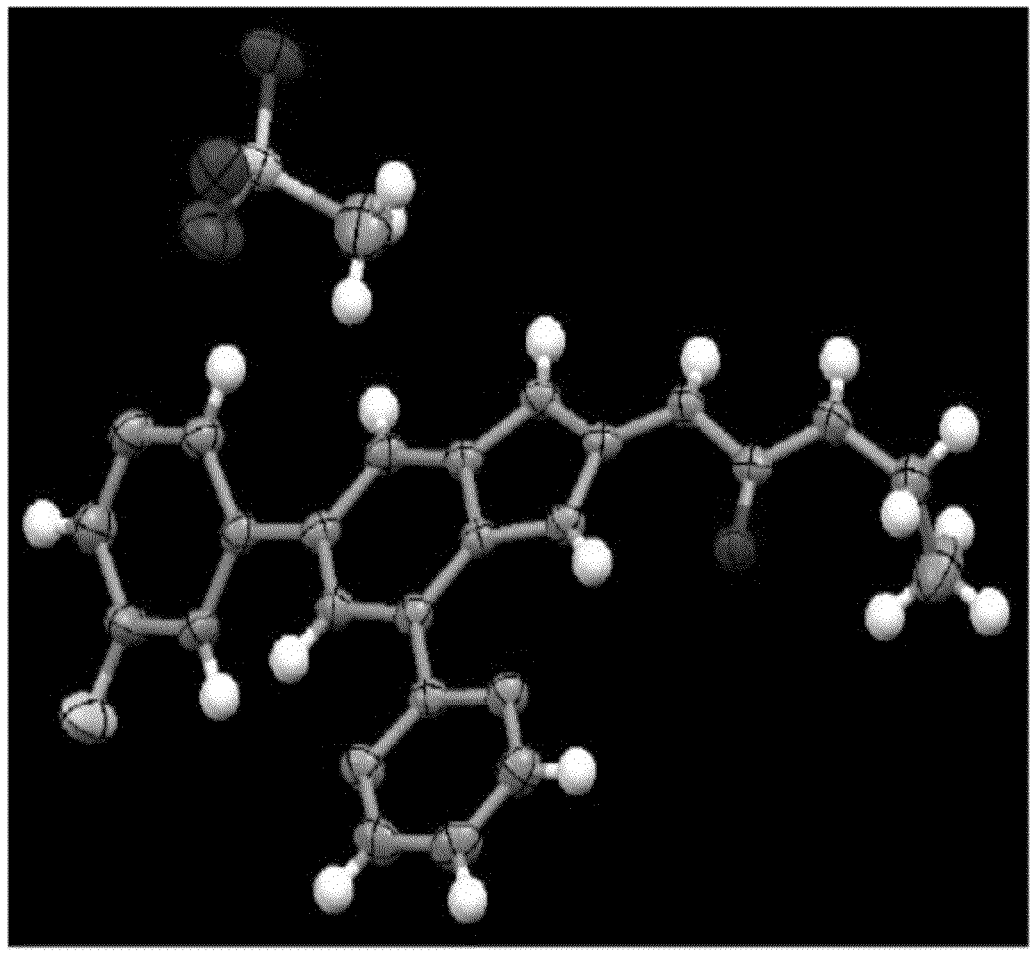
Figure 25  Crystal structure plot of Form IIIB

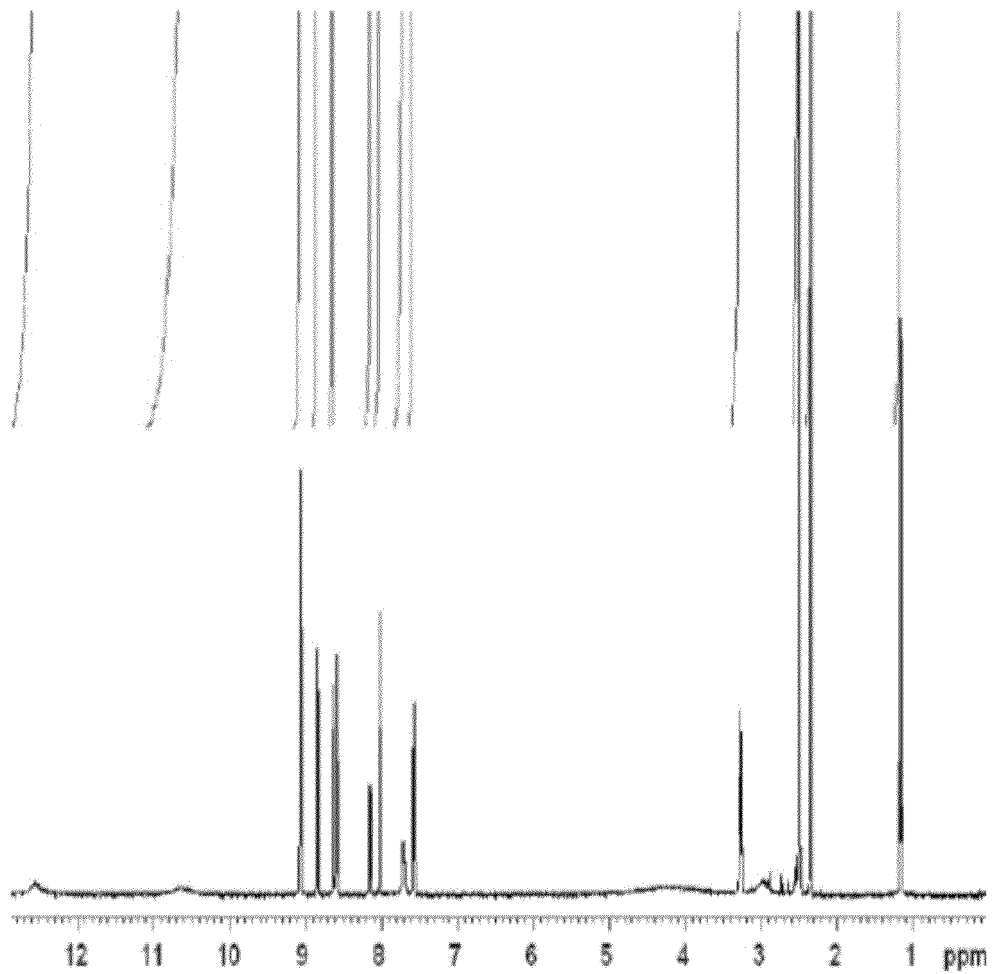
Figure 26 Representative solution ¹H NMR data collected for Form IIIB

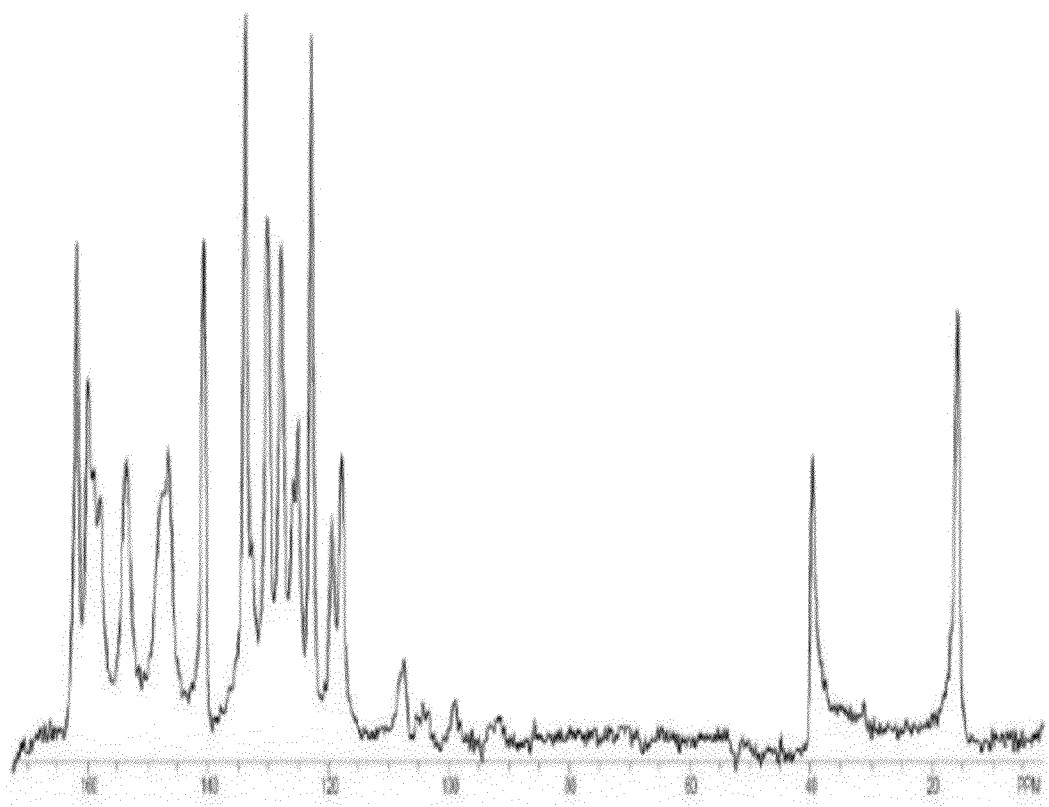
Figure 27 Representative ssNMR data collected for Form IIIB

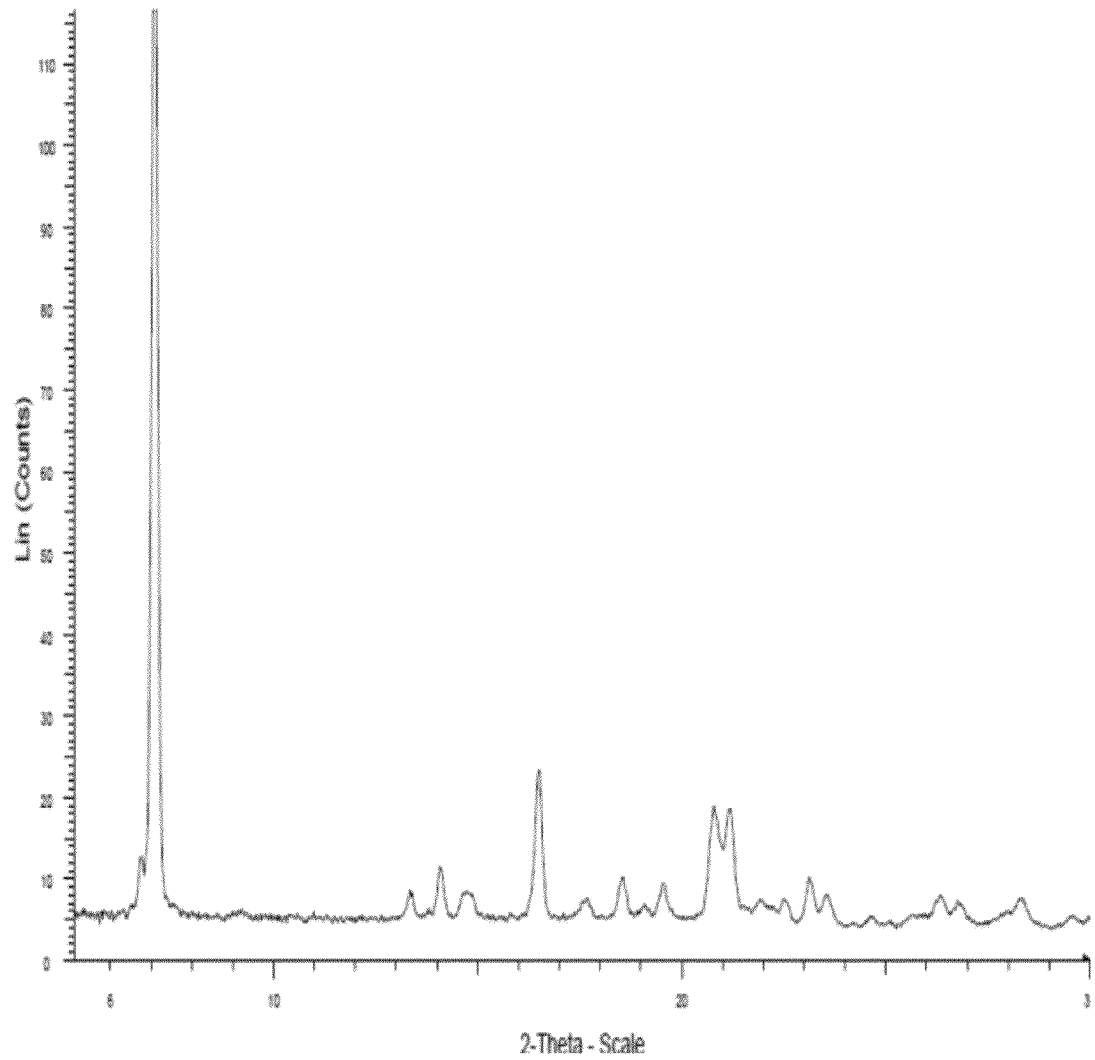
Figure 28  Representative XRPD data collected for Form IIIC

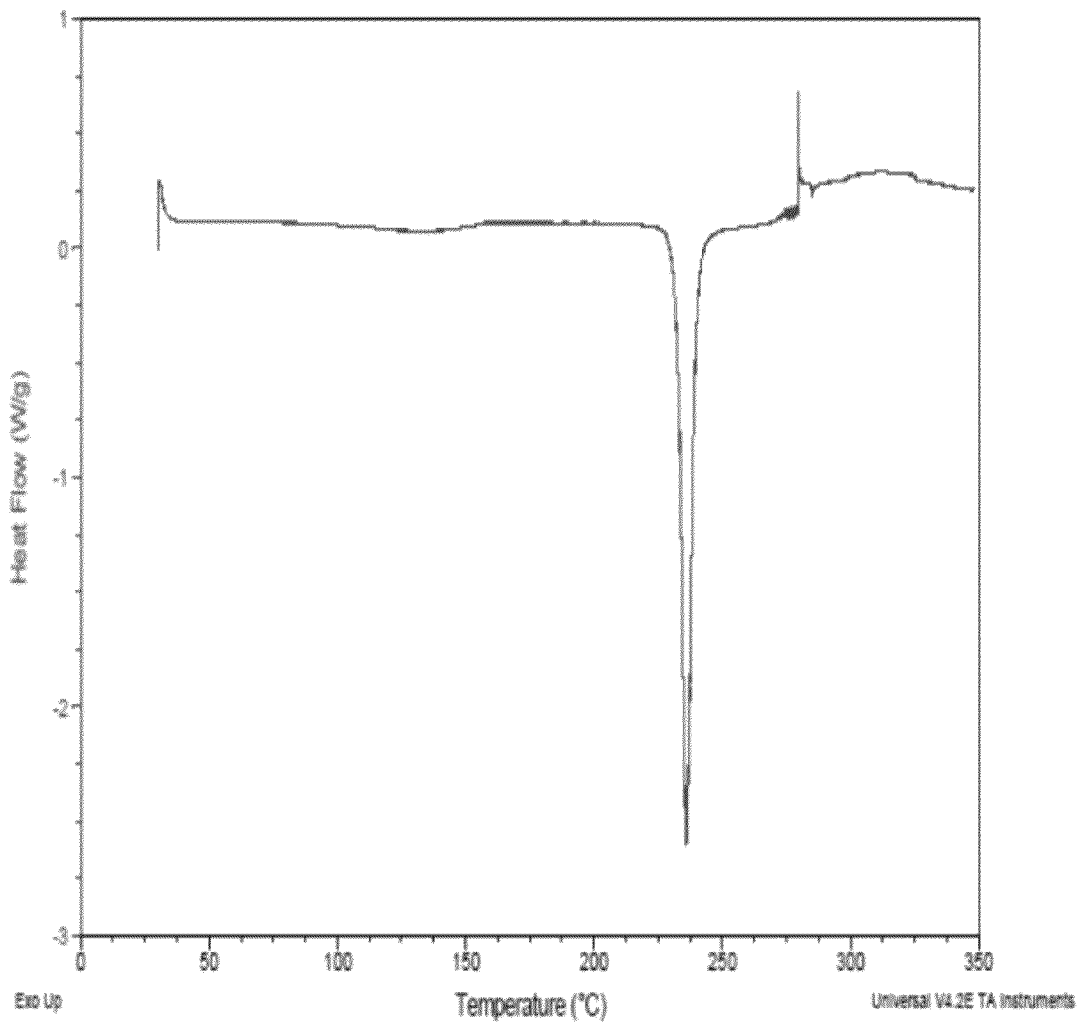
Figure 29  Representative DSC data collected for Form IIIC

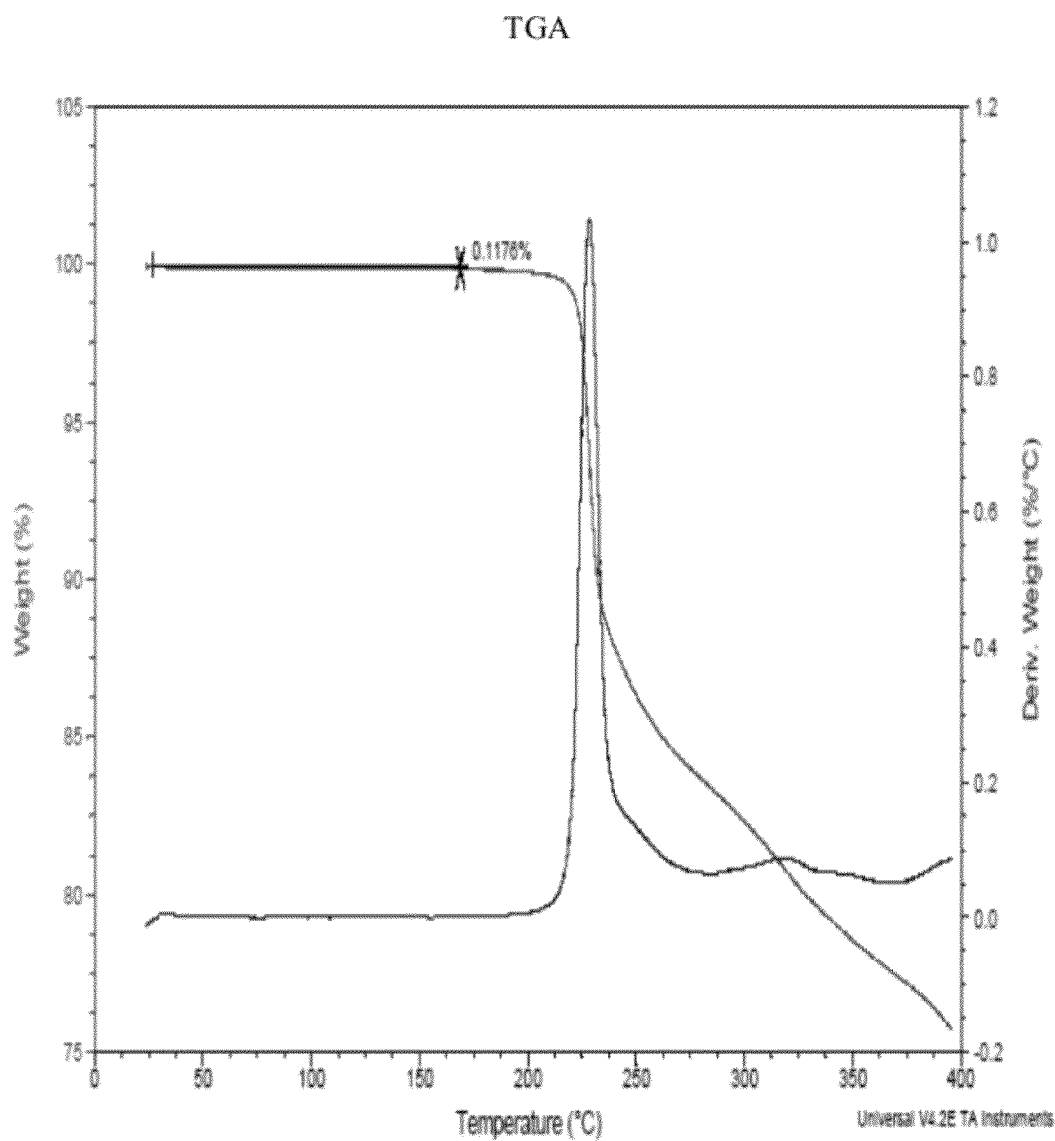
Figure 30  Representative TGA data collected for Form IIIC

SOLID FORMS OF 1-ETHYL-3-(5-(5-FLUOROPYRIDIN-3-YL)-7-(PYRIMIDIN-2-YL)-1H-BENZO[D]IMIDAZOL-2-YL)UREA

RELATED APPLICATIONS

This application claims the benefit of priority to U.S. Provisional Patent Application Ser. No. 61/012,355, filed Dec. 7, 2007.

TECHNICAL FIELD

This invention relates to solid forms of 1-ethyl-3-(5-(5-fluoropyridin-3-yl)-7-(pyrimidin-2-yl)-1H-benzo[d]imidazol-2-yl)urea and methods of use thereof.

BACKGROUND

Bacterial resistance to antibiotics has long been recognized, and it is today considered to be a serious worldwide health problem. As a result of resistance, some bacterial infections are either difficult to treat with antibiotics or even untreatable. This problem has become especially serious with the recent development of multiple drug resistance in certain strains of bacteria, such as *Streptococcus pneumoniae* (SP), *staphylococcus aureus*, *Mycobacterium tuberculosis*, and *Enterococcus*. As bacterial resistance to antibiotics has become an important public health problem, there is a continuing need to develop newer and more potent antibiotics. More particularly, there is a need for antibiotics that represent a new class of compounds not previously used to treat bacterial infection.

1-ethyl-3-(5-(5-fluoropyridin-3-yl)-7-(pyrimidin-2-yl)-1H-benzo[d]imidazol-2-yl)urea (Compound 1) having the structure below:

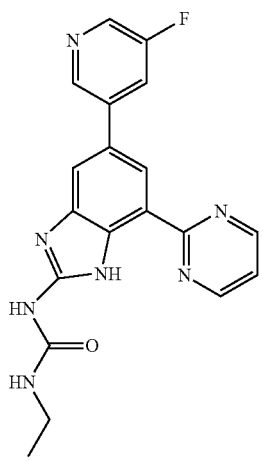

has demonstrated efficacy in the treatment of bacterial infections, including those resistant to one or more existing antibiotics. Compound 1 is described in US2005/0038247, published Feb. 15, 2005, US2006/0122196 published Jun. 8, 2006, and WO2006/022773 published Mar. 2, 2006, each of which is incorporated by reference herein in its entirety.

SUMMARY

Solid forms of Compound 1 are described herein. The properties of a solid relevant to its efficacy as a drug can be dependent on the form of the solid. For example, in a drug substance, variation in the solid form can lead to differences in properties such as dissolution rate, oral absorption, bioavailability, toxicology results and even clinical trial results. In some embodiments, the solid forms of Compound 1 are co-forms, for example, salts, solvates, co-crystals and hydrates of Compound 1.

Isotopically-labeled forms of Compound 1 wherein one or more atoms are replaced by an atom having an atomic mass or mass number different from the atomic mass or mass number usually found in nature are also included herein. Examples of isotopes that can be incorporated into compounds of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, and $^{17}O$. Such radio-labeled and stable-isotopically labeled compounds are useful, for example, as research or diagnostic tools or gyrase inhibitors with improved therapeutic profile.

In one aspect, the invention features crystalline 1-ethyl-3-(5-(5-fluoropyridin-3-yl)-7-(pyrimidin-2-yl)-1H-benzo[d]imidazol-2-yl)urea.

In one embodiment, the invention features crystalline 1-ethyl-3-(5-(5-fluoropyridin-3-yl)-7-(pyrimidin-2-yl)-1H-benzo[d]imidazol-2-yl)urea, characterized by one or more of the following peaks at 2θ degrees in an X-ray powder diffraction pattern: from about 6.2 to about 6.6 (e.g., about 6.4), from about 9.1 to about 9.5 (e.g., about 9.3), from about 12.6 to about 13.0 (e.g., about 12.8), from about 13.9 to about 14.3 (e.g., a bout 14.1), from about 15.2 to about 15.6 (e.g., about 15.4), from about 19.6 to about 20.0 (e.g., about 19.8), from about 20.2 to abut 20.6 (e.g., about 20.4), from about 20.5 to about 20.9 (e.g., about 20.7), from about 21.9 to about 22.3 (e.g., about 22.1), from about 24.0 to about 24.4 (e.g., about 24.2), from about 26.7 to about 27.1 (e.g., about 26.9), or from about 27.5 to about 27.9 (e.g., about 27.7). In one embodiment, the crystalline 1-ethyl-3-(5-(5-fluoropyridin-3-yl)-7-(pyrimidin-2-yl)-1H-benzo[d]imidazol-2-yl)urea is characterized by an X-ray powder diffraction pattern substantially similar to FIG. 2

In one embodiment, the crystalline 1-ethyl-3-(5-(5-fluoropyridin-3-yl)-7-(pyrimidin-2-yl)-1H-benzo[d]imidazol-2-yl)urea is characterized by a $T_m$ of about 270° C. as measured in DSC.

In one embodiment, the crystalline 1-ethyl-3-(5-(5-fluoropyridin-3-yl)-7-(pyrimidin-2-yl)-1H-benzo[d]imidazol-2-yl)urea is characterized by an 8% weight gain from 5% to 95% relative humidity at 25° C. as measured using DVS.

In one embodiment, the crystalline 1-ethyl-3-(5-(5-fluoropyridin-3-yl)-7-(pyrimidin-2-yl)-1H-benzo[d]imidazol-2-yl)urea has a solubility of at least 2 mg/ml at pH 1.

In one embodiment, the crystalline 1-ethyl-3-(5-(5-fluoropyridin-3-yl)-7-(pyrimidin-2-yl)-1H-benzo[d]imidazol-2-yl)urea remains in substantially the same physical form for at least about, 0.5, 2, 4, 6 months at 40° C./75% relative humidity. In another embodiment, the crystalline 1-ethyl-3-(5-(5-fluoropyridin-3-yl)-7-(pyrimidin-2-yl)-1H-benzo[d]imidazol-2-yl)urea is expected to remain in substantially the same physical form for at least about, 0.5, 2, 4, 6, 12, 18, 24 months at room temperature.

The term "room temperature," when used herein, means a temperature maintained thermostatically that encompasses the usual and the customary working environment of 19° C. to 25° C., which results in a mean kinetic temperature calculated to be no more than 25° C., and that allows for excursions from about 15° C. to about 30° C. An example of room temperature includes 22° C.+/−3° C., allowing for excursions from about 15° C. to about 30° C.

In one embodiment, the crystalline 1-ethyl-3-(5-(5-fluoropyridin-3-yl)-7-(pyrimidin-2-yl)-1H-benzo[d]imidazol-2- yl)urea remains in chemically stable form for at least about, 0.5, 2, 4, or 6 months at 40° C./75% relative humidity. In another embodiment, the crystalline 1-ethyl-3-(5-(5-fluoropyridin-3-yl)-7-(pyrimidin-2-yl)-1H-benzo[d]imidazol-2-yl)urea is expected to remain in chemically stable form for at least about, 0.5, 2, 4, 6, 12, 18, 24 months at room temperature.

In one embodiment, the crystalline 1-ethyl-3-(5-(5-fluoropyridin-3-yl)-7-(pyrimidin-2-yl)-1H-benzo[d]imidazol-2-yl)urea is characterized by one or more of the following peaks in a ss$^{13}$C-NMR pattern: about 162.3, about 158.8, about 157.0, about 149.5, about 142.0, about 137.5, about 136.0, about 131.8, about 125.9, about 119.3, about 114.7, about 35.9, or about 16.3. In one embodiment, the crystalline 1-ethyl-3-(5-(5-fluoropyridin-3-yl)-7-(pyrimidin-2-yl)-1H-benzo[d]imidazol-2-yl)urea is characterized by a ss$^{13}$C-NMR pattern substantially similar to FIG. 6.

In one aspect, the invention features a method of making crystalline 1-ethyl-3-(5-(5-fluoropyridin-3-yl)-7-(pyrimidin-2-yl)-1H-benzo[d]imidazol-2-yl)urea, the method comprising precipitating 1-ethyl-3-(5-(5-fluoropyridin-3-yl)-7-(pyrimidin-2-yl)-1H-benzo[d]imidazol-2-yl)urea from an aqueous solution.

In one aspect, the invention features 1-ethyl-3-(5-(5-fluoropyridin-3-yl)-7-(pyrimidin-2-yl)-1H-benzo[d]imidazol-2-yl)urea.monoesylate.

In one embodiment, the invention features crystalline 1-ethyl-3-(5-(5-fluoropyridin-3-yl)-7-(pyrimidin-2-yl)-1H-benzo[d]imidazol-2-yl)urea.monoesylate.

In one embodiment, the crystalline 1-ethyl-3-(5-(5-fluoropyridin-3-yl)-7-(pyrimidin-2-yl)-1H-benzo[d]imidazol-2-yl)urea.monoesylate has an aqueous solubility of greater than 150 mg/ml at pH 1.6.

In one embodiment, the crystalline 1-ethyl-3-(5-(5-fluoropyridin-3-yl)-7-(pyrimidin-2-yl)-1H-benzo[d]imidazol-2-yl)urea.monoesylate is characterized by one or more of the following peaks at 2θ degrees in an X-ray powder diffraction pattern: from about 6.3 to about 6.7 (e.g., about 6.5), from about 7.0 to about 7.4 (e.g., about 7.2), from about 12.4 to about 12.8 (e.g., about 12.6), from about 14.2 to about 14.6 (e.g., about 14.4), from about 15.4 to about 15.8 (e.g., about 15.6), from about 18.4 to about 18.8 (e.g., about 18.6), from about 19.4 to about 19.8 (e.g., about 19.6), from about 21.5 to about 21.9 (e.g., about 21.7), from about 22.4 to about 22.8 (e.g., about 22.6, from about 25.2 to about 25.6 (e.g., about 25.4), or from about 26.9 to about 27.3 (e.g., about 27.1).

In one embodiment, the crystalline 1-ethyl-3-(5-(5-fluoropyridin-3-yl)-7-(pyrimidin-2-yl)-1H-benzo[d]imidazol-2-yl)urea.monoesylate is characterized by an X-ray powder diffraction pattern substantially similar to FIG. 7.

In one embodiment, the crystalline 1-ethyl-3-(5-(5-fluoropyridin-3-yl)-7-(pyrimidin-2-yl)-1H-benzo[d]imidazol-2-yl)urea.monoesylate is characterized by a $T_m$ of about 216° C. as measured by DSC.

In one embodiment, the crystalline 1-ethyl-3-(5-(5-fluoropyridin-3-yl)-7-(pyrimidin-2-yl)-1H-benzo[d]imidazol-2-yl)urea.monoesylate is characterized by an 11% weight gain from 5% to 95% relative humidity at 25° C.

In one embodiment, the crystalline 1-ethyl-3-(5-(5-fluoropyridin-3-yl)-7-(pyrimidin-2-yl)-1H-benzo[d]imidazol-2-yl)urea.monoesylate is characterized by one or more of the following peaks at 2θ degrees in an X-ray powder diffraction pattern: from about 6.0 to about 6.4 (e.g., about 6.2), from about 7.2 to about 7.6 (e.g., about 7.4), from about 7.9 to about 8.3 (e.g., about 8.1), from about 12.2 to about 12.6 (e.g., about 12.4), from about 13.0 to about 13.4 (e.g., about 13.2), from about 14.3 to about 14.7 (e.g., about 14.5), from about 16.1 to about 16.5 (e.g., about 16.3), from about 16.9 to about 17.3 (e.g., about 17.1), from about 17.6 to about 18.0 (e.g., about 17.8), from about 18.4 to about 18.8 (e.g., about 18.6), from about 19.6 to about 20.0 (e.g., about 19.8), from about 20.8 to about 21.2 (e.g., about 21.0), from about 21.3 to about 21.7 (e.g., about 21.5), from about 22.7 to about 23.1 (e.g., about 22.9), from about 24.8 to about 25.2 (e.g., about 25.0), from about 25.8 to about 26.2 (e.g., about 26.0), from about 27.0 to about 27.4 (e.g., about 27.2), or from about 27.7 to about 28.1 (e.g., about 27.9). In one embodiment, the crystalline 1-ethyl-3-(5-(5-fluoropyridin-3-yl)-7-(pyrimidin-2-yl)-1H-benzo[d]imidazol-2-yl)urea.monoesylate is characterized by an X-ray powder diffraction pattern substantially similar to FIG. 11.

In one embodiment, the crystalline 1-ethyl-3-(5-(5-fluoropyridin-3-yl)-7-(pyrimidin-2-yl)-1H-benzo[d]imidazol-2-yl)urea.monoesylate is characterized by a $T_m$ of from 214° C. to 216° C. when measured by DSC.

In one embodiment, the crystalline 1-ethyl-3-(5-(5-fluoropyridin-3-yl)-7-(pyrimidin-2-yl)-1H-benzo[d]imidazol-2-yl)urea.monoesylate remains in substantially the same physical form for at least about 2 weeks at 40° C./75% relative humidity.

In one embodiment, the crystalline 1-ethyl-3-(5-(5-fluoropyridin-3-yl)-7-(pyrimidin-2-yl)-1H-benzo[d]imidazol-2-yl)urea.monoesylate remains chemically stable for at least about 2 weeks at 40° C./75% relative humidity.

In one embodiment, the crystalline 1-ethyl-3-(5-(5-fluoropyridin-3-yl)-7-(pyrimidin-2-yl)-1H-benzo[d]imidazol-2-yl)urea.monoesylate is characterized by one or more of the following peaks at 2θ degrees in an X-ray powder diffraction pattern: from about 8.0 to about 8.4 (e.g., about 8.2), from about 9.4 to about 9.8 (e.g., about 9.6), from about 10.1 to about 10.5 (e.g., about 10.3), from about 12.2 to about 12.6 (e.g., about 12.4), from about 16.3 to about 16.7 (e.g., about 16.5), from about 18.2 to about 18.6 (e.g., about 18.4), from about 20.2 to about 20.6 (e.g., about 20.4), from about 22.0 to about 22.4 (e.g., about 22.2), from about 24.6 to about 25.0 (e.g., about 24.8), or from about 25.8 to about 26.2 (e.g., about 26.0). In one embodiment, the crystalline 1-ethyl-3-(5-(5-fluoropyridin-3-yl)-7-(pyrimidin-2-yl)-1H-benzo[d]imidazol-2-yl)urea.monoesylate is characterized by an X-ray powder diffraction pattern substantially similar to FIG. 13.

In one embodiment, the crystalline 1-ethyl-3-(5-(5-fluoropyridin-3-yl)-7-(pyrimidin-2-yl)-1H-benzo[d]imidazol-2-yl)urea.monoesylate is characterized by a $T_m$ of from 216° C. to 220° C. as measured using DSC.

In one embodiment, the crystalline 1-ethyl-3-(5-(5-fluoropyridin-3-yl)-7-(pyrimidin-2-yl)-1H-benzo[d]imidazol-2-yl)urea.monoesylate is characterized by a weight gain of about 4% from 5% to 95% relative humidity at 25° C.

In one embodiment, the crystalline 1-ethyl-3-(5-(5-fluoropyridin-3-yl)-7-(pyrimidin-2-yl)-1H-benzo[d]imidazol-2-yl)urea.monoesylate remains in substantially the same physical form for at least about 6 months at 40° C./75% relative humidity.

In one embodiment, the crystalline 1-ethyl-3-(5-(5-fluoropyridin-3-yl)-7-(pyrimidin-2-yl)-1H-benzo[d]imidazol-2-yl)urea.monoesylate is characterized by one or more of the following peaks in a ss$^{13}$C-NMR pattern: about 161.7, about 159.9, about 157.9, about 153.6, about 146.5, about 140.6, about 133.8, about 132.6, about 130.0, about 127.9, about 125.8, about 125.0, about 122.8, about 119.4, about 117.8, about 107.4, about 39.5, about 38.0, or about 15.8. In one embodiment, the crystalline 1-ethyl-3-(5-(5-fluoropyridin-3- yl)-7-(pyrimidin-2-yl)-1H-benzo[d]imidazol-2-yl)urea.monoesylate is characterized by a ss$^{13}$C-NMR pattern substantially similar to FIG. 17.

In one embodiment, the crystalline 1-ethyl-3-(5-(5-fluoropyridin-3-yl)-7-(pyrimidin-2-yl)-1H-benzo[d]imidazol-2-yl)urea.monoesylate is characterized by one or more of the following peaks at 2θ degrees in an X-ray powder diffraction pattern: from about 7.8 to about 8.2 (e.g., about 8.0), from about 9.1 to about 9.5 (e.g., about 9.3), from about 11.1 to about 11.5 (e.g., about 11.3), from about 13.0 to about 13.4 (e.g., about 13.2), from about 15.9 to about 16.3 (e.g., about 16.1), from about 16.4 to about 16.8 (e.g., about 16.6), from about 17.1 to about 17.5 (e.g., about 17.3), from about 18.8 to about 19.2 (e.g., about 19.0), from about 19.2 to about 19.6 (e.g., about 19.4), from about 19.6 to about 20.0 (e.g., about 19.8), from about 21.0 to about 21.4 (e.g., about 21.2), from about 21.3 to about 21.7 (e.g., about 21.5), from about 21.9 to about 22.3 (e.g., about 22.1), from about 23.8 to about 24.2 (e.g., about 24.0), or from about 26.7 to about 27.1 (e.g., about 26.9).

In one embodiment, the crystalline 1-ethyl-3-(5-(5-fluoropyridin-3-yl)-7-(pyrimidin-2-yl)-1H-benzo[d]imidazol-2-yl)urea.monoesylate is characterized by an X-ray powder diffraction pattern substantially similar to FIG. 18.

In one embodiment, the crystalline 1-ethyl-3-(5-(5-fluoropyridin-3-yl)-7-(pyrimidin-2-yl)-1H-benzo[d]imidazol-2-yl)urea.monoesylate is characterized by a $T_m$ of 205° C. as measured using DSC.

In one aspect, the invention features 1-ethyl-3-(5-(5-fluoropyridin-3-yl)-7-(pyrimidin-2-yl)-1H-benzo[d]imidazol-2-yl)urea.monomesylate.

In one aspect, the invention features crystalline 1-ethyl-3-(5-(5-fluoropyridin-3-yl)-7-(pyrimidin-2-yl)-1H-benzo[d]imidazol-2-yl)urea.monomesylate.

In one embodiment, the crystalline 1-ethyl-3-(5-(5-fluoropyridin-3-yl)-7-(pyrimidin-2-yl)-1H-benzo[d]imidazol-2-yl)urea.monomesylate is characterized by one or more of the following peaks at 2θ degrees in an X-ray powder diffraction pattern: from about 8.5 to about 8.9 (e.g., about 8.7), from about 10.4 to about 10.8 (e.g., about 10.6), from about 11.4 to about 11.8 (e.g., about 11.6), from about 11.8 to about 12.2 (e.g., about 12.0), from about 13.2 to about 13.6 (e.g., about 13.4), from about 15.4 to about 15.8 (e.g., about 15.6), from about 16.2 to about 16.6 (e.g., about 16.4), from about 17.5 to about 17.9 (e.g., about 17.7), from about 19.9 to about 20.3 (e.g., about 20.1), from about 21.0 to about 21.4 (e.g., about 21.2), from about 21.7 to about 22.1 (e.g., about 21.9), from about 24.5 to about 24.9 (e.g., about 24.7), from about 26.8 to about 27.2 (e.g., about 27.0), from about 30.3 to about 30.7 (e.g., about 30.5), or from about 32.8 to about 33.2 (e.g., about 33.0). In one embodiment, the crystalline 1-ethyl-3-(5-(5-fluoropyridin-3-yl)-7-(pyrimidin-2-yl)-1H-benzo[d]imidazol-2-yl)urea.monomesylate is characterized by an X-ray powder diffraction pattern substantially similar to FIG. 21.

In one embodiment, the crystalline 1-ethyl-3-(5-(5-fluoropyridin-3-yl)-7-(pyrimidin-2-yl)-1H-benzo[d]imidazol-2-yl)urea.monomesylate is characterized by a $T_m$ of 215° C. as measured using DSC.

In one embodiment, the crystalline 1-ethyl-3-(5-(5-fluoropyridin-3-yl)-7-(pyrimidin-2-yl)-1H-benzo[d]imidazol-2-yl)urea.monomesylate is characterized by a weight gain of 4.6% from 5% to 95% relative humidity at 25° C.

In one embodiment, the crystalline 1-ethyl-3-(5-(5-fluoropyridin-3-yl)-7-(pyrimidin-2-yl)-1H-benzo[d]imidazol-2-yl)urea.monomesylate is characterized by an aqueous solubility of greater than 12 mg/ml at pH 4.4.

In one embodiment, the crystalline 1-ethyl-3-(5-(5-fluoropyridin-3-yl)-7-(pyrimidin-2-yl)-1H-benzo[d]imidazol-2-yl)urea.monomesylate remains in substantially the same physical form for at least 1 month at 40° C./75% relative humidity.

In one embodiment, the crystalline 1-ethyl-3-(5-(5-fluoropyridin-3-yl)-7-(pyrimidin-2-yl)-1H-benzo[d]imidazol-2-yl)urea.monomesylate remains chemically stable for at least 1 month at 40° C./75% relative humidity.

In one embodiment, the crystalline 1-ethyl-3-(5-(5-fluoropyridin-3-yl)-7-(pyrimidin-2-yl)-1H-benzo[d]imidazol-2-yl)urea.monomesylate is characterized by one or more of the following peaks in ppm in a ss$^{13}$C-NMR pattern: about 161.7, about 159.9, about 157.9, about 153.6, about 146.5, about 140.6, about 133.8, about 132.6, about 130.0, about 127.9, about 125.8, about 125.0, about 122.8, about 119.4, about 117.8, about 107.4, about 39.5, about 38.0, or about 15.8. In one embodiment, the crystalline 1-ethyl-3-(5-(5-fluoropyridin-3-yl)-7-(pyrimidin-2-yl)-1H-benzo[d]imidazol-2-yl)urea.monomesylate is characterized by a ss$^{13}$C-NMR pattern substantially similar to FIG. 27.

In one embodiment, the crystalline 1-ethyl-3-(5-(5-fluoropyridin-3-yl)-7-(pyrimidin-2-yl)-1H-benzo[d]imidazol-2-yl)urea.monomesylate has a $P2_1/n$ space grouping.

In one embodiment, the crystalline 1-ethyl-3-(5-(5-fluoropyridin-3-yl)-7-(pyrimidin-2-yl)-1H-benzo[d]imidazol-2-yl)urea.monomesylate has the following unit cell dimensions:

a=14.3 Å
b=8.8 Å
c=17.0 Å.

In one embodiment, the crystalline 1-ethyl-3-(5-(5-fluoropyridin-3-yl)-7-(pyrimidin-2-yl)-1H-benzo[d]imidazol-2-yl)urea.monomesylate is characterized by one or more of the following peaks at 2θ degrees in an X-ray powder diffraction pattern: from about 6.8 to about 7.2 (e.g., about 7.0); from about 13.1 to about 13.5 (e.g., about 13.3), from about 13.9 to about 14.3 (e.g., about 14.1), from about 14.5 to about 14.9 (e.g., about 14.7), from about 16.3 to about 16.7 (e.g., about 16.5), from about 18.3 to about 18.7 (e.g., about 18.5), from about 19.3 to about 19.7 (e.g., about 19.5), from about 20.6 to about 21.0 (e.g., about 20.8), from about 21.0 to about 21.4 (e.g., about 21.2), from about 22.9 to about 23.3 (e.g., about 23.1), or from about 23.4 to about 23.8 (e.g., about 23.6). In one embodiment, the crystalline 1-ethyl-3-(5-(5-fluoropyridin-3-yl)-7-(pyrimidin-2-yl)-1H-benzo[d]imidazol-2-yl)urea.monomesylate is characterized by an X-ray powder diffraction pattern substantially similar to FIG. 28.

In one embodiment, the crystalline 1-ethyl-3-(5-(5-fluoropyridin-3-yl)-7-(pyrimidin-2-yl)-1H-benzo[d]imidazol-2-yl)urea.monomesylate is characterized by a $T_m$ of 235° C. when measured using DSC.

In one aspect, the invention features a composition (or pharmaceutical composition) wherein essentially all of the Compound 1 is in a first form disclosed herein, e.g., form IA, IIA, IIB, IIC, IID, IIIB, or IIIC, determined, e.g., by evaluating physical, chemical or biological parameters disclosed herein.

In one aspect, the invention features a composition (or pharmaceutical composition) comprising a first solid form of the Compound 1, e.g., form IA, IIA, IIB, IIC, IID, IIIB, or IIIC, determined, e.g., by evaluating physical, chemical or biological parameters disclosed herein and a second form of Compound 1, e.g., form IA, IIA, IIB, IIC, IID, IIIB, or IIIC, determined, e.g., by evaluating physical, chemical or biological parameters disclosed herein. In some embodiments, the first and second forms comprise at least one homogenous portion, i.e., regions enriched for one of the forms e.g., form IA, IIA, IIB, IIC, IID, IIIB, or IIIC. In some embodiments, the first and second forms are heterogeneous within the composition.

In one aspect, the invention features a pharmaceutical composition comprising a solid form of 1-ethyl-3-(5-(5-fluoropyridin-3-yl)-7-(pyrimidin-2-yl)-1H-benzo[d]imidazol-2-yl) urea described herein (e.g., form IA, IIA, IIB, IIC, IID, IIIB, or IIIC) and a pharmaceutically acceptable excipient. In some embodiments, the composition is an aqueous solution. In some embodiments, the composition comprises a solid. In some embodiments, the composition is an oral suspension. In some embodiments, the composition is a solid oral dosage form (e.g., a tablet or capsule).

In some embodiments, the composition comprises one or more additional therapeutic agents. In some embodiments the additional therapeutic agent is an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

In some embodiments, the additional therapeutic agent or agents is an antibiotic selected from a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a tetracycline, a glycopeptide, a streptogramin, an oxazolidinone, a rifamycin, a sulfamethoxazole or other antibiotics.

In some embodiments, the additional therapeutic agent or agents is an antibiotic selected from a penicillin, a cephalosporin, a quinolone, an aminoglycoside or an oxazolidinone.

In other embodiments, the additional therapeutic agents are selected from a natural penicillin including Benzathine penicillin G, Penicillin G and Penicillin V, from a penicillinase-resistant penicillin including Cloxacillin, Dicloxacillin, Nafcillin and Oxacillin, from a antipseudomonal penicillin including Carbenicillin, Mezlocillin, Pipercillin, Pipercillin/tazobactam, Ticaricillin and Ticaricillin/Clavulanate, from an aminopenicillin including Amoxicillin, Ampicillin and Ampicillin/Sulbactam, from a first generation cephalosporin including Cefazolin, Cefadroxil, Cephalexin and Cephadrine, from a second generation cephalosporin including Cefaclor, Cefaclor-CD, Cefamandole, Cefonacid, Cefprozil, Loracarbef and Cefuroxime, from a third generation cephalosporin including Cefdinir, Cefixime, Cefoperazone, Cefotaxime, Cefpodoxime, Ceftazidime, Ceftibuten, Ceftizoxme and Ceftriaxone, from a fourth generation cephalosporin including Cefepime, Ceftaroline and Ceftobiprole, from a Cephamycin including Cefotetan and Cefoxitin, from a carbapenem including Imipenem and Meropenem, from a monobactam including Aztreonam, from a quinolone including Cinoxacin, Nalidixic acid, Oxolininc acid and Pipemidic acid, from a fluoroquinolone including Ciprofloxacin, Enoxacin, Gatifloxacin, Grepafloxacin, Levofloxacin, Lomefloxacin, Moxifloxacin, Norfloxacin, Ofloxacin and Sparfloxacin, from an aminoglycoside including Amikacin, Gentamicin, Kanamycin, Neomycin, Netilmicin, Spectinomycin, Streptomycin and Tobramycin, from a macrolide including Azithromycin, Clarithromycin and Erythromycin, from a ketolide including Telithromycin, from a Tetracycline including Chlortetracycline, Demeclocycline, Doxycycline, Minocycline and Tetracycline, from a glycopeptide including Oritavancin, Dalbavancin, Telavancin, Teicoplanin and *Vancomycin*, from a streptogramin including Dalfopristin/quinupristin, from an oxazolidone including Linezolid, from a Rifamycin including Rifabutin and Rifampin and from other antibiotics including bactitracin, Tygacil, Daptomycin, chloramphenicol, clindamycin, isoniazid, metronidazole, polymyxin B, pyrazinamide, and trimethoprim/sulfamethoxazole.

In other embodiments, the additional therapeutic agents are selected from a natural penicillin including Penicillin G, from a penicillinase-resistant penicillin including Nafcillin and Oxacillin, from an antipseudomonal penicillin including Pipercillin/tazobactam, from an aminopenicillin including Amoxicillin, from a first generation cephalosporin including Cephalexin, from a second generation cephalosporin including Cefaclor, Cefaclor-CD and Cefuroxime, from a third generation cephalosporin including Ceftazidime and Ceftriaxone, from a fourth generation cephalosporin including Cefepime, from a fluoroquinolone including Ciprofloxacin, Gatifloxacin, Levofloxacin and Moxifloxacin, from an aminoglycoside including Tobramycin, from a macrolide including Azithromycin and Clarithromycin, from a Tetracycline including Doxycycline, from a glycopeptide including *Vancomycin*, from a Rifamycin including Rifampin and from other antibiotics including isoniazid, pyrazinamide, Tygacil, Daptomycin or trimethoprim/sulfamethoxazole.

In some embodiments, a form of the Compound 1, e.g., a solid form of IA, IIA, IIB, IIC, IID, IIIB, or IIIC, is administered as a composition, for example a solid, liquid (e.g., a suspension), or an iv (e.g., a form of Compound 1 is dissolved into a liquid and administered iv). In some embodiments, the composition is administered with an additional therapeutic agent such as an antibiotic, for example an antibiotic described above. The additional therapeutic agent such as an antibiotic, for example an antibiotic described above, can be administered as a composition, for example a solid, liquid (e.g., a suspension), or an iv (e.g., a form of Compound 1 is dissolved into a liquid and administered iv). The additional agent can be administered before (e.g., about 1 day, about 12 hours, about 8 hours, about 6 hours, about 4 hours, about 2 hours, about 1 hour, about 30, or about 15 minutes or less), during, or after (e.g., about 15 minutes, about 30 minutes, about 1 hour, about 2 hours, about 4 hours, about 6 hours, about 8 hours, about 12, hours, or about 1 day, or more) the administration of the composition including Compound 1. In some embodiments, the composition including Compound 1 includes the additional therapeutic agent, for example, a solid, liquid (e.g., a suspension), or an iv (e.g., a form of Compound 1 is dissolved into a liquid and administered iv) composition includes a form of Compound 1, e.g., form IA, IIA, IIB, IIC, IID, IIIB, or IIIC, and at least one additional therapeutic agent such as an antibiotic, for example an antibiotic described above.

In some embodiments, a solid form of Compound 1, e.g., form IA, IIA, IIB, IIC, IID, IIIB, or IIIC, for example a composition including a solid form of Compound 1, can be administered for the treatment of a gram positive infection. In some embodiments, the composition is a solid, liquid (e.g., a suspension), or an iv (e.g., a form of Compound 1 is dissolved into a liquid and administered iv) composition. In some embodiments, the composition including Compound 1, is administered in combination with an additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a tetracycline, a glycopeptide, a streptogramin, an oxazolidinone, a rifamycin, or a sulfamethoxazole. In some embodiments, the composition including a solid form of Compound 1, e.g., form IA, IIA, IIB, IIC, IID, IIIB, or IIIC, is administered orally, and the additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a tetracycline, a glycopeptide, a streptogramin, an oxazolidinone, a rifamycin, or a sulfamethoxazole is administered iv.

In some embodiments, a solid form of Compound 1, e.g., form IA, IIA, IIB, IIC, IID, IIIB, or IIIC, for example a composition including a solid form of Compound 1, can be administered for the treatment of a gram negative infection. In some embodiments, the composition is a solid, liquid (e.g., a suspension), or an iv (e.g., a form of Compound 1 is dissolved into a liquid and administered iv) composition. In some embodiments, the composition including Compound 1, is administered in combination with an additional antibiotic agent, selected from a: natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide or a tetracycline. In some embodiments, the composition including a solid form of Compound 1, e.g., form IA, IIA, IIB, IIC, IID, IIIB, or IIIC, is administered orally, and the additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide or a tetracycline is administered orally. In some embodiments, the additional therapeutic agent is administered iv.

In one aspect, the invention features a method of treating a bacterial infection, the method comprising administering a solid form of Compound 1 described herein (e.g., form IA, IIA, IIB, IIC, IID, IIIB, or IIIC) to a subject.

In one aspect, the invention features a method of treating a bacterial infection, the method comprising administering a pharmaceutical composition described herein (e.g., a pharmaceutical composition comprising a solid form of Compound 1, such as form IA, IIA, IIB, IIC, IID, IIIB, or IIIC) to a subject. In some embodiments, the bacterial infection is characterized by the presence of one or more of *Streptococcus pneumoniae*, *Streptococcus pyogenes*, *Enterococcus faecalis*, *Enterococcus faecium*, *Klebsiella pneumoniae*, *Enterobacter* sps. *Proteus* sps. *Pseudomonas aeruginosa*, *E. coli*, *Serratia marcesens*, *Staphylococcus aureus*, Coag. Neg. Staph, *Haemophilus infuenzae*, *Bacillus anthracis*, *Mycoplasma pneumoniae*, *Moraxella catarralis*, *Chlamydia pneumoniae*, *Legionella pneumophila*, *Mycobacterium tuberculosis*, *Helicobacter pylori*, *Staphylococcus saprophyticus*, or *Staphylococcus epidermidis*.

In another embodiment, the bacterial infection is characterized by the presence of one or more of *Streptococcus pneumoniae*, *Streptococcus pyogenes*, *Enterococcus faecalis*, *Enterococcus faecium*, *Staphylococcus aureus*, Coag. Neg. Staph, *Bacillus anthracis*, *Staphylococcus epidermidis*, *Staphylococcus saprophyticus*, or *Mycobacterium tuberculosis*.

In another embodiment, the bacterial infection is characterized by the presence of one or more of *Streptococcus pneumoniae*, *Enterococcus faecalis*, or *Staphylococcus aureus*.

In another embodiment, the bacterial infection is characterized by the presence of one or more of *E. coli*, *Moraxella catarralis*, or *Haemophilus influenzae*.

In some embodiments, the bacterial infection is characterized by the presence of one or more of Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplama pneumoniae*, Isoniazid resistant *Mycobacterium tuberculosis*, Rifampin resistant *Mycobacterium tuberculosis*, Methicillin resistant Coagulase negative *staphylcocci*, Fluoroquinolone resistant Coagulase negative *staphylcocci*, Glycopeptide intermediate resistant *Staphylococcus aureus*, Vancomycin resistant *Staphylococcus aureus*, Hetero vancomycin intermediate resistant *Staphylococcus aureus*, Hetero vancomycin resistant *Staphylococcus aureus*, Macrolide-Lincosamide-Streptogramin resistant *Staphylococcus*, β-lactam resistant *Enterococcus faecalis*, β-lactam resistant *Enterococcus faecium*, Ketolide resistant *Streptococcus pneumoniae*, Ketolide resistant *Streptococcus pyogenes*, Macrolide resistant *Streptococcus pyogenes*, or Vancomycin resistant *staphylococcus epidermidis*.

According to another embodiment, the Methicillin resistant Staphylococci are selected from Methicillin resistant *Staphylococcus aureus*, Methicillin resistant *Staphylococcus epidermidis*, or Methicillin resistant Coagulase negative *staphylcoccus*.

In some embodiments, a form of the Compound 1, e.g., form IA, IIA, IIB, IIC, IID, IIIB, or IIIC, is used to treat that community acquired MRSA (i.e., cMRSA).

According to another embodiment, the Fluoroquinolone resistant Staphylococci are selected from Fluoroquinolone resistant *Staphylococcus aureus*, Fluoroquinolone resistant *Staphylococcus epidermidis*, or Fluoroquinolone resistant Coagulase negative *staphylcoccus*.

According to another embodiment, the Glycopeptide resistant Staphylococci are selected from Glycopeptide intermediate resistant *Staphylococcus aureus*, Vancomycin resistant *Staphylococcus aureus*, Vancomycin intermediate *Staphylococcus aureus*, Hetero vancomycin intermediate resistant *Staphylococcus aureus*, or Hetero vancomycin resistant *Staphylococcus aureus*.

According to another embodiment, the Macrolide-Lincosamide-Streptogramin resistant Staphylococci is Macrolide-Lincosamide-Streptogramin resistant *Staphylococcus aureus*.

According to another embodiment, the Linezolid resistant Enterococci are selected from Linezolid resistant *Enterococcus faecalis*, or Linezolid resistant *Enterococcus faecium*.

According to another embodiment, the Glycopeptide resistant Enterococci are selected from Vancomycin resistant *Enterococcus faecium* or Vancomycin resistant *Enterococcus faecalis*.

According to another embodiment, the β-lactam resistant *Enterococcus faecalis* is β-lactam resistant *Enterococcus faecium*.

According to another embodiment, the Penicillin resistant Streptococci is Penicillin resistant *Streptococcus pneumoniae*.

According to another embodiment, the Macrolide resistant Streptococci is Macrolide resistant *Streptococcus pneumonia*.

According to another embodiment, the Ketolide resistant Streptococci are selected from Macrolide resistant *Streptococcus pneumoniae* and Ketolide resistant *Streptococcus pyogenes*.

According to another embodiment, the Fluoroquinolone resistant Streptococci is Fluoroquinolone resistant *Streptococcus pneumoniae*.

According to another embodiment, the β-lactam resistant *Haemophilus* is β-lactam resistant *Haemophilus influenzae*.

According to another embodiment, the Fluoroquinolone resistant *Haemophilus* is Fluoroquinolone resistant *Haemophilus influenzae*.

According to another embodiment, the Macrolide resistant *Haemophilus* is Macrolide resistant *Haemophilus influenzae*.

According to another embodiment, the Macrolide resistant *Mycoplasma* is Macrolide resistant *Mycoplama pneumoniae*.

According to another embodiment, the Isoniazid resistant *Mycobacterium* is Isoniazid resistant *Mycobacterium tuberculosis*.

According to another embodiment, the Rifampin resistant *Mycobacterium* is Rifampin resistant *Mycobacterium tuberculosis*.

According to another embodiment, the β-lactam resistant *Moraxella* is β-lactam resistant *Moraxella catarrhalis*.

According to another embodiment, the bacterial infection is characterized by the presence of one or more of the following: Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*, Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*, Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplama pneumoniae*, Isoniazid resistant *Mycobacterium tuberculosis*, or Rifampin resistant *Mycobacterium tuberculosis*.

According to another embodiment, the bacterial infection is characterized by the presence of one or more of the following: Methicillin resistant *Staphylococcus aureus*, Methicillin resistant *Staphylococcus epidermidis*, Methicillin resistant Coagulase negative staphylcocci, Fluoroquinolone resistant *Staphylococcus aureus*, Fluoroquinolone resistant *Staphylococcus epidermidis*, Fluoroquinolone resistant Coagulase negative staphylcocci, Vancomycin resistant *Staphylococcus aureus*, Glycopeptide intermediate resistant *Staphylococcus aureus*, Vancomycin resistant *Staphylococcus aureus*, Vancomycin intermediate resistant *Staphylococcus aureus*, Hetero vancomycin intermediate resistant *Staphylococcus aureus*, Hetero vancomycin resistant *Staphylococcus aureus*, Vancomycin resistant *Enterococcus faecium*, Vancomycin resistant *Enterococcus faecalis*, Penicillin resistant *Streptococcus pneumoniae*, Macrolide resistant *Streptococcus pneumoniae*, Fluoroquinolone resistant *Streptococcus pneumoniae*, Macrolide resistant *Streptococcus pyogenes*, or β-lactam resistant *Haemophilus influenzae*.

According to another embodiment, Compound 1 (e.g., a solid form of Compound 1, such as form IA, IIA, IIB, IIC, IID, IIIB, or IIIC) may also be delivered by implantation (e.g., surgically), such as with an implantable or indwelling device. An implantable or indwelling device may be designed to reside either permanently or temporarily in a subject. Examples of implantable and indwelling devices include, but are not limited to, contact lenses, central venous catheters and needleless connectors, endotracheal tubes, intrauterine devices, mechanical heart valves, pacemakers, peritoneal dialysis catheters, prosthetic joints, such as hip and knee replacements, tympanostomy tubes, urinary catheters, voice prostheses, stents, delivery pumps, vascular filters and implantable control release compositions. Biofilms can be detrimental to the health of patients with an implantable or indwelling medical device because they introduce an artificial substratum into the body and can cause persistent infections. Thus, providing Compound 1 in or on the implantable or indwelling device can prevent or reduce the production of a biofilm. In addition, implantable or indwelling devices may be used as a depot or reservoir of Compound 1. Any implantable or indwelling device can be used to deliver Compound 1 provided that a) the device, Compound 1 and any pharmaceutical composition including Compound 1 are biocompatible, and b) that the device can deliver or release an effective amount of Compound 1 to confer a therapeutic effect on the treated patient.

Delivery of therapeutic agents via implantable or indwelling devices is known in the art. See for example, "Recent Developments in Coated Stents" by Hofma et al. published in *Current Interventional Cardiology Reports* 2001, 3:28-36, the entire contents of which, including references cited therein, incorporated herein by reference. Other descriptions of implantable devices can be found in U.S. Pat. Nos. 6,569,195 and 6,322,847; and U.S. Patent Application Numbers 2004/0044405, 2004/0018228, 2003/0229390, 2003/0225450, 2003/0216699 and 2003/0204168, each of which is incorporated herein by reference in its entirety.

In some embodiments, the implantable device is a stent. In one specific embodiment, a stent can include interlocked meshed cables. Each cable can include metal wires for structural support and polymeric wires for delivering the therapeutic agent. The polymeric wire can be dosed by immersing the polymer in a solution of the therapeutic agent. Alternatively, the therapeutic agent can be embedded in the polymeric wire during the formation of the wire from polymeric precursor solutions.

In other embodiments, implantable or indwelling devices can be coated with polymeric coatings that include the therapeutic agent. The polymeric coating can be designed to control the release rate of the therapeutic agent. Controlled release of therapeutic agents can utilize various technologies. Devices are known that have a monolithic layer or coating incorporating a heterogeneous solution and/or dispersion of an active agent in a polymeric substance, where the diffusion of the agent is rate limiting, as the agent diffuses through the polymer to the polymer-fluid interface and is released into the surrounding fluid. In some devices, a soluble substance is also dissolved or dispersed in the polymeric material, such that additional pores or channels are left after the material dissolves. A matrix device is generally diffusion limited as well, but with the channels or other internal geometry of the device also playing a role in releasing the agent to the fluid. The channels can be pre-existing channels or channels left behind by released agent or other soluble substances.

Erodible or degradable devices typically have the active agent physically immobilized in the polymer. The active agent can be dissolved and/or dispersed throughout the polymeric material. The polymeric material is often hydrolytically degraded over time through hydrolysis of labile bonds, allowing the polymer to erode into the fluid, releasing the active agent into the fluid. Hydrophilic polymers have a generally faster rate of erosion relative to hydrophobic polymers. Hydrophobic polymers are believed to have almost purely surface diffusion of active agent, having erosion from the surface inwards. Hydrophilic polymers are believed to allow water to penetrate the surface of the polymer, allowing hydrolysis of labile bonds beneath the surface, which can lead to homogeneous or bulk erosion of polymer.

The implantable or indwelling device coating can include a blend of polymers each having a different release rate of the therapeutic agent. For instance, the coating can include a polylactic acid/polyethylene oxide (PLA-PEO) copolymer and a polylactic acid/polycaprolactone (PLA-PCL) copolymer. The polylactic acid/polyethylene oxide (PLA-PEO) copolymer can exhibit a higher release rate of therapeutic agent relative to the polylactic acid/polycaprolactone (PLA-PCL) copolymer. The relative amounts and dosage rates of therapeutic agent delivered over time can be controlled by controlling the relative amounts of the faster releasing polymers relative to the slower releasing polymers. For higher initial release rates the proportion of faster releasing polymer can be increased relative to the slower releasing polymer. If most of the dosage is desired to be released over a long time period, most of the polymer can be the slower releasing polymer. The device can be coated by spraying the device with a solution or dispersion of polymer, active agent, and solvent. The solvent can be evaporated, leaving a coating of polymer and active agent. The active agent can be dissolved and/or dispersed in the polymer. In some embodiments, the co-polymers can be extruded over the device.

The compounds, compositions and methods described herein will therefore be useful for controlling, treating or reducing the advancement, severity or effects of nosocomial or non-nosocomial infections. Examples of nosocomial and non-nosocomial infections include but are not limited to upper respiratory infections, lower respiratory infections, ear infections, pleuropulmonary and bronchial infections, urinary tract infections, intra-abdominal infections, cardiovascular infections, a blood stream infection, sepsis, CNS infections, skin and soft tissue infections, GI infections, bone and joint infections, genital infections, eye infections, or granulomatous infections. Examples of specific bacterial infections include but are not limited to uncomplicated skin and skin structure infections, complicated skin and skin structure infections pharyngitis, sinusitis, otitis externa, otitis media, bronchitis, empyema, pneumonia, community acquired *pneumoniae* (CAP), cystitis and pyelonephritis, renal calculi, prostatitis, peritonitis, dialysis-associated peritonitis, visceral abscesses, endocarditis, myocarditis, pericarditis, transfusion-associated sepsis, meningitis, encephalitis, brain abscess, osteomyelitis, arthritis, genital ulcers, urethritis, vaginitis, cervicitis, gingivitis, conjunctivitis, keratitis, endophthalmitisa, an infection in cystic fibrosis patients or an infection of febrile neutropenic patients.

In some embodiments, Compound 1 may be used prophylactically to prevent a bacterial infection (e.g., a solid form of Compound 1, such as form IA, IIA, IIB, IIC, IID, IIIB, or IIIC). In some embodiments, Compound 1 may be used before, during or after a dental or surgical procedure to prevent opportunistic infections such as those encountered in bacterial endocarditis (e.g., a solid form of Compound 1, such as form IA, IIA, IIB, IIC, IID, IIIB, or IIIC). In other embodiments, Compound 1 (e.g., a solid form of Compound 1, such as form IA, IIA, IIB, IIC, IID, IIIB, or IIIC) may be used prophylactically in dental procedures, including but not limited to extractions, periodontal procedures, dental implant placements and endodontic surgery. In other embodiments, Compound 1 may be used prophylactically in surgical procedures including but not limited to general surgery, respiratory surgery (tonsillectomy/adenoidectomy), gastrointestinal surgery (upper GI and elective small bowel surgery, esophageal sclerotherapy and dilation, large bowel resections, acute appendectomy), trauma surgery (penetrating abdominal surgery), genito-urinary tract surgery (prostatectomy, urethral dilation, cystoscopy, vaginal or abdominal hysterectomy, cesarean section), transplant surgery (kidney, liver, pancreas or kidney transplantation), head and neck surgery (skin excisions, neck dissections, laryngectomy, head and neck cancer surgeries, mandibular fractures), orthopedic surgery (total joint replacement, traumatic open fractures), vascular surgery (peripheral vascular procedures), cardiothoracic surgery, coronary bypass surgery, pulmonary resection and neurosurgery.

In some embodiments, the bacterial infection is a nosocomial infection (e.g., urinary tract infections, pneumonia, surgical wound infections, bone and joint infections, and bloodstream infections). In some embodiments, the bacterial infection is a nosocomial infection (e.g., urinary tract infections, pneumonia, prostatitis, skin and soft tissue infections, bone and joint infections, intra-abdominal infections, meningitis, brain abscess, infectious diarrhea and gastrointestinal infections, surgical prophylaxis, and therapy for febrile neutropenic patients).

In some embodiments, the method further comprises administering an additional therapeutic agent. In some embodiments, the additional therapeutic agent is co-administered with 1-ethyl-3-(5-(5-fluoropyridin-3-yl)-7-(pyrimidin-2-yl)-1H-benzo[d]imidazol-2-yl)urea. In some embodiments, the additional therapeutic agent is an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

In one aspect, the invention provides a method of evaluating a solid form of Compound 1 (e.g., a solid form of Compound 1, such as form IA, IIA, IIB, IIC, IID, IIIB, or IIIC). The method includes:

providing an evaluation of a physical, chemical or biological parameter disclosed herein, e.g., the presence or absence of one or more peaks as measured by powder X-ray diffraction (the characteristic or value identified in this evaluation is sometimes referred to herein as a "signature"), optionally, providing a determination of whether the value or signature (e.g., a value or signature correlated to absence or presence) for the parameter meets a preselected criteria, e.g., is present, or is present in a preselected range, and thereby evaluating or processing the mixture.

In a preferred embodiment, the method includes providing a comparison of the value or signature with a reference, to thereby evaluate the sample. In preferred embodiments, the comparison includes determining if the test value or signature has a preselected relationship with the reference, e.g., determining if it meets the reference. The value or signature need not be numerical but can be merely an indication of whether a form is present or absent.

In a preferred embodiment, the method includes determining if a test value or signature is equal to or greater than a reference, if it is less than or equal to a reference, or if it falls within a range (either inclusive or exclusive of the endpoints of the range).

In preferred embodiments, the test value or signature, or an indication of whether the preselected relationship is met, can be memorialized, e.g., in a computer readable record.

In preferred embodiments, a decision or step is taken, e.g., the sample is classified, selected, accepted or discarded, released or withheld, processed into a drug product, shipped, moved to a new location, formulated, labeled, packaged, released into commerce, sold, or offered for sale. This can be based on whether the preselected criterion is met, e.g., based on the result of the determination of whether a signature is present, the batch from which the sample is taken can be processed.

In preferred embodiments, methods and compositions disclosed herein are useful from a process standpoint, e.g., to monitor or ensure batch-to-batch consistency or quality, or to evaluate a sample with regard to a reference, e.g., a preselected value.

In preferred embodiments, methods and compositions disclosed herein can be used to determine if a test batch of a solid form of Compound 1 (e.g., a solid form of Compound 1, such as form IA, IIA, IIB, IIC, IID, IIIB, or IIIC), can be expected to have one or more of the properties of a reference or standard for the Compound 1 (e.g., a solid form of Compound 1, such as form IA, IIA, IIB, IIC, IID, IIIB, or IIIC). Such properties can include a property listed on the product insert of an approved form of the drug, a property appearing in a compendium, e.g., the U.S. Pharmacopeia, or a property required by a regulatory agency, e.g., the U.S. Food and Drug Administration (the FDA), for commercial use. A determination made by a method disclosed herein can be a direct or indirect measure of such a property, e.g., a direct measurement can be where the desired property is a preselected level of the subject entity being measured. In an indirect measurement, the measured subject entity is correlated with a desired characteristic, e.g., a characteristic described herein.

In a preferred embodiment the party making the evaluation does not practice the method or analysis described herein but merely relies on results which are obtained by a method or analysis described herein.

Some of the methods described herein include evaluating a physical, chemical or biological parameter of a solid form of Compound 1, e.g., form IA, IIA, IIB, IIC, IID, IIIB, or IIIC, of Compound 1. Thus, in a preferred embodiment a chemical, physical, or biological parameter disclosed herein is evaluated or determined for a solid form of Compound 1, e.g., a form of a drug disclosed herein is evaluated for one or more of the following. A value or evaluation of one or more of these parameters is sometimes referred to herein as a signature.

The parameters include having one or more of a preselected:

powder X-ray diffraction pattern peak or peaks;

an endotherm or $T_m$, e.g., as measured in DSC;

a value for weight gain, e.g., from 5% to 95% relative humidity at 25° C. as measured using DVS;

solubility;

measure of the ability to remain in substantially the same physical form under preselected conditions;

a ss$^{13}$C-NMR pattern peak or peaks;

a P2$_1$/n space grouping; and unit cell dimensions disclosed herein.

In a preferred embodiment the drug form is Compound 1 form IA and the signature is one or more of:

a powder X-ray diffraction pattern peak or peaks;

an endotherm or $T_m$, e.g., as measured in DSC;

a value for weight gain, e.g., from 5% to 95% relative humidity at 25° C. as measured using DVS;

solubility;

a measure of the ability to remain in substantially the same physical form under preselected conditions; and a ss$^{13}$C-NMR pattern peak or peaks disclosed herein.

In a preferred embodiment the drug form is Compound 1.monoesylate and the signature is solubility.

In a preferred embodiment the drug is Compound 1 form IIA and the signature is one or more of:

a powder X-ray diffraction pattern peak or peaks;

an endotherm or $T_m$, e.g., as measured in DSC;

a value for weight gain, e.g., from 5% to 95% relative humidity at 25° C. as measured using DVS; and solubility disclosed herein.

In a preferred embodiment the drug is Compound 1 form IIB and the signature is one or more of:

a powder X-ray diffraction pattern peak or peaks;

an endotherm or $T_m$, e.g., as measured in DSC; and a measure of the ability to remain in substantially the same physical form under preselected conditions disclosed herein.

In a preferred embodiment the drug is Compound 1 form IIC and the signature is one or more of:

a powder X-ray diffraction pattern peak or peaks;

an endotherm or $T_m$, e.g., as measured in DSC;

a value for weight gain, e.g., from 5% to 95% relative humidity at 25° C. as measured using DVS;

solubility;

a measure of the ability to remain in substantially the same physical form under preselected conditions; and a ss$^{13}$C-NMR pattern peak or peaks disclosed herein.

In a preferred embodiment the drug is Compound 1 form IID and the signature is:

a powder X-ray diffraction pattern peak or peaks disclosed herein.

In a preferred embodiment the drug is Compound 1 form IIIB and the signature is one or more of:

a powder X-ray diffraction pattern peak or peaks;

an endotherm or $T_m$, e.g., as measured in DSC;

a value for weight gain, e.g., from 5% to 95% relative humidity at 25° C. as measured using DVS;

solubility;

a measure of the ability to remain in substantially the same physical form under preselected conditions;

a ss$^{13}$C-NMR pattern peak or peaks;

a P2$_1$/n space grouping; and having unit cell dimensions disclosed herein.

In a preferred embodiment the drug is Compound 1 form IIIC and the signature is one or more of:
a powder X-ray diffraction pattern peak or peaks; and
an endotherm or $T_m$, e.g., as measured in DSC disclosed herein.

In another aspect, the invention features a method of analyzing a process, e.g., a manufacturing process. The method includes:
providing a preparation of a solid form of Compound 1 (e.g., form IA, IIA, IIB, IIC, IID, IIIB, or IIIC);
providing an evaluation of a physical, chemical or biological parameter disclosed herein, e.g., the presence or absence of one or more peaks as measured by powder X-ray diffraction, and,
optionally, providing a determination of whether the value or signature for the parameter meets a preselected criteria, e.g., is present, or is present in a preselected range, thereby analyzing the process.

In one embodiment, the method further includes comparing the value determined with a reference value, to thereby analyze the manufacturing process.

In one embodiment, the method further includes maintaining the manufacturing process based, at least in part, upon the analysis. In one embodiment, the method further includes altering the manufacturing process based, at least in part, upon the analysis.

In a preferred embodiment the method includes: evaluating a process, e.g., manufacturing process, of a preparation of a solid form of Compound 1 made by a selected process that includes making a determination about the process based upon a method or analysis described herein (e.g., a solid form of Compound 1, such as form IA, IIA, IIB, IIC, IID, IIIB, or IIIC). In one embodiment, the method further includes maintaining or altering the manufacturing process based, at least in part, upon the method or analysis. Thus, in a preferred embodiment the party making the evaluation does not practice the method or analysis described herein but merely relies on results which are obtained by a method or analysis described herein.

In a preferred embodiment the method includes comparing two or more preparations, in a method of monitoring or controlling batch-to-batch variation or to compare a preparation to a reference standard.

In one embodiment, the method can further include making a decision, e.g., to classify, select, accept or discard, release or withhold, process into a drug product, ship, move to a different location, formulate, label, package, release into commerce, sell or offer for sale the preparation, based, at least in part, upon the determination.

In another aspect, the invention features, a method of evaluating, e.g., evaluating the quality of, a preparation of a solid form of Compound 1 described herein (e.g., form IA, IIA, IIB, IIC, IID, IIIB, or IIIC), e.g., in a quality control or release specification analysis. The method includes:
providing an evaluation of a physical, chemical or biological parameter disclosed herein, e.g., the presence or absence of one or more peaks as measured by powder X-ray diffraction, and,
optionally, providing a determination of whether the value or signature for the parameter meets a preselected criteria, e.g., is present, or is present in a preselected range,
if said determined value has a predetermined relationship with said standard, e.g., is within a preselected range of values, then selecting the preparation (wherein selecting can be selecting for packaging, use, sale, release into commerce, discarding, etc.).

In another aspect, the invention features a method of evaluating a preparation of a solid form of Compound 1 described herein (e.g., form IA, IIA, IIB, IIC, IID, IIIB, or IIIC). The method includes:
receiving data with regard to the presence or level of a form of a solid form of Compound 1 described herein (e.g., form IA, IIA, IIB, IIC, IID, IIIB, or IIIC), e.g., wherein the data was prepared by one or more methods described herein;
providing a record which includes said data and optionally includes an identifier for a batch of a solid form of Compound 1 described herein (e.g., form IA, IIA, IIB, IIC, IID, IIIB, or IIIC);
submitting said record to a decision-maker, e.g., a government agency, e.g., the FDA;
optionally, receiving a communication from said decision maker;
optionally, deciding whether to release to market the batch of a solid form of Compound 1 described herein (e.g., form IA, IIA, IIB, IIC, IID, IIIB, or IIIC) based on the communication from the decision maker. In one embodiment, the method further includes releasing the sample.

The term "chemically stable," as used herein, means that the form of Compound 1 (e.g., a solid form of Compound 1, such as form IA, IIA, IIB, IIC, IID, IIIB, or IIIC), does not decompose into one or more different chemical compounds when subjected to specified conditions, e.g., 40° C./75% relative humidity or room temperature, for a specified period of time, e.g., 1 day, 2 days, 3 days, 1 week, 2 weeks, 1 month, 2 months, 3 months, 6 months, 12 months, 18 months, 24 months, or longer. In some embodiments, less than 25% of the form of Compound 1 decomposes, in some embodiments, less than about 20%, less than about 15%, less than about 10%, less than about 5%, less than about 3%, less than about 1%, less than about 0.5% of the form of Compound 1 decomposes under the conditions specified. In some embodiments, no detectable amount of the form of Compound 1 decomposes.

The term "physically stable," as used herein, means that the form of Compound 1 (e.g., a solid form of Compound 1, such as form IA, IIA, IIB, IIC, IID, IIIB, or IIIC), does not change into one or more different physical forms of Compound 1 (e.g., different solid forms as measured by XRPD, DSC, etc.) when subjected to specified conditions, e.g., 40° C./75% relative humidity or room temperature, for a specified period of time, e.g., 1 day, 2 days, 3 days, 1 week, 2 weeks, 1 month, 2 months, 3 months, 6 months, 12 months, 18 months, 24 months, or longer. In some embodiments, less than 25% of the form of Compound 1 changes into one or more different physical forms when subjected to specified conditions, In some embodiments, less than about 20%, less than about 15%, less than about 10%, less than about 5%, less than about 3%, less than about 1%, less than about 0.5% of the form of Compound 1 changes into one or more different physical forms of Compound 1 when subjected to specified conditions. In some embodiments, no detectable amount of the form of Compound 1 changes into one or more different physical forms of Compound 1.

The term "treatment", as used herein, unless otherwise indicated, means the treatment or prevention of a bacterial infection as provided in the methods described herein, including curing, reducing the symptoms of or slowing the progress of said disorder. The terms "treat" and "treating" are defined in accord with the foregoing term "treatment".

The term "preventing a bacterial infection in a patient," as used herein, unless otherwise indicated, means the prophylactic use of an antibiotic, such as a gyrase inhibitor of the present invention, to prevent a bacterial infection. Treatment with a gyrase inhibitor could be done prophylactically to prevent an infection caused by an organism that is susceptible to the gyrase inhibitor. One general set of conditions where prophylactic treatment could be considered is when an individual is more vulnerable to infection due to, for example, weakened immunity, surgery, trauma, presence of an artificial device in the body (temporary or permanent), an anatomical defect, exposure to high levels of bacteria or possible exposure to a disease-causing pathogen. Examples of factors that could lead to weakened immunity include chemotherapy, radiation therapy, diabetes, advanced age, HIV infection, and transplantation. An example of an anatomical defect would be a defect in the heart valve that increases the risk of bacterial endocarditis. Examples of artificial devices include artificial joints, surgical pins, catheters, etc. Another set of situations where prophylactic use of a gyrase inhibitor might be appropriate would be to prevent the spread of a pathogen between individuals (direct or indirect). A specific example of prophylactic use to prevent the spread of a pathogen is the use of a gyrase inhibitor by individuals in a healthcare institution (for example a hospital or nursing home).

The term "substantially free" when referring to a designated form of Compound 1 (e.g., a solid or crystalline form described herein) means that there is less than 20% (by weight) of the designated form(s) or co-form(s) (e.g., a crystalline or amorphous form of Compound 1) present, more preferably, there is less than 10% (by weight) of the designated form(s) present, more preferably, there is less than 5% (by weight) of the designated form(s) present, and most preferably, there is less than 1% (by weight) of the designated crystalline form(s) present.

The term "substantially pure" when referring to a designated form of Compound 1 (e.g., solid or crystalline form described herein) means that the designated crystalline form contains less than 20% (by weight) of residual components such as alternate polymorphic or isomorphic crystalline form(s) or co-form(s) of Compound 1. It is preferred that a substantially pure form of Compound 1 contain less than 10% (by weight) of alternate polymorphic or isomorphic crystalline forms of Compound 1, more preferred is less than 5% (by weight) of alternate polymorphic or isomorphic crystalline forms of Compound 1, and most preferably less than 1% (by weight) of alternate polymorphic or isomorphic crystalline forms of Compound 1.

This patent often refers to evaluating a chemical, physical or biological parameter disclosed herein. Such parameters can be substituted with other chemical, physical or biological parameters which though not disclosed herein are essentially similar in terms of identifying the form.

Methods and compositions disclosed herein can be used where the presence, distribution, or amount, of one or more structure in the mixture may possess or impinge on the biological activity. The methods are also useful from a structure-activity prospective, to evaluate or ensure biological equivalence.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1a and 1b depict the observed crystal structure of form IA.
FIG. 2 depicts an exemplary XRPD of form IA.
FIG. 3 depicts an exemplary DSC trace of form IA.
FIG. 4 depicts an exemplary TGA trace of form IA.
FIG. 5 depicts an exemplary DVS trace of form IA.
FIG. 6 depicts an exemplary ss$^{13}$C-NMR trace of form IA.
FIG. 7 depicts an exemplary XRPD of form IIA.
FIG. 8 depicts an exemplary DSC trace of form IIA.
FIG. 9 depicts an exemplary TGA trace of form IIA.
FIG. 10 depicts an exemplary DVS trace of form IIA.
FIG. 11 depicts an exemplary XRPD of form IIB.
FIG. 12 depicts an exemplary DSC trace of form IIB.
FIG. 13 depicts an exemplary XRPD of form IIC.
FIG. 14 depicts an exemplary DSC trace of form IIC.
FIG. 15 depicts an exemplary TGA trace of form IIC.
FIG. 16 depicts an exemplary DVS trace of form IIC.
FIG. 17 depicts an exemplary ss$^{13}$C-NMR trace of form IIC.
FIG. 18 depicts an exemplary XRPD of form IID.
FIG. 19 depicts an exemplary DSC trace of form IID
FIG. 20 depicts an exemplary TGA trace of form IID.
FIG. 21 depicts an exemplary XRPD of form IIIB
FIG. 22 depicts an exemplary DSC trace of form IIIB
FIG. 23 depicts an exemplary TGA trace of form IIIB
FIG. 24 depicts an exemplary DVS trace of form IIIB
FIG. 25 depicts an exemplary crystal structure plot of form IIIB
FIG. 26 depicts an exemplary $^1$H NMR trace of form IIIB
FIG. 27 depicts an exemplary ss$^{13}$C-NMR trace of form IIIB
FIG. 28 depicts an exemplary XRPD of form IIIC
FIG. 29 depicts an exemplary DSC trace of form IIIC.
FIG. 30 depicts an exemplary TGA trace of form IIIC.
Like reference symbols in the various drawings indicate like elements.

DETAILED DESCRIPTION

Solid Forms of Compound 1 and Methods of Making the Same

Compound 1 has been prepared in various solid forms, including salts and co-solvates. The reference form and name for each of these solid forms are provided in Table 1 below:

TABLE 1

Solid forms of Compound 1

| Reference form | Name |
| --- | --- |
| IA | crystalline 1-ethyl-3-(5-(5-fluoropyridin-3-yl)-7-(pyrimidin-2-yl)-1H-benzo[d]imidazol-2-yl)urea |
| IIA | 1-ethyl-3-(5-(5-fluoropyridin-3-yl)-7-(pyrimidin-2-yl)-1H-benzo[d]imidazol-2-yl)urea•monoesylate |
| IIB | 1-ethyl-3-(5-(5-fluoropyridin-3-yl)-7-(pyrimidin-2-yl)-1H-benzo[d]imidazol-2-yl)urea•monoesylate |
| IIC | 1-ethyl-3-(5-(5-fluoropyridin-3-yl)-7-(pyrimidin-2-yl)-1H-benzo[d]imidazol-2-yl)urea•monoesylate |
| IID | 1-ethyl-3-(5-(5-fluoropyridin-3-yl)-7-(pyrimidin-2-yl)-1H-benzo[d]imidazol-2-yl)urea•monoesylate |
| IIIB | 1-ethyl-3-(5-(5-fluoropyridin-3-yl)-7-(pyrimidin-2-yl)-1H-benzo[d]imidazol-2-yl)urea•monomesylate |
| IIIC | 1-ethyl-3-(5-(5-fluoropyridin-3-yl)-7-(pyrimidin-2-yl)-1H-benzo[d]imidazol-2-yl)urea•monomesylate |

Each of the solid forms outlined above were analyzed using one or more analytical techniques described below: single crystal analysis, X-ray powder diffraction (XRPD), differential scanning calorimetry (DSC), thermogravimetric analysis (TGA), dynamic vapor sorption (DVS), ss$^{13}$C-NMR, $^1$H NMR, stability analysis (e.g., chemical and/or physical stability), and solubility analysis.

Form IA

Form IA can be prepared by precipitating Compound 1 from an aqueous solution, for example, by adjusting an acidic solution to pH 7. In some embodiments, the resulting solid can be triturated with a protic solvent such as methanol (e.g., hot methanol). In some embodiments, the aqueous solution of Compound 1 is a product of a chemical synthesis of Compound 1, for example as provided in Example 1.

Form IA, as observed by single crystal structure data at room temperature, is a Triclinic P-1 system, and has the following unit cell dimensions:

a=10.088(2) Å, b=12.866(3) Å, c=14.242(3) Å
α=82.700(14)°, β=83.793(14)°, γ=72.628(13)°
cell volume=1745.1(7) Å3.

The single crystal structure of form IA is depicted in FIGS. 1a and 1b.

A representative XRPD of form IA is provided in FIG. 2. Representative peaks as observed in the XRPD are provided in Table 1 below:

TABLE 1

Representative XRPD peaks for form IA

| Angle 2-Theta ° | d value Angstrom | Intensity % | Pick |
|---|---|---|---|
| 6.4 | 13.75 | 100 | * |
| 9.3 | 9.53 | 9.8 | |
| 12.8 | 6.93 | 4.1 | |
| 14.1 | 6.29 | 16.2 | * |
| 15.4 | 5.76 | 5.7 | * |
| 19.8 | 4.48 | 2.8 | |
| 20.4 | 4.35 | 7.7 | |
| 20.7 | 4.28 | 7.3 | |
| 22.1 | 4.02 | 3.2 | |
| 24.2 | 3.67 | 4.1 | |
| 26.9 | 3.32 | 13.8 | |
| 27.7 | 3.22 | 4.8 | |

Form IA can be characterized by a $T_m$ of about 270° C., as observed by DSC. Form IA generally gains about 8% in weight when subjected to a step isothermic study (e.g., DVS) as observed from 5% to 95% relative humidity. Form IA has a solubility of about 2 mg/mL at a pH of about 1.

Form IA can be characterized by the ss$^{13}$C-NMR pattern depicted in FIG. 6. Exemplary peaks include one or more of the following as measured in ppm: 162.3, 158.8, 157.0, 149.5, 142.0, 137.5, 136.0, 131.8, 125.9, 119.3, 114.7, 35.9, and 16.3.

Form IA is generally chemically and physically stable for at least about 2 weeks, (e.g., at least about 4 weeks, 2 months, 3 months, or 6 months) under various conditions, including at 40° C./75% RH (e.g., in an open container). As described herein a compound that is chemically stable shows little to no degradation products under the specified conditions, for example, as observed with HPLC. A compound that is physically stable generally does not convert to a different solid form under the specified conditions, for example, as observed with XRPD. Form IA is also generally chemically and physically stable when subjected to mild mechanical stress such as grinding.

Form IIA

Form IIA can be prepared by dissolving Compound 1 in a mixture of EtOH/CH$_2$Cl$_2$ under heat with stirring and adding one equivalent of ethanesulfonic acid to the mixture. The solvent is left open to evaporate until crystals start forming. More solvent can then be added to dissolve the formed crystals. The vial is then closed with aluminum foil having three pinholes and kept at room temperature with stiffing (e.g., gentle stiffing such as less than 100 rpm). The slurring of the mixture is continued until solvent evaporation and formation of the solid material. The resulting material is then filtered and dried. Form IIA can also be prepared using any of the following solvent systems: acetonitrile/water; acetonitrile/methanol; MIK/methanol, chloroform; toluene/methanol, hexane/methanol, and acetone/water with the general procedure described above. In some instances, where necessary, additional solvent is added while heated to dissolve the starting compound. In some instances the solution of EtOH/CH$_2$Cl$_2$ can be added to a stirred solution of diethyl ether to produce form IIA.

Form IIA, has a representative XRPD as provided in FIG. 7. Representative peaks as provided in the XRPD of FIG. 7 are provided in Table 2 below:

TABLE 2

Representative XRPD peaks for form IIA

| Angle 2-Theta ° | d value Angstrom | Intensity % | Pick |
|---|---|---|---|
| 6.5 | 13.57 | 16.3 | |
| 7.2 | 12.35 | 100 | * |
| 12.6 | 7.01 | 22.9 | |
| 14.4 | 6.14 | 11 | |
| 15.6 | 5.66 | 23.2 | * |
| 18.6 | 4.78 | 28.1 | |
| 19.6 | 4.53 | 15.4 | |
| 21.7 | 4.10 | 13.4 | |
| 22.6 | 3.93 | 11.9 | |
| 25.4 | 3.50 | 14.2 | * |
| 27.1 | 3.28 | 40.5 | |

Form IIA can be characterized by a $T_m$ of about 215° C., as observed by DSC. Form IIA generally gains about 10% in weight when subjected to a step isothermic study (e.g., DVS) as observed from 5% to 95% relative humidity. Form IIA has a solubility of approximately 150 mg/ml to 250 mg/ml at a pH of between about/approximately 1.2 to 1.6, for example, >150 mg/ml at a pH of about 1.6.

Form IIB

Form IIB can be prepared by converting form IIA to form IIB. For example, form IIA can be converted to form IIB by subjecting form IIA to conditions of 40° C./75% RH for about 24 hours or for about 2 weeks.

A representative XRPD of form IIB is provided in FIG. 11. Representative peaks as observed in the XRPD are provided in Table 3 below:

TABLE 3

Representative XRPD peaks for form IIB

| Angle 2-Theta ° | d value Angstrom | Intensity % | Pick |
|---|---|---|---|
| 6.2 | 14.28 | 21.1 | * |
| 7.4 | 11.93 | 100 | * |
| 8.1 | 10.91 | 20.1 | |
| 12.4 | 7.14 | 16 | |
| 13.2 | 6.71 | 15.2 | |
| 14.5 | 6.11 | 26.2 | |
| 16.3 | 5.43 | 67.2 | |
| 17.1 | 5.17 | 33 | |
| 17.8 | 4.98 | 22 | |
| 18.6 | 4.76 | 24.9 | |
| 19.8 | 4.48 | 18.8 | |
| 21.0 | 4.24 | 18 | |
| 21.5 | 4.13 | 25.2 | |
| 22.9 | 3.88 | 20.3 | |
| 25.0 | 3.56 | 22.3 | |

TABLE 3-continued

Representative XRPD peaks for form IIB

| Angle 2-Theta ° | d value Angstrom | Intensity % | Pick |
|---|---|---|---|
| 26.0 | 3.43 | 30.8 | |
| 27.2 | 3.28 | 51.8 | |
| 27.9 | 3.20 | 38.3 | * |

Form IIB can be characterized by a $T_m$, of from about 214 to 216° C. Form IIB has a solubility of approximately 150 mg/ml to 250 mg/ml at a pH of between about/approximately 1.2 to 1.6, for example, >150 mg/ml in a solution having a pH of about 1.6.

Form IIC

Form IIC can be prepared by dissolving Compound 1 in a mixture of EtOH/$CH_2Cl_2$ under heat with stirring and adding one equivalent of ethanesulfonic acid to the mixture and heating at elevated temperature (e.g., 40° C.) until dissolved. The solution is filtered, concentrated in vacuo, diluted with $CH_2Cl_2$, and added dropwise to a stirred solution of diethyl ether. The resulting solid is filtered and dried to produce solid I. Solid I is then dissolved and recrystallized in one of acetonitrile, methanol, or ethanol to produce a solid of form IIC.

A representative XRPD of form IIC is provided in FIG. 13. Representative peaks as observed in the XRPD are provided in Table 4 below:

TABLE 4

Representative XRPD peaks for form IIC

| Angle 2-Theta ° | d value Angstrom | Intensity % | Pick |
|---|---|---|---|
| 8.2 | 10.78 | 100 | |
| 9.6 | 9.24 | 81.7 | * |
| 10.3 | 8.54 | 28.6 | * |
| 12.4 | 7.14 | 8.7 | |
| 16.5 | 5.37 | 7.3 | |
| 18.4 | 4.81 | 46.9 | |
| 20.4 | 4.34 | 7.5 | |
| 22.2 | 4.01 | 13 | |
| 24.8 | 3.58 | 35.8 | * |
| 26.0 | 3.43 | 16.3 | |

Form IIC can be characterized by a $T_m$ of from about 216° to 220° C., as observed by DSC. Form IA generally gains about 4% in weight when subjected to a step isothermic study (e.g., DVS) as observed from 5% to 95% relative humidity. Form IIC has a solubility of >150 mg/ml in an aqueous solution of pH about 1.6.

Form IIC can be characterized by the ss$^{13}$C-NMR pattern as depicted in FIG. 17. Exemplary peaks include one or more of the following as measured in ppm: 160.9, 159.2, 157.1, 151.7, 146.3, 142.0, 139.0, 135.4, 131.0, 129.7, 127.5, 124.1, 119.8, 113.7, 106.4, 14.1, and 9.1.

Form IIC is generally chemically and physically stable for at least about 2 weeks (e.g., at least about 4 weeks, at least about 2 months, at least about 3 months, at least about 4 months, or at least about 6 months) under a variety of standard storage conditions, including at 40° C./75% RH (e.g., in an open container), it is expected that form IIC would be stable at room temperature for at least about.

Form IID

Form IID can be prepared using a procedure similar to that described to make form IIA, where the solvent system is an ethanol/methanol solvent system.

A representative XRPD of form IID is provided in FIG. 18. Representative peaks as observed in the XRPD are provided in Table 5 below:

TABLE 5

Representative XRPD peaks of form IID

| Angle 2-Theta ° | d value Angstrom | Intensity % | Pick |
|---|---|---|---|
| 8.0 | 11.00 | 95.1 | * |
| 9.3 | 9.55 | 100 | |
| 11.3 | 7.85 | 21 | * |
| 13.2 | 6.69 | 12.1 | |
| 16.1 | 5.49 | 14.9 | |
| 16.6 | 5.34 | 20.9 | |
| 17.3 | 5.13 | 24.9 | |
| 19.0 | 4.66 | 37.4 | |
| 19.4 | 4.58 | 33.2 | |
| 19.8 | 4.47 | 39.1 | |
| 21.2 | 4.20 | 24.1 | |
| 21.5 | 4.13 | 42.8 | |
| 22.1 | 4.03 | 65.4 | |
| 24.0 | 3.71 | 94.3 | * |
| 26.9 | 3.31 | 41.1 | |

Form IID can be characterized by a $T_m$, of 205° C., as observed by DSC. Form IID has a solubility of >150 mg/ml in an aqueous solution of pH about 1.6.

Form IIIB

Form IIIB can be prepared by suspending Compound 1 in EtOH/$CH_2Cl_2$, adding to the suspension methanesulfonic acid, and stirring the resulting mixture until dissolution. The solution is then filtered, concentrated in vacuo and the resulting oily residue redissolved in $CH_2Cl_2$. The resulting solution was added dropwise to a stirred solution of diethylether to provide an off white precipitate.

For IIIB, as observed in single crystal structure data, has a $P2_1/n$ space group and the following unit cell dimensions:
a=14.3252(8) Å
b=8.7553(5) Å
c=17.0047(10) Å,
α=90°.
β=95.340(3)°.
γ=90°.
Volume 2123.5(2) Å3
R1=0.0304, wR2=0.0832. The single crystal structure of form IIIB is depicted in FIG. 25.

A representative XRPD of form IIIB is provided in FIG. 21. Representative peaks as observed in the XRPD are provided in Table 7 below:

TABLE 7

Peaklist of XRPD data collected for form IIIB

| Angle 2-Theta ° | d value Angstrom | Intensity % | Pick |
|---|---|---|---|
| 8.7 | 10.20 | 27.9 | |
| 10.6 | 8.31 | 21.5 | |
| 11.6 | 7.65 | 23.2 | |
| 12.0 | 7.34 | 54.8 | * |
| 13.4 | 6.61 | 64.2 | |
| 15.6 | 5.66 | 50.2 | * |
| 16.4 | 5.40 | 48.9 | |
| 17.7 | 5.02 | 38.1 | |
| 20.1 | 4.42 | 100 | |
| 21.2 | 4.19 | 49.9 | |
| 21.9 | 4.05 | 69.6 | |
| 24.7 | 3.60 | 70.2 | * |
| 27.0 | 3.30 | 71.2 | |
| 30.5 | 2.93 | 40.1 | |
| 33.0 | 2.71 | 31.6 | |

Form IIIB can be characterized by a $T_m$ of about 215° C., as observed by DSC. Form IIIB generally gains about 4.6% in weight when subjected to a step isothermic study (e.g., DVS) as observed from 5% to 95% relative humidity at 25° C. Form IIIB has a solubility of about >12 mg/ml at pH of about 4.4, and >12 mg/ml in simulated gastric fluid (SGF).

Form IIIB can be characterized by the ss$^{13}$C-NMR pattern depicted in FIG. 27. Exemplary peaks include one or more of the following as measured in ppm: 161.7, 159.9, 157.9, 153.6, 146.5, 140.6, 133.8, 132.6, 130.0, 127.9, 125.8, 122.8, 119.3, 117.8, 107.4, 39.5, 38.0, and 15.8.

Form IIIB is generally stable (e.g., chemically stable and physically stable) for at least about 2 weeks (e.g., at least about 1 month) under either general storage conditions (e.g., ambient), or at accelerated conditions, e.g., including 40° C./75% relative humidity.

Form IIIC

Form IIIC can be prepared by suspending Compound 1 in chloroform and adding an aqueous solution of methane sulfonic acid. The resulting slurry is triturated, filtered and dried (e.g., air dried) to provide form IIIC.

A representative XRPD of form IIIC is provided in FIG. 28. Representative peaks as observed in the XRPD are provided in Table 8 below:

TABLE 8

Peaklist of XRPD data collected for form IIIC

| Angle 2-Theta ° | d value Angstrom | Intensity % | Pick |
|---|---|---|---|
| 7.0 | 12.53374 | 100 | * |
| 13.3 | 6.6372 | 4.6 | |
| 14.1 | 6.28705 | 6.7 | |
| 14.7 | 6.00595 | 4.5 | |
| 16.5 | 5.37128 | 15.3 | |
| 18.5 | 4.78225 | 5.8 | |
| 19.5 | 4.53932 | 5.2 | * |
| 20.8 | 4.2649 | 12 | |
| 21.2 | 4.19497 | 11.8 | * |
| 23.1 | 3.8404 | 5.8 | |
| 23.6 | 3.77215 | 4.2 | |

Form IIIC can be characterized by a $T_m$ of about 235° C., as observed with DSC.

Methods of Using Compound 1 and Solid Forms thereof.

The solid forms of Compound 1 described herein are useful generally for controlling bacterial infections in vivo. Examples of bacterial organisms that may be controlled by the compositions and methods of this invention include, but are not limited to the following organisms: *Streptococcus pneumoniae, Streptococcus pyogenes, Enterococcus faecalis, Enterococcus faecium, Klebsiella pneumoniae, Enterobacter* sps. *Proteus* sps. *Pseudomonas aeruginosa, E. coli, Serratia marcesens, Staphylococcus aureus,* Coag. Neg. *Staph, Haemophilus infuenzae, Bacillus anthracis, Mycoplasma pneumoniae, Moraxella catarralis, Chlamydia pneumoniae, Legionella pneumophila, Mycobacterium tuberculosis, Helicobacter pylori, Staphylococcus saprophyticus,* and *Staphylococcus epidermidis.*

A solid form of Compound 1, e.g., form IA, IIA, IIB, IIC, IID, IIIB, or IIIC, for example a composition including a solid form of Compound 1, can be useful for the treatment of a gram positive infection. For example, the composition can be a solid, liquid (e.g., a suspension), or an iv (e.g., a form of Compound 1 is dissolved into a liquid and administered iv) composition. The composition including Compound 1, can be administered in combination with an additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a tetracycline, a glycopeptide, a streptogramin, an oxazolidinone, a rifamycin, or a sulfamethoxazole. The composition including a solid form of Compound 1, e.g., form IA, IIA, IIB, IIC, IID, IIIB, or IIIC, can be administered orally, and the additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide, a tetracycline, a glycopeptide, a streptogramin, an oxazolidinone, a rifamycin, or a sulfamethoxazole can be administered iv.

A solid form of Compound 1, e.g., form IA, IIA, IIB, IIC, IID, IIIB, or IIIC, for example a composition including a solid form of Compound 1, can be administered for the treatment of a gram negative infection. The composition can be a solid, liquid (e.g., a suspension), or an iv (e.g., a form of Compound 1 is dissolved into a liquid and administered iv) composition. The composition including Compound 1, can be administered in combination with an additional antibiotic agent, selected from: a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide or a tetracycline. The composition including a solid form of Compound 1, e.g., form IA, IIA, IIB, IIC, IID, IIIB, or IIIC, can be administered orally, and the additional antibiotic agent, for example, a natural penicillin, a penicillinase-resistant penicillin, an antipseudomonal penicillin, an aminopenicillin, a first generation cephalosporin, a second generation cephalosporin, a third generation cephalosporin, a fourth generation cephalosporin, a carbapenem, a cephamycin, a monobactam, a quinolone, a fluoroquinolone, an aminoglycoside, a macrolide, a ketolide or a tetracycline can also be administered orally. Alternatively, the additional therapeutic agent can be administered iv.

The solid forms of Compound 1 described herein are useful, for example, for controlling, treating or reducing the advancement, severity or effects of nosocomial or non-nosocomial infections. Examples of nosocomial infection uses include, but are not limited to, urinary tract infections, pneumonia, surgical wound infections, bone and joint infections, and bloodstream infections. Examples of non-nosocomial uses include but are not limited to urinary tract infections, pneumonia, prostatitis, skin and soft tissue infections, bone and joint infections, intra-abdominal infections, meningitis, brain abscess, infectious diarrhea and gastrointestinal infections, surgical prophylaxis, and therapy for febrile neutropenic patients. The term "non-nosocomial infections" is also referred to as community acquired infections.

According to another embodiment, the methods of the present invention are useful to treat patients in the veterinarian field including, but not limited to, zoo, laboratory, human companion, and farm animals including primates, rodents, reptiles and birds. Examples of said animals include, but are not limited to, guinea pigs, hamsters, gerbils, rat, mice, rabbits, dogs, cats, horses, pigs, sheep, cows, goats, deer, rhesus monkeys, monkeys, tamarinds, apes, baboons, gorillas, chimpanzees, orangutans, gibbons, ostriches, chickens, turkeys, ducks, and geese.

Pharmaceutical compositions of this invention comprise solid forms of Compound 1 e.g., form IA, IIA, IIB, IIC, IID, IIIB, or IIIC, described herein and a pharmaceutically acceptable carrier. Such compositions may optionally comprise an additional therapeutic agent. Such agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The term "pharmaceutically acceptable carrier" refers to a non-toxic carrier that may be administered to a patient, together with a compound of this invention, and which does not destroy the pharmacological activity thereof.

Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as α-tocopherol, polyethyleneglycol 1000 succinate, or other similar polymeric delivery matrices.

In pharmaceutical compositions comprising only a solid form of Compound 1 described herein e.g., form IA, IIA, IIB, IIC, IID, IIIB, or IIIC, as the active component, methods for administering these compositions may additionally comprise the step of administering to the subject an additional agent. Such agents include, but are not limited to, an antibiotic, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The term "pharmaceutically effective amount" refers to an amount effective in treating or ameliorating a bacterial infection in a patient. The term "prophylactically effective amount" refers to an amount effective in preventing or substantially lessening a bacterial infection in a patient.

The compounds of this invention may be employed in a conventional manner for controlling bacterial infections levels in vivo and for treating diseases or reducing the advancement or severity of effects which are mediated by bacteria. Such methods of treatment, their dosage levels and requirements may be selected by those of ordinary skill in the art from available methods and techniques.

For example, a solid form of Compound 1 described herein, e.g., form IA, IIA, IIB, IIC, IID, IIIB, or IIIC, may be combined with a pharmaceutically acceptable adjuvant for administration to a patient suffering from a bacterial infection or disease in a pharmaceutically acceptable manner and in an amount effective to lessen the severity of that infection or disease.

Alternatively, a solid form of Compound 1 described herein, e.g., form IA, IIA, IIB, IIC, IID, IIIB, or IIIC, may be used in compositions and methods for treating or protecting individuals against bacterial infections or diseases over extended periods of time. The compounds may be employed in such compositions either alone or together with other compounds of this invention in a manner consistent with the conventional utilization of enzyme inhibitors in pharmaceutical compositions. For example, a compound of this invention may be combined with pharmaceutically acceptable adjuvants conventionally employed in vaccines and administered in prophylactically effective amounts to protect individuals over an extended period of time against bacterial infections or diseases.

A solid form of Compound 1, e.g., form IA, IIA, IIB, IIC, IID, IIIB, or IIIC, may also be co-administered with other antibiotics to increase the effect of therapy or prophylaxis against various bacterial infections. When the compounds of this invention are administered in combination therapies with other agents, they may be administered sequentially or concurrently to the patient. Alternatively, pharmaceutical or prophylactic compositions according to this invention comprise a combination of a solid form of Compound 1 and another therapeutic or prophylactic agent.

The pharmaceutical compositions of this invention may be administered orally, parenterally, by inhalation spray, topically, via ophthalmic solution or ointment, rectally, nasally, buccally, vaginally or via an implanted reservoir. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and solutions and propylene glycol are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-administered transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between 0.5 and about 75 mg/kg body weight per day and most preferably between about 1 and 50 mg/kg body weight per day of the active ingredient compound are useful in a monotherapy for the prevention and treatment of bacterial infections caused by bacteria such as *Streptococcus pneumoniae, Streptococcus pyogenes, Enterococcus faecalis, Enterococcus faecium, Klebsiella pneumoniae, Enterobacter* sps. *Proteus* sps. *Pseudomonas aeruginosa, E. coli, Serratia marcesens, Staphylococcus aureus,* Coag. Neg. *Staph, Haemophilus infuenzae, Bacillus anthracis, Mycoplasma pneumoniae, Moraxella catarralis, Chlamydia pneumoniae, Legionella pneumophila, Mycobacterium tuberculosis, Helicobacter pylori, Staphylococcus saprophyticus,* or *Staphylococcus epidermidis*.

Typically, the pharmaceutical compositions of this invention will be administered from about 1 to 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a solid form of Compound 1, e.g., form IA, IIA, IIB, IIC, IID, IIIB, or IIIC, and one or more additional therapeutic or prophylactic agents, both the compound and the additional agent should be present at dosage levels of between about 10% to 80% of the dosage normally administered in a monotherapy regime.

Upon improvement of a patient's condition, a maintenance dose of a compound, composition or combination of this invention may be administered, if necessary. Subsequently, the dosage, dosage form, or frequency of administration, or both, may need to be modified. In some cases, patients may, however, require intermittent treatment on a long-term basis upon any recurrence or disease symptoms.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

One embodiment of this invention provides a method for treating or preventing a bacterial infection or disease in a subject comprising the step of administering to the subject any compound, pharmaceutical composition, or combination described herein and a pharmaceutically acceptable carrier.

EXAMPLES

Example 1

Synthesis of Compound 6, Form IA

Compound 6, form IA, was prepared using the schemes and experimentals provided below. As provided in the experimentals following the scheme, form IA was provided by precipitating the synthetic product from an aqueous solution (i.e., by neutralizing an aqueous solution).

The analytical methods used throughout the experimental procedures that follow include: (A) HPLC on a Waters XBridge Phenyl column, 4.6×75 mm, 3.5 microns. Mobile phase A is water/1 M ammonium formate, pH 7.0 (99:1). Mobile phase B is ACN/Water/1 M ammonium formate, pH 7.0 (90:9:1). Gradient 10 to 100% B in 10 to 12 min. Flow rate 1.2 mL/min. Detection at UV 245 nm. T=30° C.

(B) LC on an Agilent RP18, 4.6×250 mm column. Mobile phase ACN/H$_2$O/TFA (60:40:0.1). Detection at 265 nm. Flow rate 1.0 mL/min. Run time 22 min.

(C) GC on an HP-5 column. Using H$_2$ as the carrier gas and a temperature gradient of 8-2-10-240. Flow rate 1.4 mL/min. Run time 24 min.

(D) HPLC on an Altima C18 4.6×250 mm column. Mobile phase ACN/H$_2$O (7:3). Detection at 220 nm. Flow rate 1.0 mL/min. Ambient temp. Run time 21 min.

(E) Same as (D) with mobile phase ACN/H$_2$O/TFA (70:30:0.1) and detection at 250 nm.

(F) LC on an Agilent HC-C18 4.6×250 mm column. Mobile phase ACN/H$_2$O/TFA (50:50:0.1). Detection 250 nm. Flow rate 1.0 mL/min. Ambient temp. Run time 25 min.

(G) same as (E) but with a lower flow rate of 0.8 ml/min and mobile phase 70:30:0.1%.

(H) GC on a J&W DB-1 column, 60 m×0.32 mm i.d., 3.0 mm film thickness. Carrier gas He. Run time 17.0 min. Initial temperature 40° C., hold at 40° C. for 5 min. Ramp to 100° C. (10° C./min), then ramp to 240° C. (35° C./min) and hold at 240° C. for 2 min. Column flow 2.5 mL/min Helium (constant). FID detector. Split ratio 30:1.

The following definitions describe terms and abbreviations used herein:

| | |
|---|---|
| Ac | acetyl |
| Bu | butyl |
| Et | ethyl |
| Ph | phenyl |
| Me | methyl |
| THF | tetrahydrofuran |
| DCM | dichloromethane |
| $CH_2Cl_2$ | dichloromethane |
| EtOAc | ethyl acetate |
| $CH_3CN$ | acetonitrile |
| EtOH | ethanol |
| MeOH | methanol |
| MTBE | methyl tert-butyl ether |
| DMF | N,N-dimethylformamide |
| DMA | N,N-dimethylacetamide |
| DMSO | dimethyl sulfoxide |
| HOAc | acetic acid |
| TFA | trifluoroacetic acid |
| $Et_3N$ | triethylamine |
| DIPEA | diisopropylethylamine |
| DIEA | diisopropylethylamine |
| $K_2CO_3$ | potassium carbonate |
| $Na_2CO_3$ | sodium carbonate |
| $Cs_2CO_3$ | cesium carbonate |
| $NaHCO_3$ | sodium bicarbonate |
| NaOH | sodium hydroxide |
| $Na_2SO_4$ | sodium sulfate |
| $K_3PO_4$ | potassium phosphate |
| $NH_4Cl$ | ammonium chloride |
| LC/MS | liquid chromatography/mass spectra |
| HPLC | high performance liquid chromtagraphy |
| GC | gas chromatography |
| LC | liquid chromatography |
| Hr or h | hours |
| atm | atmospheres |
| rt or RT | room temperature |
| TLC | thin layer chromatography |
| HCl | hydrochloric acid |
| $H_2O$ | water |
| EtNCO | ethyl isocyanate |
| Pd/C | palladium on carbon |
| NaOAc | sodium acetate |
| $H_2SO_4$ | sulfuric acid |
| $N_2$ | nitrogen gas |
| $H_2$ | hydrogen gas |
| n-BuLi | n-butyl lithium |
| Piv | pivaloyl |
| DI | de-ionized |
| $Pd(OAc)_2$ | palladium(II)acetate |
| $PPh_3$ | triphenylphosphine |
| i-PrOH | isopropyl alcohol |
| NBS | N-bromosuccinimide |
| $Pd[(Ph_3)P]_4$ | tetrakis(triphenylphosphine)palladium(0) |
| PTFE | polytetrafluoroethylene |
| NLT | not less than |
| NMT | not more than |
| rpm | revolutions per minute |
| SM | starting material |
| Equiv. | equivalents |
| $^1$H-NMR | proton nuclear magnetic resonance |
| ss$^{13}$C-NMR | solid state carbon nuclear magnetic resonance |
| TGA | thermal gravimetric analysis |
| DSC | differential scanning calorimetry |
| MIK | methyl isopropyl ketone |

As used herein, other abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997, herein incorporated in its entirety by reference.

Scheme 1:

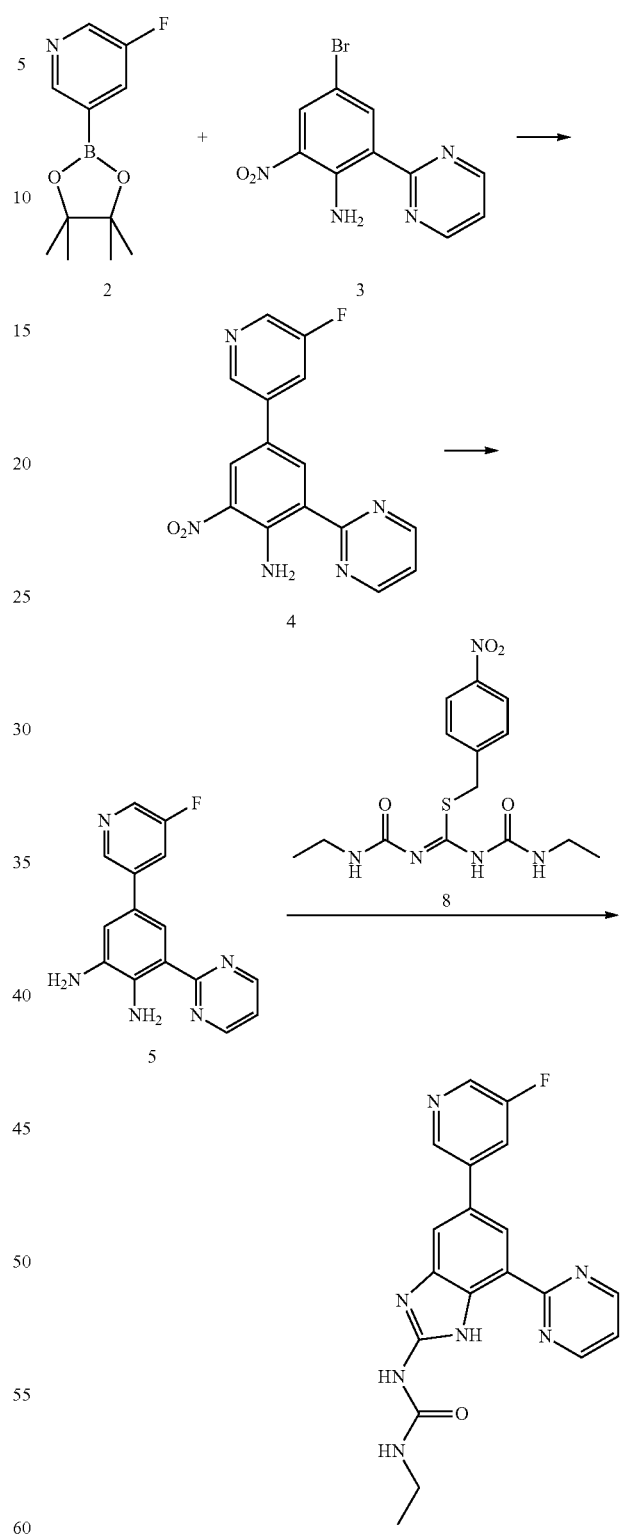

In scheme 1, compound 2 is prepared from 3-bromo-5-fluoropyridine (Scheme 3 below) or alternatively purchased commercially (e.g., HonestJoy (CAS #719268-92-5)). Compound 3 may be prepared according to scheme 4 below and the experimental procedures described below. Alternatively, compound 3 may be prepared according to the procedures described in WO 05/012292 which is hereby incorporated by reference. Boronate of formula 2 is cross coupled with aryl bromide of formula 3 in a biphasic mixture of aqueous inorganic base (e.g., an alkali metal base such as potassium carbonate or potassium phosphate) and a suitable organic solvent (e.g., 1,2-dimethoxyethane or ethanol) with a suitable transition-metal catalyst (e.g., palladium(II)acetate), a suitable phosphine catalyst (e.g., triphenylphosphine) and a suitable phase transfer catalyst (e.g., cetyltrimethylammonium bromide) at a suitable temperature (e.g., between 40° C. to 120° C.) to yield a compound of formula 4. Conversion of the nitro group in the compound of formula 4 to the aniline may be achieved under reducing conditions (e.g., a suitable hydrogen atmosphere in the presence of a palladium catalyst) in a suitable solvent (e.g., N,N-dimethylacetamide) to give the desired diamine of formula 5. The diamine of formula 5 in an acidic aqueous solution (e.g., sodium acetate in water with the pH adjusted to between 3 to 4 with a suitable acid such as, for example, concentrated sulfuric acid) is reacted with a solution of compound of formula 8 in an organic solvent (e.g., 1,2-dimethoxyethane) at a suitable temperature (e.g., between 40° C.-120° C.) to give compound 1. Compound 8 may be prepared according to scheme 2 below and the experimental procedures described below.

Scheme 2:

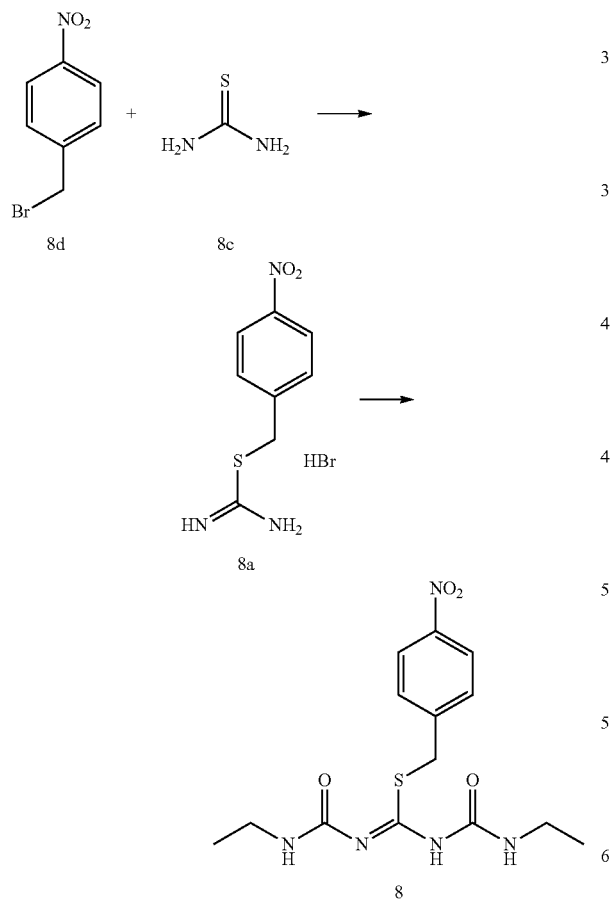

In scheme 2, isothiourea of formula 8a is prepared by addition of thiourea of formula 8c in a suitable solvent (e.g., acetone) to a mixture of the bromide of formula 8d in a suitable solvent (e.g., acetone). Treatment of isothiourea of formula 8a with excess ethylisocyanate in a suitable mixture of water and an organic solvent (e.g., 1,2-dimethoxyethane) afforded the pseudothiourea of formula 8.

Scheme 3:

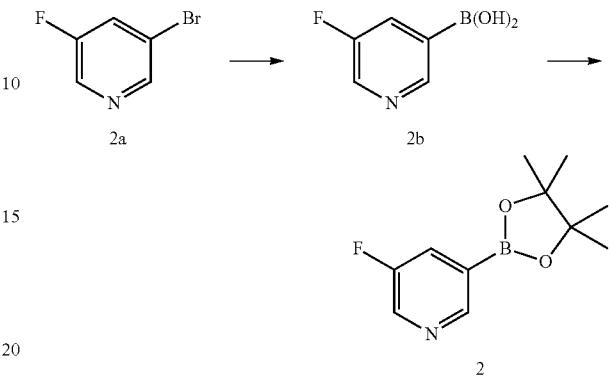

In scheme 3, the boronic acid of formula 2b is prepared by reaction of commercially available 3-bromo-5-fluoropyridine of formula 2a with a strong lithium base (e.g., n-butyl lithium) in the presence of a borate ester (e.g., isopropyl borate) in a suitable aprotic solvent (e.g., tetrahydrofuran). Subsequently, the intermediate borate ester mixture is quenched and hydrolyzed with an aqueous mineral acid (e.g., 9% aqueous HCl) to give boronic acid 2b. Subsequently, the boronic acid of formula 2b is esterified with pinacolate alcohol in a suitable solvent (e.g., toluene) at an elevated temperature of between 80° C. to 150° C. to give the compound of formula 2.

Scheme 4:

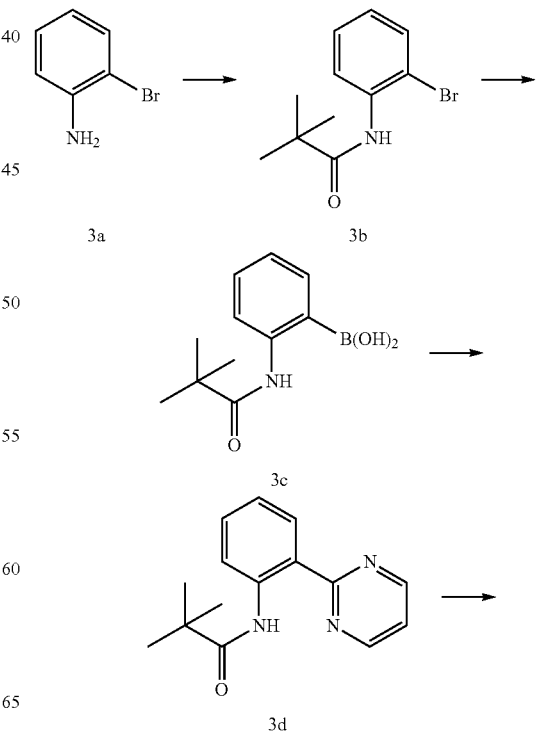

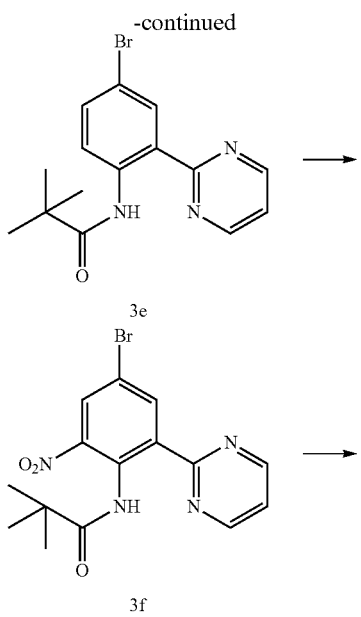

3e

3f

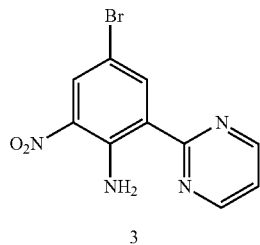

3

Referring to scheme 4, the pivalamide of formula 3b is prepared by treating a bromoaniline of formula 3a with pivaloylchloride in a suitable aprotic solvent (e.g., dichloromethane) in the presence of a suitable base (e.g., an organic tertiary amine base such as triethylamine) at temperatures between –20° C. and 25° C. Preparation of the corresponding boronic acid of formula 3c is achieved by reacting a bromide of formula 3b with a strong lithium base (e.g., n-butyl lithium) in a suitable aprotic solvent (e.g., tetrahydrofuran) followed by addition of a suitable borate ester (e.g., isopropylborate) at a suitable temperature (e.g., –45° C. to –100° C.). Biaryl intermediate 3d is prepared by cross coupling reaction of boronic acid 3c with 2-chloropyrimidine in a biphasic mixture of aqueous inorganic base (e.g., an alkali metal base such as sodium carbonate) and a suitable organic solvent (e.g., glycol dimethyl ether) with a suitable transition-metal catalyst (e.g., tetrakis(triphenylphosphine)palladium(0)) at a suitable temperature (e.g., between 25° C. to 120° C.). Compound of formula 3d is then brominated with a suitable brominating reagent (e.g., NBS or N-bromosuccinimide) in glacial acetic acid at a suitable temperature (e.g., 25° C. to 80° C.) to provide aryl bromide of formula 3e. Nitration of 3e is accomplished by reacting a cooled aqueous solution (e.g., between –20° C. to 10° C.) of 3e in a suitable acid (e.g., sulfuric acid) with nitric acid to provide a compound of formula 3f. Removal of the pivaloyl protecting group is achieved with a suitable acid (e.g., hydrochloric acid) in an organic solvent (e.g., absolute ethanol) at a suitable temperature (e.g., between 30° C. to 120° C.) to yield a compound of formula 3.

Experimental Procedures

Preparation of 5-Fluoropyridine-3-boronic acid (2b): 3-bromo-5-fluoropyridine (2a) (25 kg, 142 moles, 1.0 equiv.), THF (222.5 kg) and isopropyl borate (28 kg, 149.3 moles, 1.05 equiv.) were added to a 700 L low temperature reactor. The resulting mixture was cooled to –90° C.~–80° C. while stirred. Then n-BuLi (40.2 kg, 2.5 M, 142 moles, 1.0 equiv.) was added dropwise (2 kg/h) maintaining the temperature below –87° C. After the addition was complete, the mixture was maintained at –88~–83° C. for 2.5 h. When the reaction was deemed complete by HPLC analysis, it was quenched by addition of 9% aqueous HCl (7.7 kg). The mixture was transferred to a 1000 L glass-lined reactor and the temperature returned to –20~–10° C. Additional HCl solution (122.3 kg) was then added until pH was adjusted to 1~2 maintaining the temperature at 0~10° C. The mixture was then held for 0.5 h in order to allow layers to separate. The organic layer was separated and washed with saturated brine (38 kg). It was stirred for 0.5 h and then held again for 0.5 h to allow layer separation. The aqueous layer was separated and the combined aqueous layers were extracted with EtOAc twice (51+ 25 kg). The organic phase was separated and pH was adjusted to a value of 6 by using 30% aqueous NaOH solution (27.4 kg). At this pH a solid precipitated out. The slurry was filtered by centrifuge and allowed to dry in a tray dryer at 40~45° C. Title compound (2b) was obtained as a white solid (17.5 kg, 87.4%, purity: 98.6% AUC using method B).

Preparation of 5-Fluoropyridine-3-boronic acid pinacolate (2): Toluene (20 L/kg) followed by 5-fluoropyridine-3-boronic acid (2a) (19.45 kg, 138 moles, 1.0 equiv.) and pinacolate alcohol (16.3 kg, 138 moles, 1.0 equiv) were added to a 1000 L glass-lined reactor The resulting mixture was heated to 114~118° C. and maintained at the same temperature for 21 h. The reaction was monitored by TLC until no SM was detected. Then the mixture was cooled to 80° C. and continued to be cooled to 20~25° C. At this point it was filtered using a vacuum filter. The filtrate was concentrated under vacuum at T≦80° C. and P<–0.08 MPa until no fraction distilled out. Then, after cooling the mixture to 60° C., cyclohexane (27.4 kg) was added and the mixture evaporated again under the same conditions until no distillation observed. Maintaining the temperature at 55~65° C., isopropyl alcohol (20.8 kg) was added and the resulting mixture was heated to 70~80° C. and the product was allowed to crystallize at 5~15° C. for 12 h. The resulting slurry was filtered and the filtration cake was allowed to dry in a tray dryer at 37~43° C., furnishing the product as a white solid (25 kg, 81.2%, purity: 98% AUC determined by method C). Typical retention time for product (2) was 9.6 min. $^1$H NMR (CDCl$_3$, 300 MHz): δ 8.75 (1H, s), 8.53 (1H, d), 7.75 (1H, m), 1.96 (12H, s) ppm.

Preparation of 2-(4-Nitrobenzyl)isothiourea hydrobromide (8a): Thiourea (8c) (1.55 kg) and acetone (30 L) were added to a 72-L reactor under a nitrogen atmosphere. The mixture was agitated. 4-nitrophenylmethyl bromide (8d) (4.00 kg) and acetone (15 L) were added to a separate flask. The mixture was stirred until the bromide dissolved (warming may be required). The solution of the bromide was added to the mixture of thiourea, keeping the temperature below 40° C. A thick solution formed within 30 minutes. After stiffing for 2 h, HPLC analysis of the mixture shows >99% conversion. The mixture was filtered, and the filter cake was rinsed with a 1:1 MTBE: acetone solution (8 L). The solids were dried to give 5.09 kg (93% yield) of the desired product (8a) as a white solid.

Preparation of N,N-Diethylureamido-2-(4-nitrobenzyl)-2-thiopseudourea (8): 2-(4-nitrobenzyl) isothiourea hydrobromide (8a) (748 g, 2.56 moles, 1.0 equiv.), water (1.0 L, 1.4 vol) and DME (2 L, 2.8 L) were charged into a 10 L Morton flask that was equipped with an overhead stirrer and a thermocouple. Ethyl isocyanate (800 mL, 10.2 moles, 4.0 equiv.) was added to the cleared yellow solution and the resulting biphasic mixture (EtNCO layer and a water/DME layer) was stirred vigorously at 15~25° C. for 21-24 hours. At the end of the reaction the mixture is comprised of a clear and colorless top aqueous layer and a clear and yellow bottom organic layer. The aqueous layer was removed and DME (2 L, 2.8 vol) was added into the Morton flask, then concentrated to 2.8 vol at 35~40° C. under vacuum pressure. This distillation was repeated one additional time then the remaining mixture containing compound of formula (8) was used directly in the next step. Before running the next step, the mixture was analyzed (method H) to make sure all the isocyanate had been removed (if this is not the case, additional distillations might be needed).

Alternative isolation of N,N-diethylureamido-2-(4-nitrobenzyl)-2-thiopseudourea (8): To a suspension of 2-(4-nitrobenzyl)isothiourea hydrobromide (8a) (2.15 g, 7.33 mmol) in pH 7.0 buffer solution (3.0 mL) and 1,2-dimethoxyethane (4.0 mL) was added ethyl isocyanate (2.40 mL, 30.6 mmol). The biphasic solution was allowed to stir for 18 hours, at which point a white suspension was observed. The solids were filtered. The filter cake was washed with water then diethyl ether to afford the title compound (8) after air drying as a white solid (1.76 g, 68%). The title compound exists as a mixture of rotamers. $^1$H NMR: δ 12.00 (bs, 1NH), 8.15 (d, 2H, J=8.1 Hz), 7.95 bs, 1NH), 7.69 (d, 2H, J=8.3 Hz), 7.64 (app t, 1NH), 4.29 (s, 2H), 3.10 (quintet, 2H, J=6.6 Hz), 3.01 (quintet, 2H, J=7.0 Hz), 1.07 (t, 3H, J=7.1 Hz), 1.00 (t, 3H, J=7.2 Hz) ppm.

Preparation of N-(2-bromophenyl)pivalamide (3b): DCM (670 Kg) and Et$_3$N (76.4 Kg) were added to a 1000 L glass-lined reactor at 0° C. Then, 2-bromoaniline (3a) (100 Kg, 581 moles, 1.0 equiv.) was added with stirring. The resulting mixture was cooled to 0~10° C. and pivaloyl chloride (77.1 kg, 640 moles, 1.1 equiv.) was added dropwise (5 kg/h) while maintaining the same temperature. The mixture was stirred at this temperature for 1 h 25 min and reaction progress monitored by HPLC. When it was deemed complete, the reaction was quenched by addition of a 5% aqueous solution of Na$_2$CO$_3$ (120 kg) at a rate of 2 kg/min. After addition, the mixture was stirred for 1.5 h and the pH value tested to be between 7 and 8. The reaction was allowed to stand for 20-30 min and the organic phase was separated out. The aqueous layer was extracted with DCM twice (60×2 kg). During each extraction, the bi-phasic mixture was stirred for 15-20 min and then held for 15~20° C. to allow for layer separation. All the organic layers were combined and a 3% aqueous solution of HCl (251.8 kg) was added to adjust the pH value between 5 and 6. Then the aqueous layer was separated and the organic layer was washed with saturated NaHCO$_3$ (150 L). During the washing, the bi-phasic mixture was stirred for 30 min and held for 30 min. The organic phase was separated and dried over NaSO$_4$ (50 kg) with stirring for 13 h. The resulting slurry was filtered under vacuum using a 50 L vacuum filter. The filtration cake was washed with DCM twice (25 kg×2). The filtrate was concentrated by evaporation at T<50° C. under atmospheric pressure until no solvent distilled out. Then it was additionally concentrated by evaporation under vacuum (P≦MPa) at 65~70° C. After concentration, the mixture was cooled to 55~60° C. and THF was added (993 kg). Then the mixture was concentrated by evaporation again under the same conditions as above. The content of DCM was monitored by GC using method F until <0.1%. The mixture was cooled to 20~30° C. under N$_2$ and then filtered though silica gel (8 kg) under vacuum in order to dry it. The silica plug was washed twice with THF (20 kg×2) to give a solution of crude (3b) which was transferred into 200 L drums for the following step. Typical retention time for starting material (3a) is 8.0 min and for product (3b) is 8.9 min.

Preparation of N-(2,2-Dimethyl-propionamide)-1-phenylboronic acid (3c): In a 1500 L titanium reactor, under N$_2$, the above solution of N-(2-bromophenyl)pivalamide (3b) in THF (278 kg) was mixed with THF (102.7 kg). With stiffing, the resulting solution was cooled to −65~−70° C. Then n-BuLi (2.5 M, 73.4 kg, 2.4 equiv.) was added dropwise (2.5/3.0 kg/h) while keeping the same temperature range. After addition, the reaction was stirred at this temperature for 45 min. The remaining n-BuLi (73.4 kg) was then added and after the second addition, the mixture was stirred at −60~−70° C. for 1 h. The reaction was monitored by HPLC until a lithiation ratio of >96% was detected. Then isopropylborate (105.9 kg, 563 moles, 2.6 equiv.) was added at the rate of 10-15 kg/h at −60~−70° C. The resulting mixture was stirred at the same temperature for 4 h 20 min. The reaction was monitored by HPLC until completion. The reaction mixture was quenched by addition of petroleum ether (241.2 kg) and allowed to warm to 0~5° C. and maintained at this temperature for 2 h. The resulting mixture was washed-filtered by centrifuge and the cake washed with saturated aqueous NH$_4$Cl (159 kg) under stiffing for 1 h. Then the washing mixture was also filtered with centrifuge and the combined filtrates were concentrated under vacuum at T≦35° C. and P≦−0.09 MPa until no fraction distilled out. Then the mixture was cooled to 27° C. and centrifuged again. The cake was washed with water (150 kg) for 0.5-1 h and centrifuged once more. The cake was washed with MTBE (114 kg) for 0.5-1 h and filtered with centrifugation. After drying the boronic acid (3c) was obtained as an off-white solid (51 kg, 98.6%). Typical retention time for SM (3b) was 2.3 min.

Preparation of N-(2-Pyrimidin-2-yl)phenyl)pivalamide (3d): To a 500 L glass-lined reactor, under N$_2$, was added glycol dimethyl ether (152.3 kg, 5 L/kg). Then 2-chloropyrimidine (18.4 kg, 160 moles, 1.01 equiv.) was added with stirring, followed by Pd[(Ph$_3$)P]$_4$ (3.65 kg, 3.2 moles, 0.02 equiv.). The resulting mixture was stirred at 15~25° C. for 20-30 min and then N-(2,2-dimethyl-1-propinamide)1-phenyl-boronic acid (3c) (35 Kg of product, containing additional 11 kg of salts, 158 moles, 1.0 equiv.) was added in one portion. After addition, aqueous Na$_2$CO$_3$ solution (132.8 kg, 2 M) was added quickly and the mixture heated to 78~83° C. and refluxed for 3 h. The reaction was monitored by HPLC using method H until SM (3c) was <3%. The mixture was then slightly cooled to 70~75° C., quenched by addition of cold purified water (5~10° C., 525 kg) and stirring continued at 0~10° C. for 1-2 h. The mixture was then filtered by centrifuge and the cake washed with purified water. The wet product from 4 batches (7, 35, and 35 kg scale) was combined and dried on a tray dryer for a week and then on a rotary conical dryer but some water (at least 3% weight) could not be removed. The title compound (3d) was obtained as a yellow wet solid (157 kg, >100%, purity >98% determined by method F). Typical retention time for product was 15.9 min.

Preparation of N-(4-Bromo-2-(pyrimidin-2-yl)pivalamide (3e): Acetic acid (367.5 kg) was charged to a 500 L reactor. Then, N-(2-(pyrimidin-2-yl)phenyl)pivalamide (3d) (35 kg of product, contained water, 137.3 moles, 1.0 equiv.) was added followed by NBS (26.9 kg, 151.1 moles, 1.1 equiv.). The resulting mixture was heated to 50~55° C. and stirred for 5 h. The reaction progress was monitored by HPLC (method I) until (3d) was <2%. The reaction was quenched by pouring onto purified water (350 kg) which had previously been cooled to 0~5° C. The mixture was maintained at 0~10° C. under stirring for 1-2 h. The mixture was then filtered via a centrifuge. The combined cake from 3 batches (from 35 kg of 3d each) was washed with purified water twice (550+500 kg) under stirring for 0.5-1 h. After a second filtration with centrifuge and drying, the title product (3e) was obtained as a light yellow solid (105.6 kg, 80%, 80%, purity: 99.3% determined by analytical method G). Typical retention time for SM (3d) was 7.5 min, for product (3e) was 15.1 min.

Preparation of N-(4-bromo-2-nitro-6-pyrimidin-2-yl)phenyl)pivalamide (3f)

Water (7.4 Kg) was charged to a 200 L reactor. Upon cooling to 0~5° C., conc. $H_2SO_4$ (138 kg, 98%, 3.77 L/kg) was added at a temperature T<30° C. The resulting mixture was cooled to 0~5° C. again and N-(4-bromo-2-pyrimidin-2-yl)phenyl)pivalamide (3e) (20 kg, 59.8 moles, 1.0 equiv.) was added in 4 portions keeping the temperature constant. After addition, the mixture was stirred at 5~10° C. for 0.5-1 h until the solid dissolved completely. After cooling to −10~−5° C., $HNO_3$ (12 kg, 98%, 0.4 L/kg) was added dropwise (2 kg/h) maintaining this temperature. After addition the mixture was stirred at the same temp. for 30 min. The reaction progress was monitored by TLC until no SM (3e) could be detected. While maintaining the temperature at −10~−0° C. the reaction was quenched by pouring it onto a mixture of crushed ice (280 kg) and tap water (420 kg) in a 1000 L glassed-lined reactor. The mixture was then maintained at 0~10° C. for 0.5-1 h. The mixture was filtered with centrifuge and the cake was washed until its pH was between 6 and 7. The resulting product was dried at 50~60° C. The crude products from several batches (3×20 kg scale) were combined and dissolved in DCM (469 kg), dried over $Na_2SO_4$ (25 kg) under stirring for 4 h and press-filtered through silica gel (40 kg). The silica plug was washed with DCM twice (90 kg×2) and the combined filtrates were concentrated under vacuum at T<50° C. to remove the solvent. Petroleum ether was then added (141.7 kg) and the solution concentrated again at 40~50° C. until no fraction distilled out. The resulting crude was filtered via a centrifuge. The cakes were combined furnishing the title compound (3f) as a grayish brown solid (62 kg, 91%, purity: >92.7% as determined by method G). Typical retention time for product (3f) was 11.3 min.

Preparation of 4-bromo-2-nitro-6-pyrimidin-2-yl-phenylamine (3): EtOH (87.4 kg, 3.12 kg/kg) was charged to a 500 L vessel. With stirring, a solution of HCl in EtOH (168 kg, 35%, 6 kg/kg) was then added. Finally, N-(4-bromo-2-nitro-6-pyrimidin-2-yl)phenyl)pivalamide (3f) (28 kg, 73.8 moles, 1.0 equiv.) was added in one portion. After addition, the mixture was heated to 80~88° C. and refluxed for 49 h. The reaction progress was monitored by HPLC (method I) until (3f) was ≦3%. Additional HCl/EtOH solution (50.5 kg) was added and the mixture continued to be refluxed for an additional 9.5 h. The mixture was cooled to 30~40° C. and quenched by pouring it onto cold purified water (280 kg). The mixture was filtered with centrifuge and the cake was washed with water twice under stirring for 1 h (450 kg×2). The resulting solid was dried at 40~50° C. under $N_2$, to furnish the title compound (3) as a brownish yellow solid (20.9 kg, 96%, purity: 99.0% determined by method G). Typical retention time for (3) was 10.1 min. $^1H$ NMR ($CDCl_3$, 300 MHz): δ 9.00 (1H, d), 8.85 (1H, d), 8.46 (1H, d), 7.29 (2H, m) ppm.

Preparation of 4-(5-Fluoropyridin-3-yl)-2-nitro-6-(pyrimidin-2-yl)benzenamine (4): A 3 L round-bottom flask was fitted with a mechanical overhead stirrer, a reflux condenser, and a thermometer and purged with $N_2$. 3-Fluoro-5-(4,4,5,5-tetramethyl-1,3,2-dioxaborolan-2-yl)pyridine (2) (95.0 g, 421 mmol, 1.2 equiv), 4-bromo-2-nitro-6-(pyrimidin-2-yl) benzenamine (3) (104.55 g, 354 mmol, 1.0 equiv), $K_3PO_4$ (93.1 g, 438 mmol, 1.25 equiv, Riedel-deHaen #S29375-366), $Pd(OAc)_2$ (0.80 g, 3.5 mmol, 1 mol %, Aldrich #06410JE) cetyltrimethylammonium bromide (1.28 g, 3.5 mmol, 1 mol %, Aldrich #0823CE) and $PPh_3$ (3.74 g, 14 mmol, 4 mol %, Fluka #1093859) were added followed by EtOH (10 vols) and water (1.1 vols). The heterogeneous reaction mixture was stirred vigorously (>300 rpm) and heated to reflux (80° C.). After 6 hours a sample was removed for analysis of reaction completion (method C). After the reaction was judged complete, the mixture was cooled to 30° C., then water (10 vol) was added and the reaction stirred for 2 h. The resulting slurry was filtered and the filter cake washed with water (2×5 vol) and acetonitrile (2×5 vol). The filter cake was then charged back to the flask and water added (10 vol). The slurry was stirred for 3 h at 30° C. and filtered again. The filter cake was then transferred to a dish and allowed to dry under vacuum at 60-80° C. for 12 h furnishing compound (4) as an orange powder (104.87 g, 88%, purity: 96.14% AUC determined using method A). Typical reaction times were 7.9 min for SM (2) and 6.9 min for product (4).

Preparation of 5-(5-Fluoropyridin-3-yl)-3-(pyrimidin-2-yl)benzene-1,2-diamine (5): To a 20 L Büchi hydrogenator equipped with a Büchi gas controller and a Huber temperature controller was added 4-(5-fluoropyridin-3-yl)-2-nitro-6-(pyrimidin-2-yl)benzenamine (4) (1095 g, 3.581 mol, 1.00 equiv.), 5% Pd/C (438 g, 50% wet) and DMAc (N,N-dimethylacetamide, 11.0 L, 10 vol). The reactor was purged with nitrogen gas (3 times), then hydrogen gas (3 times). The reaction temperature was set to 23° C. and the pressure of the reactor was set to 50 psi with hydrogen gas. The mixture was agitated at 1350 rpm. The reaction progress was monitored by the hydrogen uptake curve that started to flatten out after 1.7 hours. The hydrogenation was continued for an additional 2 hours. The reactor with purged with nitrogen gas (3 times). Removed an aliquot and analyzed it by HPLC (method A) to obtain NMT 1% AUC of (4). The hydrogenation was continued for another 0.5 h, followed by pressure release and $N_2$ purge (3 times). The reaction mixture was filtered through a pad of celite (400 g, wetted with 1.50 L of DMAc) and a #3 Whatman filter paper. The hydrogenator was washed with DMAc (1.10 L) and filtered through the celite pad. The filter cake was washed with 0.300 L of DMAc. The resulting filtrates were combined and treated with activated carbon twice (493 g each). After the second wash, the charcoal was removed by filtration, and the filtrate filtered through #3 filter papers. Water (20.0 L) was slowly added to maintain a temperature of NMT 40° C. and a yellow solid precipitated out. Filtered the slurry through a #3 Whatman filter paper at room temperature and washed the yellow solid with 6.0 L of water. The yellow solid was dried in a vacuum oven at 60° C. under vacuum to afford the title compound (5) as a white powder (671 g, 68%, 99.2% AUC using method A). Typical retention times are 7.08 min for SM (4) and 5.03 min for product (5).

Preparation of 1-Ethyl-3-(5-(5-fluoropyridin-3-yl)-7-(pyrimidin-2-yl)-1H-benzo[d]imidazol-2-yl)urea (6), form IA: NaOAc (1040 g, 12.7 moles, 6.0 equiv.) and water (16 L, 10.5 vol) were charged to a 22 L Morton flask equipped with an overhead stirrer, a pH probe, a thermocouple and two reflux condensers. The pH reading of this solution was 8.3. A concentrated solution of $H_2SO_4$ (328 mL, 3.94 moles, 0.547 vol) was added until the pH reading of the solution was 3.5. Then 5-(5-fluoropyridin-3-yl)-3-(pyrimidin-2-yl)benzene-1,2-diamine (5) (600 g, 2.13 moles, 1.0 equiv.) was added. The DME solution of (8) (1.2 equiv.) obtained as above in Example 3 was then added directly to the yellow suspension. This heterogeneous mixture was stirred vigorously (200-250 rpm) and heated to reflux (80° C.). During the course of the reaction, the yellow suspension first transformed into a dark yellow suspension, then into a tan suspension. After 4 h, the reaction mixture was cooled to 22~35° C. The tan suspension was filtered and the filter cake was washed with water (8×2 L), EtOAc (5×4 L), and dried at 40-50° C. under vacuum to provide compound (6) as a beige powder (747 g, 93%, purity: 99.32% AUC by method A). Typical retention times: pseudo-isothiourea intermediate (8) 7.3 min, product (6) 6.3 min, SM (5) 5.4 min.

Various physical characteristics of form IA were evaluated using the following analytical methods:

X-Ray Powder Diffraction (XRPD): The XRPD pattern of form IA was recorded at room temperature in reflection mode using Bruker D8 Discover system equipped with a sealed tube source and a Hi-Star area detector (Bruker AXS, Madison, Wis.). The X-Ray generator was operating at a tension of 40 kV and a current of 35 mA. The powder sample was placed on a Si zero-background wafer. Two frames were registered with an exposure time of 120 s each. The data were subsequently integrated over the range of 3°-41° 2 with a step size of 0.02° and merged into one continuous pattern. An exemplary XRPD of form IA is provided in FIG. 2.

Differential Scanning Calorimetry (DSC): DSC was performed on a sample of form IA using a DSC 2920 differential scanning calorimeter (TA Instruments, New Castle, Del.). The instrument was calibrated with indium. A sample of approximately 1-2 mg was weighed into an aluminum pan that was crimped using lids with either no pin-hole or four pin-holes. The DSC samples were scanned from 25° C. to 275° C. at a heating rate of 10° C./min. Data was collected by Thermal Advantage Q Series™ software and analyzed by Universal Analysis software (TA Instruments, New Castle, Del.). A representative DSC trace of form IA is provided in FIG. 3. Only one sharp endothermic event corresponding to the melting of form IA was seen in the DSC data. The melting point was high, ~270° C. The compound degraded upon melting as observed in TGA.

Thermogravimetric analysis (TGA): A Model Q500 Thermogravimetric Analyzer (TA Instruments, New Castle, Del.) was used for TGA measurement. A sample of form IA with weight of approximately 3-5 mg was scanned from 25° C. to 300° C. at a heating rate of 10° C./min. Data was collected by Thermal Advantage Q Series™ software and analyzed by Universal Analysis software (TA Instruments, New Castle, Del.). An exemplary TGA trace of form IA is provided in FIG. 4. TGA data show a weight loss of ~0.8% when form IA powder was heated from room temperature up to ~175° C. at a rate of 10° C./min. The dramatic decrease in the sample weight which begins at ~200° C. was associated with the sample degradation. Comparison with the DSC data described above shows that the compound degraded upon melting.

Dynamic Vapor Sorption (DVS): A step isothermal study (25° C.) was conducted on a representative sample of form IA using a VTI SGA 100 Symmetric Vapor Sorption Analyzer. An aliquot of approximately 10 mg was weighed in an open platinum dish and exposed to different levels of humidity at 25° C. Relative humidity (RH) steps were from 5% to 95% (adsorption) and from 95% to 5% in increments of 5% RH (desorption). The equilibration criterion was 0.0100 wt % change in 5 min, with a max equilibration time of 180 min. An exemplary DVS trace of form IA is provided in FIG. 5. The sample picked up ~8 wt % moisture at 95% relative humidity (RH). All adsorbed water was released in the desorption stage. The compound did not form a hydrate. These data indicate that this compound has moderate hygroscopicity.

ss$^{13}$C-NMR: A ss$^{13}$C-NMR spectra of form IA was obtained using a 4500 Hz MAS instrument, which was zeroed by collecting a spectrum just prior to the sample using hexamethylbenzene. The methyl peak of hexamethylbenzene was calibrated to 17.35 ppm before the sample was run. An exemplary ss$^{13}$C-NMR spectra of form IA is provided in FIG. 6.

Solubility: The solubility of form IA in various media was determined at ambient conditions by equilibrating aliquots of the drug powder with the solvents on a shaking bed for 24 hours. The samples were centrifuged, the saturated solutions of the drug were then separated and analyzed by HPLC. The sample volume was 100 μL and the target concentration was 10 mg/mL. The saturated solutions were diluted appropriately and analyzed by HPLC. Solubility data for was obtained using an HPLC method (HPLC column: Waters C18, 3.5 μm, 75 mm; flow 1.7 mL/min, mobile phase: mixture of A (85% water containing 0.1% $H_3PO_4$) and B (15% acetonitrile containing 0.1% $H_3PO_4$), gradient method was used: gradient from 15 to 35% of B over 6 min, then gradient 35-15% of B over 30 s and then hold at 15% B for 1.5 min; retention time: 4.0 min, wavelength: 284 nm. Tables 9 and 10 below provide representative solubility of form IA in various exemplary solvent systems. The data provided in Tables 9 and 10 are representative. Some variability may occur between lots of a particular sample, e.g., about 10%).

TABLE 9

Solubility of form IA in various aqueous and organic media

| Media | Form IA (mg/mL) | pH |
|---|---|---|
| 0.1N HCL | 13.678 | 1.29 |
| Octanol | 0.175 | NA |
| Deionized Water | <0.001 | 7.14 |
| Tris buffer, pH 7 (1.0M) | <0.001 | 7.20 |
| PEG 400 | 1.621 | 7.54 |
| Propylene Glycol | 0.359 | 6.04 |
| Ethanol | 0.056 | 6.71 |
| Miglyol 810 | 0.017 | NA |
| 10% Vit E TPGS | 0.087 | 5.57 |
| 10% Cremophor EL | 0.066 | 6.48 |
| 1% SLS (Sodium Lauryl Sulfate) | 0.075 | 7.87 |
| 10% Tween 80 | 0.067 | 6.22 |
| 1% Tween80 in water | 0.01 | NA |
| Ethanol | 0.22 | NA |
| 10% Cremophor in water | 0.08 | NA |
| USP recipe-SGF (Simulated Gastric Fluid) | 4.92 | NA |
| Dressman's recipe 1-Fed SIF (Simulated Intestinal Fluid) | 0.01 | NA |
| Dressman's recipe 1-Fasted SIF | <0.001 | NA |
| D5W (Dextrose 5% in water) | <0.001 | NA |
| PBS (Phosphate Buffer Saline) | <0.001 | NA |

*NA means not available due to technical problems with the small pH probe

TABLE 10

Solubility of form IA in 0.05M Buffers at Different pH

| Medium | pH | VX-883 FB Lot 3 (mg/mL) |
|---|---|---|
| Potassium chloride hydrochloric acid | 1 | 2.24 |
| Potassium biphthalate sodium hydroxide | 3 | 0.07 |
| Potassium biphthalate sodium hydroxide | 5 | <0.001 |
| Potassium phosphate monobasic-sodium hydroxide | 7 | <0.001 |
| Potassium phosphate monobasic-sodium hydroxide | 9 | <0.001 |

Example 3

Physical Characterization of Form IIA

Form IIA was prepared using the following two crystallization procedures.

Procedure I: To a suspension of Compound 1 free base (173.5 mg) in EtOH/CH$_2$Cl$_2$ (1:1, 20 mL) was added ethanesulfonic acid (95% from Aldrich, 1.0 equiv., 38 µL). The mixture was stirred at ~45° C. until dissolution. The solution was then filtered, concentrated in vacuo and the resulting oily residue was redissolved in CH$_2$Cl$_2$ (10 mL) and the solution was added dropwise to a stirred solution of diethylether (~100 mL). The resulting off white precipitate was filtered, washed with diethylether under nitrogen and the solid was then dried overnight under high vacuum at ~40-45° C. to yield form IIA as a brown powder (174.6 mg): HPLC: Rt=4.92 min. (method: solvent B: 0.1% TFA/1% MeCN/water, solvent D: 0.1% TFA/MeCN. Gradient 10% D to 90% D over 8 min. at a flow rate of 1 mL/min. Method length 12 min. Column 1 (YMC 3×150). $^1$H NMR (CD$_3$OD, 500 MHz) 9.04 (d, J=4.9 Hz, 2H), 8.83 (q, J=1.6 Hz, 2H), 8.56 (d, J=2.6 Hz, 2H), 8.09-8.07 (m, 2H), 8.04 (d, J=1.6 Hz, 2H), 7.52 (t, J=4.9 Hz, 2H), 3.39 (q, J=7.3 Hz, 2H), 2.82 (q, J=7.4 Hz, 2H), 1.31 (t, 3H), 1.25 (t, 3H), 0.00 (TMS) ppm. MS (ES$^+$) m/z (M$^+$+1) 378.3.

Procedure II: To a suspension of Compound 1 free base (3.12 g) in EtOH/CH$_2$Cl$_2$ (1:1, 80 mL) was added ethanesulfonic acid (95% from Aldrich, 1.0 equiv., 677 µL). The mixture was stirred at ~40° C. until dissolution. The resulting dark solution was then filtered, concentrated in vacuo to ~10 mL, diluted with CH$_2$Cl$_2$ (30 mL) and the solution was added dropwise to a stirred solution of diethylether (~450 mL). The resulting off white precipitate was filtered, washed with diethylether under nitrogen and the solid was then dried overnight under high vacuum at 45° C. to yield form IIA as a beige powder (3.64 g): HPLC: Rt=4.80 min. (method: solvent B: 0.1% TFA/1% MeCN/water, solvent D: 0.1% TFA/MeCN. Gradient 10% D to 90% D over 8 min. at a flow rate of 1 mL/min. Method length 12 min. Column 1 (YMC 3×150). $^1$H NMR (CD$_3$OD, 500 MHz) 8.99 (d, J=4.9 Hz, H), 8.78 (t, J=1.5 Hz, H), 8.71 (d, J=1.6 Hz, H), 8.54 (d, J=2.6 Hz, H), 8.04 (dt, J=9.7, 2.2 Hz, H), 7.95 (d, J=1.6 Hz, H), 7.48 (t, J=4.9 Hz, H), 3.37 (q, J=7.3 Hz, H), 3.31 (qn, J=1.6 Hz, Methanol-d4), 2.87 (q, J=7.4 Hz, H), 1.34 (t, J=7.4 Hz, H), 1.25 (t, J=7.3 Hz, H) ppm. MS (ES$^+$) m/z (M$^+$+1) 378.14.

Various physical characteristics of form IIA were evaluated using the following analytical methods:

X-Ray Powder Diffraction (XRPD): The XRPD pattern of form IIA was recorded at room temperature with an X-ray generator (Rigaku/MSC RUH3R) and an X-ray detector (Rigaku/MSC Raxis IIC) in transmission mode. Radiation of Cu Kα at 50 KV×100 mA was used with 2θ increment rate of 1°/s. The scans run over a range of 0-40° 2 θ with a step size of 1° and a step time of 1 s. The powder samples were held in a 2 mm diameter capillary sample holder (Hampton Research, Laguna Niguel, Calif.). An exemplary XRPDXRPD of form IIA is provided in FIG. 7.

Differential Scanning Calorimetry (DSC): DSC was performed on a sample of form IIA using a DSC Q100 Differential Scanning Calorimeter (TA Instruments, New Castle, Del.). The instrument was calibrated with indium. Approximately 2 mg of sample was weighed into an aluminum pan. The pan was crimped with a lid that had a single pinhole. The DSC method used was a ramp of 10° C./min to 300° C. Data were collected using Thermal Advantage Q Series™ software and were analyzed by Universal Analysis Software. An exemplary DSC trace of form IIA is provided in FIG. 8. Only one sharp endothermic event was observed, corresponding to the melting of the compound. The melting point was ~216° C. The compound was determined to be degrading upon melting as also observed with TGA described below.

Thermogravimetric analysis (TGA): TGA measurements were performed on a sample of form IIA using a Model Q500 Thermogravimetric analyzer (TA Instruments, New Castle, Del.). A sample weight of approximately 3-8 mg was placed in platinum pans. The TGA method used was a ramp of 10° C./min to 300° C. Data were collected by Thermal Advantage Q Series software and analyzed by Universal Analysis Software. TGA data show a weight loss of ~0.5% when the drug powder was heated from room temperature up to ~180° C. at a rate of 10° C./min. An exemplary TGA trace of form IIA is provided in FIG. 9. The dramatic decrease in the sample weight which began at ~200° C. was associated with the sample degradation. Comparison with the DSC data shows that the compound degraded upon melting.

Dynamic Vapor Sorption (DVS): A step isothermal study (25° C.) was conducted on a sample of form IIA using a VTI SGA 100 Symmetric Vapor Sorption Analyzer. An aliquot of approximately 10 mg was weighed in an open platinum dish and exposed to different levels of humidity at 25° C. Relative humidity (RH) steps were from 5% to 95% (adsorption) and from 95% to 5% in increments of 5% RH (desorption). An exemplary DVS trace of form IIA is provided in FIG. 10. The equilibration criterion was 0.0100 wt % change in 5 min, with a max equilibration time of 180 min. The material picked up ~11 wt % moisture at 95% relative humidity (RH). Not all of the adsorbed water was released during the desorption phase.

Example 4

Physical Characterization of Form IIB

Form IIB was obtained by keeping form IA for 1 week at elevated temperature and humidity (40° C./75% RH) in an open container. Various physical characteristics of form IIB were evaluated using the following analytical methods:

X-Ray Powder Diffraction (XRPD): The XRPD pattern was recorded at room temperature with an X-ray generator (Rigaku/MSC RUH3R) and an X-ray detector (Rigaku/MSC Raxis IIC) in transmission mode. Radiation of Cu Kα at 50 KV×100 mA was used with 2θ increment rate of 1°/s. The scans run over a range of 0-40° 2 θ with a step size of 1° and a step time of 1 s. The powder samples were held in a 2 mm diameter capillary sample holder (Hampton Research, Laguna Niguel, Calif.). An exemplary XRPD of form IIB is provided in FIG. 11.

Differential Scanning Calorimetry (DSC): DSC was performed using a DSC Q100 Differential Scanning Calorimeter (TA Instruments, New Castle, Del.). The instrument was calibrated with indium. Approximately 2 mg of sample was weighed into an aluminum pan. The pan was crimped with a lid that had a single pinhole. The DSC method used was a ramp of 10° C./min to 300° C. Data was collected using Thermal Advantage Q Series™ software and was analyzed by Universal Analysis Software. An exemplary DSC trace of form IIB is provided in FIG. 12. Since there was no significant weight loss due to residual organic solvent recorded for the original material, the endothermic event observed at ~70° C. is associated primarily with water loss. The second sharp endothermic event seen at ~216° C. is associated with the melting transition.

Example 5

Physical Characterization of Form IIC

Form IIC was prepared by one of the following crystallization procedures.

To a suspension of Compound 1 free base (2.16 g) in EtOH/CH$_2$Cl$_2$ (1:1, 60 mL) was added ethanesulfonic acid (95% from Aldrich, 1.0 equiv., 491 µL). The mixture was stirred at ~40° C. until dissolution. The resulting dark solution was then filtered, concentrated in vacuo to ~10 mL, diluted with CH$_2$Cl$_2$ (30 mL) and the solution was added dropwise to a stirred solution of diethylether (~450 mL). The resulting off-white precipitate was filtered, dried under nitrogen (30 min.) to give VX-883-monoethanesulfonic acid as an off-white solid I (2.545 g). Solid I was used as the starting material in the following four procedures.

Procedure 1: Preparation of form IIC: A round bottom flask was charged with solid I (835 mg) and acetonitrile (106 mL). The suspension was stirred at ~40° C. for 10 min. Addition of deionized water (5 mL) solubilized the suspension. The resulting solution was then slowly stirred at room temperature and let slowly evaporate to dryness (over 6 days) under a slow flow of nitrogen. The residual solid was further dried under high vacuum (5 days) to yield form IIC as an off white solid (842 mg): HPLC: Rt=2.87 min. (method: solvent B: 0.1% TFA/1% MeCN/water, solvent D: 0.1% TFA/MeCN. Gradient 10% D to 90% D over 4 min. at a flow rate of 1 mL/min. Method length 7 min. Column 2 (Lighting, 3 um, 2.1 mm×50 mm). $^1$H NMR (CD$_3$OD, 500 MHz) 9.05-9.04 (m, 2H), 8.84 (dd, J=1.4, 4.2 Hz, 2H), 8.56 (d, J=2.5 Hz, 1H), 8.09 (d, J=9.5 Hz, 1H), 8.04 (d, J=1.4 Hz, 1H), 7.53 (m, 1H), 3.39 (q, J=7.3 Hz, 2H), 2.81 (q, J=7.4 Hz, 2H), 1.33-1.24 (m, 6H), ppm. MS (ES$^+$) m/z (M$^+$+1) 378.14.

Procedure 2: Preparation of form IIC: A round bottom flask was charged with solid I (830 mg) and methanol (46 mL). The solution was stirred at ~30° C. for 5 min. The clarified solution was then slowly stirred at room temperature and let slowly evaporate to dryness (over 7 days) under a slow flow of nitrogen. The residual solid was further dried under high vacuum (5 days) to yield form IIC as an off white solid (840 mg): HPLC: Rt=2.86 min. (method: solvent B: 0.1% TFA/1% MeCN/water, solvent D: 0.1% TFA/MeCN. Gradient 10% D to 90% D over 4 min. at a flow rate of 1 mL/min. Method length 7 min. Column 2 (Lighting, 3 um, 2.1 mm×50 mm). $^1$H NMR (CD$_3$OD, 500 MHz) 9.02 (d, J=3.3 Hz, 2H), 8.80 (d, J=13.0 Hz, 2H), 8.55 (s, 1H), 8.07 (d, J=9.5 Hz, 1H), 8.00 (s, 1H), 7.50 (m, 1H), 3.38 (q, J=7.2 Hz, 2H), 2.85 (q, J=6.8 Hz, 2H), 1.32 (t, J=7.4 Hz, 3H), 1.25 (t, J=7.2 Hz, 3H) ppm. MS (ES$^+$) m/z (M$^+$+1) 378.14.

Procedure 3: Preparation of form IIC: A round bottom flask was charged with solid I (880 mg), ethanol (41 mL), and methanol (27 mL). The suspension was stirred at ~40-45° C. for 10 min. The clarified solution was then slowly stirred at room temperature and let slowly evaporate to dryness (over 7 days) under a slow flow of nitrogen. The residual solid was further dried under high vacuum (5 days) to yield form IIC as an off-white solid (898 mg): HPLC: Rt=2.87 min. (method: solvent B: 0.1% TFA/1% MeCN/water, solvent D: 0.1% TFA/ MeCN. Gradient 10% D to 90% D over 4 min. at a flow rate of 1 mL/min. Method length 7 min. Column 2 (Lighting, 3 um, 2.1 mm×50 mm). $^1$H NMR (CD$_3$OD, 500 MHz) 9.02 (d, J=4.4 Hz, 2H), 8.81 (s, 1H), 8.78 (s, 1H), 8.55 (s, 1H), 8.06 (d, J=9.5 Hz, 1H), 8.00 (s, 1H), 7.50 (m, 1H), 3.38 (q, J=7.2 Hz, 2H), 2.85 (q, J=7.3 Hz, 2H), 1.32 (t, J=7.4 Hz, 3H), 1.25 (t, J=7.2 Hz, 3H) ppm. MS (ES$^+$) m/z (M$^+$+1) 378.14.

Procedure 4: Form IIC was prepared according to procedure 2 described above starting from 7.06 g of compound 1 free base and used ethanesulfonic acid (1.6 mL) and methanol (480 mL) to give 8.58 g of form IIC as a beige solid: HPLC: Rt=2.86 min. (method: solvent B: 0.1% TFA/1% MeCN/ water, solvent D: 0.1% TFA/MeCN. Gradient 10% D to 90% D over 4 min. at a flow rate of 1 mL/min. Method length 7 min. Column 2 (Lighting, 3 um, 2.1 mm×50 mm). $^1$H NMR (CD$_3$OD with DMSO-d$_6$, 500 MHz) 9.02 (d, J=4.8 Hz, H), 8.84 (s, H), 8.76 (d, J=1.5 Hz, H), 8.59 (d, J=2.5 Hz, H), 8.10 (dd, J=2.0, 9.7 Hz, H), 8.02 (d, J=1.4 Hz, H), 7.51 (t, J=4.9 Hz, H), 3.37 (q, J=7.2 Hz, H), 2.81 (q, J=7.4 Hz, H), 1.31-1.23 (m, H) ppm. MS (ES$^+$) m/z (M$^+$+1) 378.14.

Various physical characteristics of form IIC were evaluated using the following analytical methods:

X-Ray Powder Diffraction (XRPD): The XRPD pattern of form IIC was recorded at room temperature in reflection mode using Bruker D8 Discover system equipped with a sealed tube source and a Hi-Star area detector (Bruker AXS, Madison, Wis.). The X-Ray generator was operating at a tension of 40 kV and a current of 35 mA. The powder sample was placed on a Si zero-background wafer. Two frames were registered with an exposure time of 120 s each. The data were subsequently integrated over the range of 3°-41° 2θ with a step size of 0.02° and merged into one continuous pattern. An exemplary XRPD is provided in FIG. 13.

Differential Scanning Calorimetry (DSC): DSC was performed on a sample of form IIC using a DSC 2920 differential scanning calorimeter (TA Instruments, New Castle, Del.). The instrument was calibrated with indium. A sample of approximately 1-2 mg was weighed into an aluminum pan that was crimped using lids with either no pin-hole or four pin-holes. The DSC samples were scanned from 25° C. to 275° C. at a heating rate of 10° C./min. Data was collected by Thermal Advantage Q Series™ software and analyzed by Universal Analysis software (TA Instruments, New Castle, Del.). An exemplary DSC trace is provided in FIG. 14. Only one sharp endothermic event corresponding to the melting of the compound is seen in the DSC data. The melting point is ~220° C., with decomposition. The compound degraded upon melting (confirmed with TGA).

Thermogravimetric analysis (TGA): A Model Q500 Thermogravimetric Analyzer (TA Instruments, New Castle, Del.) was used for TGA measurement. A sample of form IIC with weight of approximately 3-5 mg was scanned from 25° C. to 300° C. at a heating rate of 10° C./min. Data was collected by Thermal Advantage Q Series™ software and analyzed by Universal Analysis software (TA Instruments, New Castle, Del.). An exemplary TGA trace is provided in FIG. 15. TGA data showed a weight loss of ~0.26% when the drug powder was heated from room temperature up to ~175° C. at a rate of 10° C./min. The dramatic decrease in the sample weight which began at ~190-200° C. was associated with the sample degradation. Comparison with the DSC data shows that the compound degraded upon melting.

Dynamic Vapor Sorption (DVS): A step isothermal study (25° C.) was conducted on a sample of form IIC using a VTI SGA 100 Symmetric Vapor Sorption Analyzer. An aliquot of approximately 10 mg was weighed in an open platinum dish and exposed to different levels of humidity at 25° C. Relative humidity (RH) steps were from 5% to 95% (adsorption) and from 95% to 5% in increments of 5% RH (desorption). The equilibration criterion was 0.0100 wt % change in 5 min, with a max equilibration time of 180 min. An exemplary DVS scan of form IIC is provided in FIG. 16. The material picked up ~4 wt % moisture at 95% relative humidity (RH). All adsorbed water was released in the desorption stage. The type of the observed hysteresis suggested adsorption of water only on the surface of the material. The compound did not form a hydrate.

ss$^{13}$C-NMR: A ss$^{13}$C-NMR spectra was collected on a sample of form IIC using a 5500 Hz MAS instrument. The peaks were zeroed by collecting a spectrum just prior to the samples using hexamethylbenzene. The methyl peak of hexamethylbenzene was calibrated to 17.35 ppm before the sample was run. An exemplary ss$^{13}$C-NMR of form IIC is provided in FIG. 17.

Solubility: Solubility of form IIC in various media was determined at ambient conditions by equilibrating aliquots of the drug powder with the solvents on a shaking bed for 24 hours. Samples were spun and the supernatant was carefully separated and analyzed by HPLC at the 24-hour timepoint using a stability-indicating method. Tables 11 and 12 provide exemplary solubility for form IIC in various solvents and buffer systems. The data provided in Table 11 is representative. Some variability may occur between lots of a particular sample.

TABLE 11

Solubility of form IIC in various aqueous and organic media (24 h equilibration)

| Aqueous media | Target Conc (mg/ml) | Actual Conc (mg/ml) | pH |
|---|---|---|---|
| Water | 150 | 152 | 1.60 |
| Tetraglucol:Water (1:1) | 50 | 29.6 | 2.08 |
| 0.1N HCl | 100 | 105 | 1.10 |
| pH 7 Tris Buffer | 100 | 30.0 | Not enough sample |
| 0.9% Sodium Chloride | 100 | 33.6 | Not enough sample |
| 1.2% Sodium Chloride | 100 | Too thick to analyze* | NA |
| 0.5% Methylcellulose (MC)/0.5% Sodium Lauryl Sulfate (SLS) | 100 | 94.8 | 1.58 |
| 10% Vitamin E TPGS | 150 | 138 | 1.58 |
| 10% Cremophor | 150 | 137 | 1.64 |
| 1% SLS | 150 | 126 | 1.56 |
| 10% Tween 80 | 150 | 144 | 1.64 |
| 1% Tween 80 | 150 | 130 | 1.60 |
| 1% Pluronic F108 | 150 | 159 | 1.58 |
| 1% Pluronic F68 | 150 | 155 | 1.57 |
| 20% Captisol | 150 | Too thick to analyze* | NA |
| 20% Captisol in pH 3 buffer | 150 | Too thick to analyze* | NA |
| 20% Captisol in pH 7 buffer | 100 | Too thick to analyze* | NA |
| 30% Captisol | 150 | Too thick to analyze* | NA |
| 40% Captisol | 150 | Too thick to analyze* | NA |
| 10% Solutol | 150 | 170 | 1.61 |
| 30% Solutol | 150 | Too thick to analyze* | NA |
| 10% Polyvinyl pyrrolidone (PVP) K30 | 150 | 152 | 1.70 |
| 1% Deoxycholic sodium salt (DOSS) | 150 | 125 | 1.71 |
| 1% Docusate | 150 | 159 | 1.58 |
| 4% Glycerol | 150 | 162 | 1.59 |

*The sample was too thick to analyze it properly due to gel formation

TABLE 12

Solubility of form IIC in 0.05M Buffers at Different pH (24 h equilibration)

| Media (0.05M Buffer) | Actual Conc (mg/ml) | Experimental pH |
|---|---|---|
| Potassium chloride hydrochloric acid, pH 1 | 113 | 1.01 |
| Potassium biphthalate sodium hydroxide, pH 3 | NA | NA |
| Potassium biphthalate sodium hydroxide, pH 5 | NA | NA |
| Potassium phosphate monobasic-sodium hydroxide, pH 7 | 48.2 | Not enough sample |
| Potassium phosphate monobasic-sodium hydroxide, pH 9 | 67.0 | 1.75 |

NA—not available, the sample was too thick to be analyzed properly due to gel formation Example 6

Physical Characterization of Form IID

Various physical characteristics of form IID were evaluated using the following analytical methods:

X-Ray Powder Diffraction (XRPD): The XRPD pattern of a sample of form IID was recorded at room temperature with an X-ray generator (Rigaku/MSC RUH3R) and an X-ray detector (Rigaku/MSC Raxis IIC) in transmission mode. Radiation of Cu Kα at 50 KV×100 mA was used with 2 θ increment rate of 1°/s. The scans ran over a range of 0-40° 2θ with a step size of 1° and a step time of 1 s. The powder sample was held in a 2 mm diameter capillary sample holder (Hampton Research, Laguna Niguel, Calif.). An exemplary XRPD is provided in FIG. 18.

Differential Scanning Calorimetry (DSC): DSC was performed on a sample of form IID using a DSC Q100 Differential Scanning Calorimeter (TA Instruments, New Castle, Del.). The instrument was calibrated with indium. Approximately 2 mg of sample was weighed into an aluminum pan. The pan was crimped with a lid that had a single pinhole. The DSC method used was a ramp of 10° C./min to 300° C. Data were collected using Thermal Advantage Q Series™ software and were analyzed by Universal Analysis Software. An exemplary DSC pattern for form IID is provided in FIG. 19. Only one sharp endothermic event corresponding to the melting of the compound was seen in the DSC data. The melting point was ~205° C. Degradation of the compound upon melting was confirmed by TGA.

Thermogravimetric analysis (TGA): TGA measurements of a sample of form IID were performed using a Model Q500 Thermogravimetric analyzer (TA Instruments, New Castle, Del.). A sample weight of approximately 3-8 mg was placed in platinum pans. The TGA method used was a ramp of 10° C./min to 300° C. Data were collected by Thermal Advantage Q Series software and analyzed by Universal Analysis Software. An exemplary TGA trace is provided in FIG. 20. TGA data showed a weight loss of ~0.6% when the drug powder was heated from room temperature up to ~175° C. at a rate of 10° C./min. The dramatic decrease in the sample weight which began at ~180-190° C. is associated with sample degradation.

Example 8

Physical Characterization of form IIIB

To a suspension of Compound 1 free base (162.9 mg) in EtOH/CH$_2$Cl$_2$ (1:1, 20 mL) was added methanesulfonic acid (28 μL). The mixture was stirred at ~45° C. until dissolution. The solution was then filtered, concentrated in vacuo and the resulting oily residue was redissolved in CH$_2$Cl$_2$ (10 mL) and the solution was added dropwise to a stirred solution of diethylether (~100 mL). The resulting off white precipitate was filtered, washed with diethylether under nitrogen and the solid was then dried overnight under high vacuum at ~40-45° C. to yield form IIIB as a pale brown powder (164.2 mg): HPLC: Rt=4.91 min. (method: solvent B: 0.1% TFA/1% MeCN/water, solvent D: 0.1% TFA/MeCN. Gradient 10% D to 90% D over 8 min. at a flow rate of 1 mL/min. Method length 12 min. Column 1 (YMC 3×150). $^1$H NMR (CD$_3$OD, 500 MHz) 9.02 (d, J=4.9 Hz, 2H), 8.83-8.80 (m, 2H), 8.57 (d, J=2.6 Hz, 1H), 8.11-8.08 (m, 1H), 8.01 (d, J=1.6 Hz, 1H), 7.51 (t, J=4.9 Hz, 1H), 3.38 (q, J=7.3 Hz, 2H), 2.74 (s, 3H, MsOH), 1.25 (t, J=7.3 Hz, 3H), 0.00 (TMS) ppm. MS (ES$^+$) m/z (M$^+$+1) 378.3.

Various physical characteristics of form IIIB were evaluated using the following analytical methods:

X-Ray Powder Diffraction (XRPD): The XRPD pattern of a sample of form IIIB was recorded at room temperature in reflection mode using Bruker D8 Discover system (Asset Tag V012842) equipped with a sealed tube source and a Hi-Star area detector (Bruker AXS, Madison, Wis.). The X-Ray generator was operating at a tension of 40 kV and a current of 35 mA. The powder sample was placed on a Si zero-background wafer. Two frames were registered with an exposure time of 120 s each. The data were subsequently integrated over the range of 3°-41° 2θ with a step size of 0.02° and merged into one continuous pattern. An exemplary XRPD of form IIIB is provided in FIG. 21.

Differential Scanning Calorimetry (DSC): DSC was performed on a sample of form IIIB using a Q200 DSC differential scanning calorimeter (TA Instruments, New Castle, Del.). The instrument was calibrated with indium. A sample of approximately 3-7 mg was weighed into aluminum pans that were crimped using lids with four pin-holes. The DSC sample was scanned using a modulated method from 35° C. to 350° C. at a heating rate of 2° C./min. Data was collected by Thermal Advantage Q Series™ software and analyzed by Universal Analysis software (TA Instruments, New Castle, Del.). An exemplary DSC trace of a sample of form IIIB is provided in FIG. 22. An endotherm was observed at about 215° C., and the sample degraded upon melting.

Thermogravimetric analysis (TGA): A Model Q5000 Thermogravimetric Analyzer (TA Instruments, New Castle, Del.) was used for TGA measurement. A sample of form IIIB with weight of approximately 5-9 mg was scanned from 35° C. to 400° C. at a heating rate of 10° C./min. Data was collected by Thermal Advantage Q Series™ software and analyzed by Universal Analysis software (TA Instruments, New Castle, Del.). An exemplary TGA of a sample of form IIIB is provided in FIG. 23.

Water Vapor Sorption analysis: Vapor Sorption analysis of a sample of form IIIB was done using a SGA-100 Vapor Sorption Analyzer (VTI, Hialeah, Fla.). A sample with weight of approximately 7-12 mg was measured isothermally at 25° C. Data was collected by Isotherm software and analyzed by Microsoft Excel with a VTI macro (VTI, Hialeah, Fla.). An exemplary DVS trace of a sample of form IIIB is provided in FIG. 24. The sample gained about 4.6% in weight from 5 to 95% RH (25° C.).

Single crystal diffraction was performed on a Bruker APEX II CCD diffractometer at room temperature using Cu Kα radiation by using a single crystals picked from mother liquors and mounted on a glass fibers. The oscillation photos were taken around ω axis at 4 φ angles. The data were indexed, integrated, and scaled with the APEX software. The structure was solved and refined with the SHELX-TL package. The crystal shows monoclinic cell with $P2_1/n$ space group. The lattice parameters are a=14.3252(8) Å, b=8.7553 (5) Å, c=17.005(1) Å, α=90°, β=95.340(3)°, γ=90°. Volume=2123.5(2) Å$^3$. Refinement gave final results: R1=3.04%, wR2=8.32%.

$^1$H NMR: A $^1$H NMR spectra was collected on a sample of form IIIB in DMSO using a 500 MHz Bruker instrument. An exemplary $^1$H NMR of form IIIB is provided in FIG. 26.

ss$^{13}$C-NMR: A ss$^{13}$C-NMR spectra was collected on a sample of form IIIB using a 5500 Hz MAS instrument. The peaks were zeroed by collecting a spectrum just prior to the samples using hexamethylbenzene. The hexamethylbenzene methyl peak was calibrated to 17.35 ppm before the sample was run. An exemplary ss$^{13}$C-NMR of form IIIB is provided in FIG. 27.

Solubility: Solubility of form IIIB in various media was determined at ambient conditions by equilibrating aliquots of the drug powder with the medium on a shaking bed for 24 hours. The samples were centrifuged, the saturated solutions of the drug were then separated and analyzed by HPLC. The sample volume was 100 μL, and the target concentration was 10 mg/ml. The saturated solutions were diluted appropriately and analyzed by HPLC. Solubility data for Lot 3 were obtained using a generic HPLC method (HPLC column: Waters C18, 3.5 μm, 75 mm; flow 1.7 ml/min, mobile phase: mixture of A (85% water containing 0.1% $H_3PO_4$) and B (15% acetonitrile containing 0.1% $H_3PO_4$), gradient method was used: gradient from 15 to 35% of B over 6 min, then gradient 35-15% of B over 30 s and then hold at 15% B for 1.5 min; retention time: 4.0 min, wavelength: 284 nm. The rest of the solubility data included in this report have been generated using a stability indicating method for form IIIB Table 13 below depicts the solubility of exemplary form IIIB in various media.

TABLE 13

Solubility of form IIIB in various aqueous and organic media

| Media | Total Conc (mg/ml) |
| --- | --- |
| SolubilitySV, Captisol, 20% | 3.81 |
| SolubilitySV, Ethanol | 0.439 |
| SolubilitySV, HCl, 0.1N | 12.2 |
| SolubilitySV, Miglyol810 | 0.0219 |
| SolubilitySV, Octanol | 0.0584 |
| SolubilitySV, PEG400 | 0.729 |
| SolubilitySV, PluronicF108, 1% | >12.0 |
| SolubilitySV, PropyleneGlycol | 5.74 |
| SolubilitySV, SodiumLaurylSulfate, 1% | 0.623 |
| SolubilitySV, TrisBuffer, pH 7 | 0.0276 |
| SolubilitySV, Vitamin E TPGS, 10% | 11.5 |
| SolubilitySV, Water | >12.0 |
| SolubilitySV, Captisol, 30%, pH 7 | 0.634 |
| SolubilitySV, SGF | >12.0 |
| SolubilitySV, SIF | 0.0284 |
| SolubilitySV, Vitamin E TPGS, 10%; 1% HPMC | >12.0 |

Example 9

Physical Characterization of Form IIIC

Form IIIC was made by suspending 37.3 mg of free base in 6 ml of chloroform. To the resulting suspension was added 1.98 ml of 0.05M methanesulfonic acid aqueous solution. The resulting slurry was triturated for 10 min. Form IIIC resulted and was isolated by filtration and air dried.

Various physical characteristics of an exemplary form IIIC were evaluated using the following analytical methods:

X-Ray Powder Diffraction (XRPD): The XRPD pattern of a sample of form IIIC was recorded at room temperature in reflection mode using Bruker D8

Discover system equipped with a sealed tube source and a Hi-Star area detector (Bruker AXS, Madison, Wis.). The X-Ray generator was operating at a tension of 40 kV and a current of 35 mA. The powder sample was placed on a Si zero-background wafer. Two frames were registered with an exposure time of 120 s each. The data were subsequently integrated over the range of 3°-41° 2θ with a step size of 0.02° and merged into one continuous pattern. An exemplary XRPD of form IIIC is provided in FIG. 28.

Differential Scanning Calorimetry (DSC): DSC was performed on a sample of form IIIC using a Q1000 DSC differential scanning calorimeter (TA Instruments, New Castle, Del.). The instrument was calibrated with indium. A sample of approximately 3-7 mg was weighed into aluminum pans that were crimped using lids with single pin-holes. The DSC sample was scanned using a ramp method from 30° C. to 300° C. at a heating rate of 2° C./min. Data was collected by Thermal Advantage Q Series™ software and analyzed by Universal Analysis software (TA Instruments, New Castle, Del.). An exemplary DSC scan of form IIIC is provided in FIG. 29.

Thermogravimetric analysis (TGA): A Model Q500 Thermogravimetric Analyzer (TA Instruments, New Castle, Del.) was used for TGA measurement. A sample of form IIIC with weight of approximately 5-9 mg was scanned from 20° C. to 400° C. at a heating rate of 10° C./min. Data was collected by Thermal Advantage Q Series™ software and analyzed by Universal Analysis software (TA Instruments, New Castle, Del.). An exemplary TGA scan of form IIIC is provided in FIG. 30.

A number of embodiments of the invention have been described. Nevertheless, it will be understood that various modifications may be made without departing from the spirit and scope of the invention. Accordingly, other embodiments are within the scope of the following claims.

What is claimed is:

1. Crystalline 1-ethyl-3-(5-(5-fluoropyridin-3-yl)-7-(pyrimidin-2-yl)-1H-benzo[d]imidazol-2-yl)urea.

2. 1-ethyl-3-(5-(5-fluoropyridin-3-yl)-7-(pyrimidin-2-yl)-1H -benzo[d]imidazol-2-yl)urea.monoesylate.

3. Crystalline 1-ethyl-3-(5-(5-fluoropyridin-3-yl)-7-(pyrimidin-2-yl)-1H -benzo[d]imidazol-2-yl)urea.monoesylate.

4. The crystalline 1-ethyl-3-(5-(5-fluoropyridin-3-yl)-7-(pyrimidin-2-yl)-1H-benzo[d]imidazol-2-yl)urea.monoesylate of claim 3, having an aqueous solubility of greater than 150 mg/ml at pH 1.

5. The crystalline 1-ethyl-3-(5-(5-fluoropyridin-3-yl)-7-(pyrimidin-2-yl)-1H-benzo[d]imidazol-2-yl)urea.monoesylate of claim 3, characterized by a $T_m$ of about 216° C. as measured by DSC.

6. The crystalline 1-ethyl-3-(5-(5-fluoropyridin-3-yl)-7-(pyrimidin-2-yl)-1H-benzo[d]imidazol-2-yl)urea.monoesylate of claim 3, characterized by an 11% weight gain from 5% to 95% relative humidity at 25° C.

7. 1-ethyl-3-(5-(5-fluoropyridin-3-yl)-7-(pyrimidin-2-yl)-1H-benzo[d]imidazol-2-yl)urea.monomesylate.

8. Crystalline 1-ethyl-3-(5-(5-fluoropyridin-3-yl)-7-(pyrimidin-2-yl)-1H -benzo[d]imidazol-2-yl)urea.monomesylate.

9. The crystalline 1-ethyl-3-(5-(5-fluoropyridin-3-yl)-7-(pyrimidin-2-yl)-1H-benzo[d]imidazol-2-yl)urea.monomesylate of claim 8, characterized by a weight gain of 4.6% from 5% to 95% relative humidity at 25° C.

10. The crystalline 1-ethyl-3-(5-(5-fluoropyridin-3-yl)-7-(pyrimidin-2-yl)-1H-benzo[d]imidazol-2-yl)urea.monomesylate of an of claim 8, having an aqueous solubility of greater than 12 mg/ml at pH 4.4.

11. The crystalline 1-ethyl-3-(5-(5-fluoropyridin-3-yl)-7-(pyrimidin-2-yl)-1H-benzo[d]imidazol-2-yl)urea.monomesylate of claim 8, wherein the crystalline 1-ethyl-3-(5-(5-fluoropyridin-3-yl)-7-(pyrimidin-2-yl)-1H-benzo[d]imidazol-2-yl)urea.monomesylate remains in the same physical form for at least 1 month at 40° C./75% relative humidity.

12. The crystalline 1-ethyl-3-(5-(5-fluoropyridin-3-yl)-7-(pyrimidin-2-yl)-1H-benzo[d]imidazol-2-yl)urea.monomesylate of claim 8, wherein the crystalline 1-ethyl-3-(5-(5-fluoropyridin-3-yl)-7-(pyrimidin-2-yl)-1H-benzo[d]imidazol-2-yl)urea.monomesylate remains chemically stable for at least 1 month at 40° C./75% relative humidity.

* * * * *